(12) United States Patent
Jakubowski et al.

(10) Patent No.: US 11,168,182 B2
(45) Date of Patent: Nov. 9, 2021

(54) STAR MACROMOLECULES FOR PERSONAL AND HOME CARE

(71) Applicant: PILOT POLYMER TECHNOLOGIES, INC., Pittsburgh, PA (US)

(72) Inventors: Wojciech Jakubowski, Sugar Land, TX (US); Patrick McCarthy, Pittsburgh, PA (US); Nicolay Tsarevsky, Dallas, TX (US); James Spanswick, Pittsburgh, PA (US)

(73) Assignee: Pilot Polymer Technologies, Inc., Pittsburgh, PA (US)

( * ) Notice: Subject to any disclaimer, the term of this patent is extended or adjusted under 35 U.S.C. 154(b) by 0 days.

(21) Appl. No.: 16/914,056

(22) Filed: Jun. 26, 2020

(65) Prior Publication Data
US 2020/0325282 A1    Oct. 15, 2020

Related U.S. Application Data

(63) Continuation of application No. 16/286,267, filed on Feb. 26, 2019, now Pat. No. 10,696,798, which is a (Continued)

(51) Int. Cl.
| | |
|---|---|
| *C08F 265/02* | (2006.01) |
| *C08G 83/00* | (2006.01) |
| *A61K 8/72* | (2006.01) |
| *A61K 8/81* | (2006.01) |
| *A61Q 19/00* | (2006.01) |
| *C08F 293/00* | (2006.01) |

(Continued)

(52) U.S. Cl.
CPC .............. *C08G 83/003* (2013.01); *A61K 8/72* (2013.01); *A61K 8/8147* (2013.01); *A61K 8/8152* (2013.01); *A61K 8/90* (2013.01); *A61Q 19/00* (2013.01); *C08F 265/02* (2013.01); *C08F 265/04* (2013.01); *C08F 293/005* (2013.01); *C08F 299/04* (2013.01); *C08F 299/0492* (2013.01); *A61K 2800/10* (2013.01); *A61K 2800/48* (2013.01); *C08J 2300/206* (2013.01)

(58) Field of Classification Search
CPC .................................................. C08J 2300/206
See application file for complete search history.

(56) References Cited

U.S. PATENT DOCUMENTS

| | | | | |
|---|---|---|---|---|
| 8,569,421 | B2 * | 10/2013 | Jakubowski | ........... A61Q 19/00 525/244 |
| 9,399,694 | B2 * | 7/2016 | Jakubowski | ......... C08G 83/003 |

(Continued)

FOREIGN PATENT DOCUMENTS

WO    WO-2005116097 A1 * 12/2005 ............. C08F 299/00

*Primary Examiner* — Mark S Kaucher
(74) *Attorney, Agent, or Firm* — Ulmer and Berne, LLP

(57) ABSTRACT

A polymer composition comprising star macromolecules is provided. Each star macromolecule has a core and five or more arms, wherein the number of arms within a star macromolecule varies across the composition of star molecules. The arms on a star are covalently attached to the core of the star; each arm comprises one or more (co)polymer segments; and at least one arm and/or at least one segment exhibits a different solubility from at least one other arm or one other segment, respectively, in a reference liquid of interest.

20 Claims, 26 Drawing Sheets

Related U.S. Application Data continuation of application No. 15/174,727, filed on Jun. 6, 2016, now Pat. No. 10,221,285, which is a continuation of application No. 14/037,031, filed on Sep. 25, 2013, now Pat. No. 9,382,370, which is a continuation of application No. 13/410,700, filed on Mar. 2, 2012, now Pat. No. 8,604,132, which is a continuation of application No. 12/926,143, filed on Oct. 27, 2010, now Pat. No. 8,173,750, which is a continuation-in-part of application No. 12/799,411, filed on Apr. 23, 2010, now Pat. No. 8,569,421.

(60) Provisional application No. 61/214,397, filed on Apr. 23, 2009.

(51) Int. Cl.
*C08F 265/04* (2006.01)
*C08F 299/04* (2006.01)
*A61K 8/90* (2006.01)

(56) References Cited

U.S. PATENT DOCUMENTS

| | | | |
|---|---|---|---|
| 10,696,798 B2 * | 6/2020 | Jakubowski | A61K 8/8152 |
| 2008/0114128 A1 * | 5/2008 | Destarac | C08F 299/00 |
| | | | 525/193 |
| 2016/0375143 A1 * | 12/2016 | Gunatillake | A61P 27/02 |
| | | | 514/44 A |

* cited by examiner

A  B

A) GPC Traces

B) Ratio of arms: PSt-b-PtBA / PtBA = 1 / 4

STAR MACROMOLECULES FOR PERSONAL AND HOME CARE

CROSS-REFERENCE TO RELATED APPLICATIONS

This application is a continuation of U.S. patent application Ser. No. 16/286,267, filed Feb. 26, 2019, which is a continuation of U.S. patent application Ser. No. 15/174,727, filed Jun. 6, 2016, now U.S. Pat. No. 10,221,285, granted Mar. 5, 2019, which is a continuation of U.S. patent application Ser. No. 14/037,031, filed Sep. 25, 2013, now U.S. Pat. No. 9,382,370, granted Jul. 5, 2016, which is a continuation of U.S. patent application Ser. No. 13/410,700, filed Mar. 2, 2012, now U.S. Pat. No. 8,604,132, granted Dec. 10, 2013, which is a continuation of U.S. application Ser. No. 12/926,143, filed Oct. 27, 2010, now U.S. Pat. No. 8,173,750, granted May 8, 2012, which is a continuation-in-part of U.S. patent application Ser. No. 12/799,411, filed Apr. 23, 2010, now U.S. Pat. No. 8,569,421, granted Oct. 29, 2013, which claims the priority benefit of U.S. Provisional Application No. 61/214,397, filed Apr. 23, 2009. All of the foregoing related applications, in their entirety, are incorporated by reference herein.

FIELD OF THE INVENTION

The present invention relates to multi-arm star macromolecules which are used as rheology modifiers, including use in the cosmetic, personal care and home care compositions.

BACKGROUND AND PRIOR ART

Most personal care products on the market contain many types of polymers that vary by structure, chemistry, and raw material source (synthetic or natural) that are combined to provide products with many different desired functions. One class of polymer additives is targeted at altering or modifying the rheological properties of the product that are very important for consumer appeal. Often, additives that provide sufficient viscosity are needed, especially for those formulations where the viscosity without additives is close to that of the pure solvent (water). However, merely increasing viscosity is not sufficient, and in reality, the modifiers should be selected to provide certain desired rheological properties for the formulation that depend on its nature, the mode of delivery, type of flow, and the aesthetic appeal of final application. Typically, low molecular weight surfactants are used to modify rheological properties but they have to be used at large concentrations. Resulting in relatively high cost, and an adverse impact on the environment (e.g., water pollution).

The thickeners used in cosmetic and body care preparations have to meet stringent requirements. First and foremost, they have to show high compatibility and also—if possible—biodegradability so that many substances have to be ruled out from the outset for use in cosmetics. In addition, they should be universally useable in aqueous, emulsoidal, alcoholic and oil-containing bases, be readily processable and lead to a rheology which enables the product to be easily applied so that the preparations can be removed and distributed under clean and simple conditions.

Thickeners that are designed molecular level to provide the desired properties would be expected to be compatible with many other auxiliaries, more particularly with salts and surfactants. The thickener itself and the other auxiliaries should also lend themselves to ready incorporation into the formulation. The thickened preparations are also expected to show stable rheology and an unchanging physical and chemical quality even in the event of long-term storage and changes in pH and temperature. Finally, the thickeners should be inexpensive to produce without causing significant environmental pollution.

In view of this complex requirement profile, it is clear why, even today, there is still a demand for new thickeners in the cosmetics field.

SUMMARY OF THE INVENTION

Accordingly, in one aspect the invention provides a polymer composition comprising star macromolecules, each star macromolecule having a core and five or more arms, wherein the number of arms within a star macromolecule varies across the composition of star molecules; and the arms on a star are covalently attached to the core of the star; each arm comprises one or more (co)polymer segments; and at least one arm and/or at least one segment exhibits a different solubility from at least one other arm or one other segment, respectively, in a reference liquid of interest.

The use of the polymer composition in personal care products and home care products is also provided.

In one aspect of the invention, there is a process of forming a mikto star macromolecule comprising:
i) creating a reaction mixture comprising a plurality of first polymeric segments having an ATRP-functional terminal group and a plurality of second monomers, wherein at least a portion of the first polymeric segments are formed by polymerizing a plurality of first monomers, non-limiting examples of first monomers include hydrophobic monomers;
ii) forming a second polymeric segment extending from said first polymeric segment by activating the ATRP-functional terminal group on said first polymeric segment to initiate polymerization of a portion of the second monomers, to form a plurality of block copolymeric arms;
iii) during the polymerization of the second monomers, introducing a plurality of second monomer initiators having an ATRP functional terminal group into the reaction mixture;
iv) activating the ATRP-functional terminal group on said second monomer initiator to initiate polymerization of a second portion of the second monomer, to form a plurality of homopolymeric arms; and
v) crosslinking at least a portion of the block copolymeric arms and at least a portion of the homopolymeric arms to form at least one mikto star macromolecule.

In one aspect of the invention, there is a star macromolecule that forms a gel when dissolved in water at a concentration of at least 0.2 wt. % and is formed by:
i) creating a reaction mixture comprising a plurality of first polymeric segments having an ATRP-functional terminal group and a plurality of second monomers, wherein at least a portion of the first polymeric segments are formed by polymerizing a plurality of first monomers;
ii) forming a second polymeric segment extending from said first polymeric segment by activating the ATRP-functional terminal group on said first polymeric segment to initiate polymerization of a portion of the second monomers, to form a plurality of block copolymeric arms;
iii) during the polymerization of the second monomers, introducing a plurality of second monomer initiators having an ATRP functional terminal group into the reaction mixture;

iv) activating the ATRP-functional terminal group on said second monomer initiator to initiate polymerization of a second portion of the second monomer, to form a plurality of homopolymeric arms; and v) crosslinking at least a portion of the block copolymeric arms and at least a portion of the homopolymeric arms;

wherein:

a) the gel has a dynamic viscosity of at least 20,000 cP; and b) the star macromolecule has a molecular weight of 150,000 g/mol and 600,000 g/mol.

In one aspect of the invention, there is a star macromolecule polymer composition comprising one or more star macromolecules prepared by an improved, efficient arm-first living-controlled radical polymerization method, wherein the one or more star macromolecules are represented by Formula X:

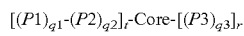

$$[(P1)_{q1}\text{-}(P2)_{q2}]_t\text{-Core-}[(P3)_{q3}]_r$$ Formula X wherein:

Core represents a crosslinked polymeric segment;

P1 represents a hydrophobic homopolymeric segment comprised of repeat units of monomeric residues of polymerized hydrophobic monomers;

P2 represents a hydrophilic homopolymeric segment comprised of repeat units of monomeric residues of polymerized hydrophilic monomers;

P3 represents a hydrophilic homopolymeric segment comprised of repeat units of monomeric residues of polymerized hydrophilic monomers;

q1 represents the number of repeat units in P1 and has a value between 1 and 50;

q2 represents the number of repeat units in P2 and has a value between 30 and 500;

q3 represents the number of repeat units in P3 and has a value between 30 and 500;

r represents the number of homopolymeric arms covalently attached to the Core;

t represents the number of copolymeric arms covalently attached to the Core; and wherein the molar ratio of r to t is in the range of between 20:1 and 2:1.

In one aspect of the invention, there is a star macromolecule having a molecular weight of between 150,000 g/mol and 600,000 g/mol that forms a clear homogeneous gel when dissolved in water at a concentration of at least 0.2 wt. % wherein the gel has:

i) a dynamic viscosity of at least 20,000 cP;
ii) a salt-induced break value of at least 60%;
iii) a pH-induced break value of at least 80%;
iv) a shear-thinning value of at least 10; and/or
v) an emulsion value of >12 hours.

In one aspect of the invention, there is a clear homogeneous gel, comprising a star macromolecule having a molecular weight of between 150,000 g/mol and 600,000 g/mol, comprises the following properties:

i) a dynamic viscosity of at least 20,000 cP;
ii) a salt-induced break value of at least 60%;
iii) a pH-induced break value of at least 80%;
iv) a shear-thinning value of at least 10; and/or
v) an emulsion value of >12 hours;

wherein the clear homogeneous gel is formed when the star macromolecule is dissolved in water at a concentration of at least 0.2 wt. %.

In one aspect of the invention, there is an emulsifier-free emulsion comprising:

a water-soluble star macromolecule having:
i) molecular weight of at least 150,000 g/mol; and
ii) a dynamic viscosity of at least 20,000 cP at a concentration of 0.4 wt. %.

In one aspect of the invention, there is an emulsion comprising:

a water-soluble star macromolecule having:
i) a molecular weight of at least 150,000 g/mol; and
ii) a dynamic viscosity of at least 20,000 cP at a concentration of 0.4 wt. %.

In one aspect of the invention, there is a thickening agent that forms a clear homogeneous gel when dissolved in water at a concentration of at least 0.2 wt. %, wherein the gel has:

i) a dynamic viscosity of at least 20,000 cP;
ii) a salt-induced break value of at least 60%;
iii) a pH-induced break value of at least 80%;
iv) a shear-thinning value of at least 10; and/or
v) an emulsion value of greater than 12 hours.

In one aspect of the invention, the star macromolecule, emulsifier, gel, emulsifier-free emulsion, emulsion and/or thickening agent, including those formed by the one-pot process, ATRP, CRP, and/or combinations of one or more of these processes, may be used to provide a certain level of control over viscosity and consistency factors in many aqueous and oil based systems including, for example, water- and solvent-based coating compositions, paints, inks, antifoaming agents, antifreeze substances, corrosion inhibitors, detergents, oil-well drilling-fluid rheology modifiers, additives to improve water flooding during enhanced oil recovery, dental impression materials, cosmetic and personal care applications including hair styling, hair sprays, mousses, hair gels, hair conditioners, shampoos, bath preparations, cosmetic creams, cosmetic gels, lotions, ointments, deodorants, powders, skin cleansers, skin conditioners, skin emollients, skin moisturizers, skin wipes, sunscreens, shaving preparations, and fabric softeners.

In one aspect of the invention, there is a macromolecule, comprising: a plurality of arms comprising at least two types of arms, wherein a first-arm-type extends beyond a second-arm-type and said first-arm-type has a hydrophobic segment on its distal end, wherein at least a portion of the hydrophobic segment may extend beyond the length of the second-arm-types either by the size of the monomeric segment or segments (which may be varied by length of monomeric residue, degree of polymerization, and/or both) for which the hydrophobic segment is attached. Recognizing that the "length" of an arm or segment and the "extending beyond" limitation may be theoretical, meaning that while it is not empirically measured it is understood to "extend beyond" and/or have a longer "length" relative to the length of the second-arm-type if the degree of polymerization is greater for monomeric residues of the same type or of the same theoretical length.

In one aspect of the invention, there is a star macromolecule, comprising: a plurality of arms comprising at least two types of arms, wherein the degree of polymerization of a first-arm-type is greater than the degree of polymerization of a second-arm-type, and wherein said first-arm-type has a distal end portion that is hydrophobic. In another aspect of the invention, this star macromolecule may be formed by first forming or obtaining the hydrophobic portion and then forming the remaining portion of the first-arm-type from the end of the hydrophobic portion and the second-arm-type in a one-pot synthesis wherein the polymerization of the second portion of the first-arm-type is commenced prior to the initialization of the second-arm-type but there is at least some point wherein portions, e.g., substantial portions, of the first-arm-type and second-arm-type are being polymerically extended simultaneously.

In one aspect of the invention, there is an oil-soluble star macromolecule, comprising: a plurality of different arms comprising at least two types of arms, wherein a first-arm-type extends beyond a second-arm-type and said first-arm-type has a hydrophilic segment on its distal end.

In one aspect of the invention, there is an oil-soluble star macromolecule, comprising: a plurality of arms comprising at least two types of arms, wherein the degree of polymerization of a first-arm-type is greater than the degree of polymerization of a second-arm-type, and wherein said first-arm-type has a hydrophilic segment on its distal end.

In one aspect of the invention, there is a star macromolecule, comprising: a plurality of arms comprising at least two types of arms, wherein the degree of polymerization of a first-arm-type is greater than the degree of polymerization of a second-arm-type, and wherein said first-arm-type has a distal end portion that is hydrophobic and the proximal portion of the first-arm-type and second-arm-type are the same with the only difference between the first-arm-type and the second-arm-type being that the first-arm-type has a hydrophobic portion on its distal end. In another aspect of the invention, this star macromolecule may be formed by first forming or obtaining the hydrophobic portion and then forming the remaining portion of the first-arm-type from the end of the hydrophobic portion and the second-arm-type simultaneously in a one-pot synthesis.

In an aspect of the invention, the star macromolecules may have an HLM of greater than 0.85, for example greater than 0.87. or 0.9 or 0.93 or 0.95 or 0.97 or 0.98.

In an aspect of the invention, the star macromolecules may have a calculated HLM of greater than 0.85, for example greater than 0.87. or 0.9 or 0.93 or 0.95 or 0.97 or 0.98 and a viscosity of greater than 60,000 cP at a pH between 7 to 10.5 and a molecular weight of between 200,000 g/mol and 550,000 g/mol and a shear-thinning value of at least 10 and, optionally, a salt-induced break value of at least 60%.

BRIEF DESCRIPTION OF THE DRAWINGS

The features and advantages of the present invention may be better understood by reference to the accompanying Figures, in which.

DETAILED DESCRIPTION OF THE INVENTION

Figure 1:
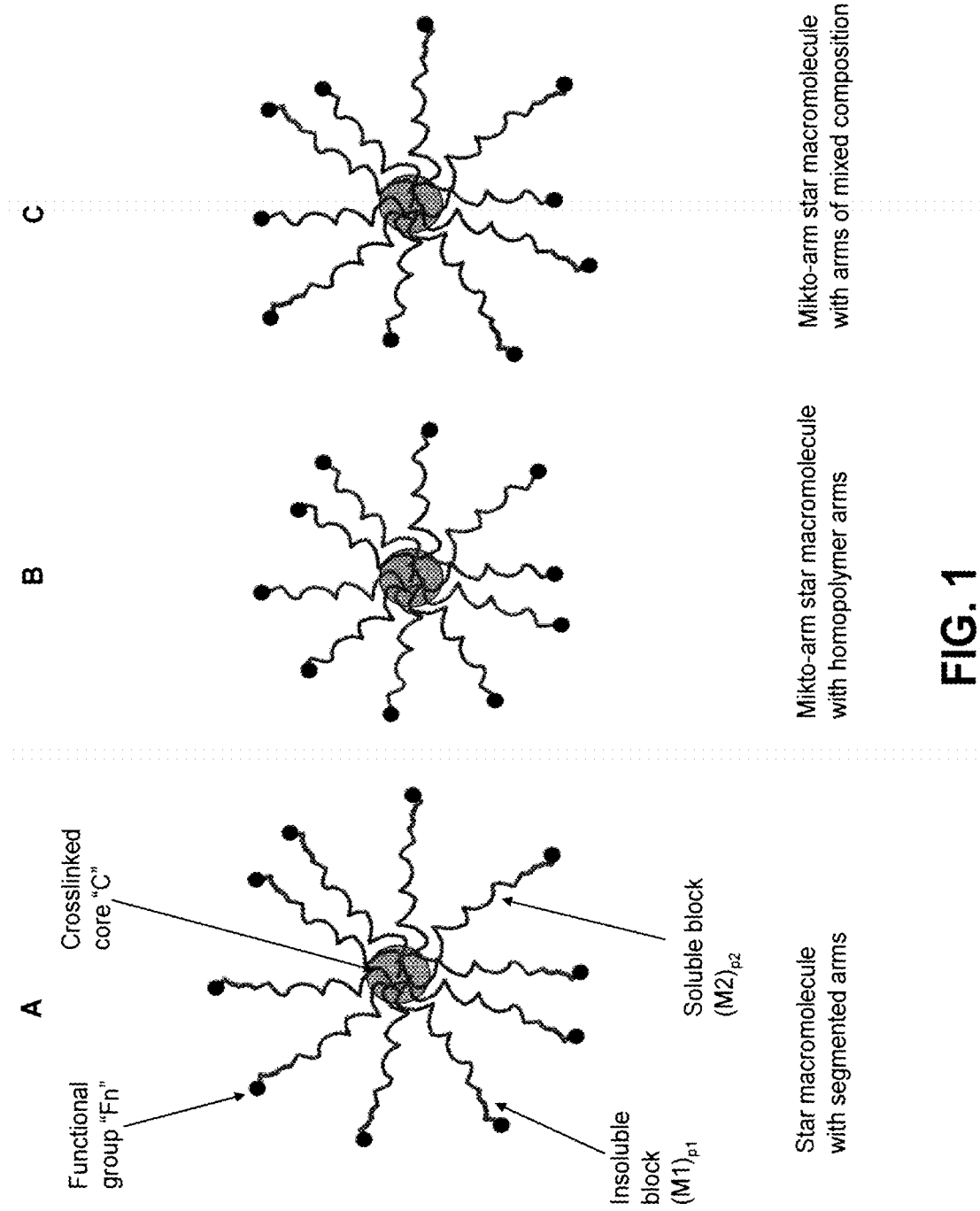
FIG. 1: Illustration of the structure of a segmented homo-arm star macromolecule and two different types of mikto-arm star macromolecules.

The term "solubility" or "soluble" is understood to mean that when a component is mixed into a solvent and tested, at STP in a 1 cm cuvette, it has a light transmittance value, at a wavelength at or around a UV/Vis minimum wavelength for the mixture, of at least 40%, for example, at least 50%, 70%, 85%, or at least 95%.

The term "clear" as is used to describe a homogenous gel or homogenous solution is understood to mean that when the gel or solution is tested, at STP in a 1 cm cuvette, it has a light transmittance value, at a wavelength at or around a UV/Vis minimum wavelength for the gel or solution, of at least 40%, for example, at least 50%, 70%, 85%, or at least 95%.

The term "water-soluble monomer" is understood to mean a monomer having at least about 10 wt. % solubility in water at STP. For example, a water soluble monomer may have at least 15 wt. %, 20 wt. %, 25 wt. %, or at least 30 wt. % solubility in water at STP.

The term "water-insoluble monomer" is understood to mean a monomer having less water solubility than a water soluble monomer, for example, less that about 5 wt. %, such as less than 1 wt. % or 0.5 wt. % solubility in water at STP.

The term "water-soluble star macromolecule" is understood to mean a star macromolecule that is soluble in water, pH adjusted if necessary to a pH of no greater than 8 with sodium hydroxide, at a concentration of at least 5 g/L, for example, between 8 g/L to 100 g/L, such as, at least 10 g/L, 12 g/L, 15 g/L, or at least 20 g/L. For example, a water-soluble star macromolecule having an aqueous solubility of at least 10 g/L may include the introduction of at least 10 g of the star macromolecule into approximately 1 L of water, neutralizing the mixture, if necessary, by adjusting the pH of the resulting mixture to about pH 8 (e.g., with the addition of base, such as sodium hydroxide), and vigorously stirring at a temperature no greater than 100° C. for no more than about 60 minutes, to achieve dissolution of the star macromolecule, and testing the solubility at STP.

The term "oil-soluble star macromolecule" is understood to mean a star macromolecule that is soluble in mineral oil at a concentration of at least 5 g/L, for example, between 8 g/L to 100 g/L, such as, at least 10 g/L, 12 g/L, 15 g/L, or at least 20 g/L of mineral oil. For example, an oil-soluble star macromolecule having an oil solubility of at least 10 g/L may include the introduction of at least 10 g of the star macromolecule into approximately 1 L of mineral oil, and vigorously stirring at a temperature no greater than 100° C. for no more than about 60 minutes, to achieve dissolution of the star macromolecule, and testing the solubility at STP.

The term "hydrophilic" is understood to mean, in relation to a material, such as a polymeric arm, or a polymeric segment of a polymeric arm, that the material is water soluble and comprises hydrophilic segments having an HLB equal to or greater than 8, for example, an HLB equal to 16-20, or equal to or greater than 18, 19, or 19.5. In certain embodiments, the hydrophilic segment may comprise at least 75 mol % of water-soluble monomer residues, for example, between 80 mol % to 100 mol % or at least 85 mol %, 90 mol %, 95 mol %, or at least 97 mol % water-soluble monomer residues.

The term "hydrophobic" is understood to mean, in relation to a material, such as a polymeric arm, or a polymeric segment of a polymeric arm, that the material is water insoluble and comprises hydrophobic segments having an HLB less than 8, for example, an HLB less than 7. In certain embodiments, the hydrophobic segment may comprise at least 75 mol % of water-insoluble monomer residues, for example, between 80 mol % to 100 mol % or at least 85 mol %, 90 mol %, 95 mol %, or at least 97 mol % water-insoluble monomer residues.

The term "monomer residue" or "monomeric residue" is understood to mean the residue resulting from the polymerization of the corresponding monomer. For example, a polymer derived from the polymerization of an acrylic acid monomer (or derivatives thereof, such as acid protected derivatives of acrylic acid including but not limited to methyl or t-butyl ester of acrylic acid), will provide polymeric segments, identified as PAA, comprising repeat units of monomeric residues of acrylic acid, i.e., "—CH(CO$_2$H)CH$_2$—". For example, a polymer derived from the polymerization of styrene monomers will provide polymeric segments, identified as PS, comprising repeat units of monomeric residues of styrene, i.e., "—CH(C$_6$H$_5$)CH$_2$—."

For example, a polymer derived from the polymerization of monomeric divinylbenzene monomers will provide polymeric segments comprising repeat units of monomeric residues of divinylbenzene, i.e., "—CH$_2$CH(C$_6$H$_5$)CHCH$_2$—."

The term "emulsifier" is understood to mean a component that comprises an appreciable weight percent of an amphiphilic compound having a molecular weight of less than 5,000 MW. Emulsifiers are usually linear organic compounds that contain both hydrophobic portions (tails) and hydrophilic portions (heads), i.e., are amphiphilic. Examples of emulsifiers include but are not limited to: alkyl benzenesulfonates, alkanesulfonates, olefin sulfonates, alkylethersulfonates, glycerol ether sulfonates, .alpha.-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkylsulfosuccinates, mono- and dialkylsulfosuccinamates, sulfotriglycerides, ether carboxylic acids and salts thereof, fatty acid isethionates, fatty acid sarcosinates, fatty acid taurides, acyl lactylates, acyl tartrates, acyl glutamates, acyl aspartates, alkyl oligoglucoside sulfates, protein fatty acid condensates (particularly wheat-based vegetable products) and alkyl (ether) phosphates, alkylbetaines, alkylamidobetaines, aminopropionates, aminoglycinates, imidazoliniumbetaines and sulfobetaines.

The term "emulsifier-free" is understood to mean a composition or mixture wherein the formulation is substantially devoid of any emulsifiers, for example less than 0.1 wt. % of emulsifier, relative to the total composition, or less than 0.05 wt. % of emulsifier, relative to the total composition, or less than 0.01 wt. % of emulsifier, relative to the total composition, or a formulation where there is no emulsifier.

The term "STP" is understood to mean standard conditions for temperature and pressure for experimental measurements, wherein the standard temperature is a temperature of 25° C. and the standard pressure is a pressure of 1 atm.

Structure of the Polymer Composition

Multi-arm star macromolecules are shown schematically in FIG. 1

In one embodiment, the arms in a star macromolecule are comprised of two or more (co)polymer segments selected to modify the rheology of the reference liquid of interest. The star macromolecule structure is represented by the following formula [F-(M1)$_{p1}$-(M2)$_{p2}$]$_n$-C wherein i. [F-(M1)$_{p1}$-(M2)$_{p2}$] represents an arm comprised of a segmented (co)polymer chain wherein each (co)polymer segment, ii. (M1)$_{p1}$- and (M2)$_{p2}$- are compositionally distinct adjacent (co)polymer segments where each segment is comprised of one or more monomers with homo, random, gradient or block (co)polymer structure and where p1 and p2 represent the degree of polymerization of each copolymer segment, iii. F- represents an optionally functional group or mixture of functional groups present on the arm chain-end, iv. (M1)$_{p1}$ is not soluble or not fully soluble in the reference liquid of interest, v. (M2)$_{p2}$ is soluble or mostly soluble in the reference liquid of interest, vi. and C represents the crosslinked core of the star macromolecule which is comprised of crosslinker (Mx), crosslinker (Mx) and monomer (My), crosslinker (Mx) and (M2), or a mixture of (Mx), (My) and (M2), and vii. n represents the average number of arms covalently attached to the core of the star macromolecule.

In another embodiment, the star macromolecule structure can be represented by the following formula, $$[F\text{-}(M1)_{p1}\text{-}(M2)_{p2}]_n\text{-}C\text{-}[(M3)_{p3}\text{-}F]_m \text{ wherein}$$

i. [F-(M1)$_{p1}$-(M2)$_{p2}$] represents an arm comprised of a segmented (co)polymer chain,
ii. (M1)$_{p1}$- and (M2)$_{p2}$- are compositionally distinct adjacent (co)polymer segments where each segment is comprised of one or more monomers with homo, random, gradient or block (co)polymer structure and where p1 and p2 represent the degree of polymerization of each copolymer segment,
iii. F- represents an optionally functional group or mixture of functional groups present on the arm chain-end,
iv. (M1)$_{p1}$ is not soluble or not fully soluble in the reference liquid of interest,
v. (M2)$_{p2}$ is soluble or mostly soluble in the reference liquid of interest,
vi. and C represents the crosslinked core of the star macromolecule which is comprised of crosslinker (Mx), crosslinker (Mx) and monomer (My), crosslinker (Mx) and (M2), or a mixture of (Mx), (My) and (M2), and
vii. n represents the average number of arms covalently attached to the core of the star macromolecule.
viii. (M3)$_{p3}$ is a (co)polymer segment which is comprised of one or more monomers with homo, random, gradient or block (co)polymer structure with a degree of polymerization p3 and
ix. m is the number of (M3)$_{p3}$ (co)polymer arms covalently attached to the core,
x. (M3)$_{p3}$ is soluble or mostly soluble in the reference liquid of interest and
xi. M2 and M3 can be comprised of the same or different (co)monomers.

In a further embodiment, polymer composition comprises star macromolecules in which the structure of a star can be represented by the following formula, $$[F\text{-}(M1)_{p1}]_s\text{-}C\text{-}[(M3)_{p3}\text{-}F]_m \text{ wherein}$$

i. [F-(M1)$_{p1}$-(M2)$_p$2] represents an arm comprised of a segmented (co)polymer chain,
ii. (M1)$_{p1}$- is a (co)polymer segment where each segment is comprised of one or more monomers with homo, random, gradient or block (co)polymer structure with a degree of polymerization p1,
iii. F- represents an optionally functional group or mixture of functional groups present on the arm chain-end,
iv. (M1)$_{p1}$ is not soluble or not fully soluble in the reference liquid of interest,
v. C represents the crosslinked core of the star macromolecule which is comprised of crosslinker (Mx), crosslinker (Mx) and monomer (My), crosslinker (Mx) and (M2), or a mixture of (Mx), (My) and (M2), and
vi. (M3)$_{p3}$ is a (co)polymer segment which is comprised of one or more monomers with homo, random, gradient or block (co)polymer structure with a degree of polymerization p3 and
vii. (M3)$_{p3}$ is soluble or mostly soluble in the reference liquid of interest and
viii. m is the number of (M3)$_{p3}$ (co)polymer arms covalently attached to the core, and
ix. s is the average number of (M1)$_{p3}$ (co)polymer arms covalently attached to the core.

In an embodiment, the polymer composition, the number of arms on any particular star varies across the population of star macromolecules in each composition, due to the synthetic process used for the synthesis of the composition. This process is called "arm first" method and is described in details herein below. Due to variation in the number of arms in star macromolecules, the number of arms n, m and s are referred as an average number of arms.

Star macromolecules with a single peak in the GPC curve with a polydispersity index (PDI) above 1.0 and below 2.5 is preferred.

As used herein, the term "reference liquid of interest" means the liquid to which the polymer composition will be added. Suitable examples of reference liquids include, but are not limited to, water, oil or mixture thereof or water with additives which include but are not limited to; surfactants, oils, fats and waxes, emulsifiers, silicone compounds, UV protectors, antioxidants, various water soluble substances, biogenic agents, deodorants, odor absorbers, antiperspirants, and germ and enzyme inhibitors. Such agents are disclosed in U.S. Pat. Nos. 6,663,855 and 7,318,929 and are herein incorporated by reference to provide definitions for those terms.

Arms of a star can possess the same composition or be different (e.g. star macromolecule with formula (1) vs. (2) or (3), these star are shown in FIG. 1). The difference can be in composition or molecular weight or both (e.g. different monomer units M1, M2, M3 and/or different degree of polymerization p1, p2, p3).

Term "(co)polymer" is defined as a polymer derived from two (or more) monomeric species (monomer units)

More preferred specific monomer units as a building blocks of M1, M2, M3 and My include those selected from protected and unprotected acrylic acid, methacrylic acid, ethacrylic acid, methyl acrylate, ethyl acrylate, .alpha.-butyl acrylate, iso-butyl acrylate, t-butyl acrylate, 2-ethylhexyl acrylate, decyl acrylate, octyl acrylate, methyl methacrylate, ethyl methacrylate, n-butyl methacrylate, iso-butyl methacrylate, t-butyl methacrylate, 2-ethylhexyl methacrylate, decyl methacrylate, methyl ethacrylate, ethyl ethacrylate, n-butyl ethacrylate, iso-butyl ethacrylate, t-butyl ethacrylate, 2-ethylhexyl ethacrylate, decyl ethacrylate, 2,3-dihydroxypropyl acrylate, 2,3-dihydroxypropyl methacrylate, 2-hydroxyethyl acrylate, 2-hydroxypropyl acrylate, hydroxypropyl methacrylate, glyceryl monoacrylate, glyceryl monoethacrylate, glycidyl methacrylate, glycidyl acrylate, acrylamide, methacrylamide, ethacrylamide, N-methyl acrylamide, N,N-dimethyl acrylamide, N,N-dimethyl methacrylamide, N-ethyl acrylamide, N-isopropyl acrylamide, N-butyl acrylamide, N-t-butyl acrylamide, N,N-di-n-butyl acrylamide, N,N-diethylacrylamide, N-octyl acrylamide, N-octadecyl acrylamide, N,N-diethylacrylamide, N-phenyl acrylamide, N-methyl methacrylamide, N-ethyl methacrylamide, N-dodecyl methacrylamide, N,N-dimethylaminoethyl acrylamide, quaternised N,N-dimethylaminoethyl acrylamide, N,N-dimethylaminoethyl methacrylamide, quaternised N,N-dimethylaminoethyl methacrylamide, N,N-dimethylaminoethyl acrylate, N,N-dimethylaminoethyl methacrylate, quaternised N,N-dimethyl-aminoethyl acrylate, quaternised N,N-dimethylaminoethyl methacrylate, 2-hydroxyethyl acrylate, 2-hydroxyethyl methacrylate, 2-hydroxyethyl ethacrylate, glyceryl acrylate, 2-methoxyethyl acrylate, 2-methoxyethyl methacrylate, 2-methoxyethyl ethacrylate, 2-ethoxyethyl acrylate, 2-ethoxyethyl methacrylate, 2-ethoxyethyl ethacrylate, maleic acid, maleic anhydride and its half esters, fumaric acid, itaconic acid, itaconic anhydride and its half esters, crotonic acid, angelic acid, diallyldimethyl ammonium chloride, vinyl pyrrolidone vinyl imidazole, methyl vinyl ether, methyl vinyl ketone, maleimide, vinyl pyridine, vinyl pyridine-N-oxide, vinyl furan, styrene sulphonic acid and its salts, allyl alcohol, allyl citrate, allyl tartrate, vinyl acetate, vinyl alcohol, vinyl caprolactam, vinyl acetamide, vinyl formamide and mixtures thereof.

Even more preferred monomer units as a building parts of M1, M2, M3 and My are those selected from methyl acrylate, methyl methacrylate, .methyl ethacrylate, ethyl acrylate, ethyl methacrylate, ethyl ethacrylate, n-butyl acrylate, n-butyl methacrylate, n-butyl ethacrylate, 2-ethylhexyl acrylate, 2-ethylhexyl methacrylate, 2-ethylhexyl ethacrylate, N-octyl acrylamide, 2-methoxyethyl acrylate, 2-hydroxyethyl acrylate, N,N-dimethylaminoethyl acrylate, N,N-dimethylaminoethyl methacrylate, acrylic acid, methacrylic acid, N-t-butylacrylamide, N-sec-butylacrylamide, N,N-dimethylacrylamide, N,N-dibutylacrylamide, N,N-dihydroxyethyllacrylamide 2-hydroxyethyl acrylate, 2-hydroxyethyl methacrylate, benzyl acrylate, 4-butoxycarbonylphenyl acrylate, butyl acrylate, 4-cyanobutyl acrylate, cyclohexyl acrylate, dodecyl acrylate, 2-ethylhexyl acrylate, heptyl acrylate, iso-butyl acrylate, 3-methoxybutyl acrylate, 3-methoxypropyl acrylate, methyl acrylate, N-butyl acrylamide, N,N-dibutyl acrylamide, ethyl acrylate, methoxyethyl acrylate, hydroxyethyl acrylate, diethyleneglycolethyl acrylate, styrene (optionally substituted with one or more $C_1$-$C_{12}$ straight or branched chain alkyl groups), alpha-methylstyrene, t-butylstyrene, p-methylstyrene, and mixtures thereof.

Monomer units within the arms may be connected with C—C covalent bonds. This is believed to make them hard to degrade so that the star macromolecule may perform as efficient thickening agent in a harsh environment (very high/low pH or in the presence of strong oxidizing agents).

When "C" represents the crosslinked core of the star macromolecule it may be comprised of crosslinker (Mx), crosslinker (Mx) and monomer (My), crosslinker (Mx) and (M2), or a mixture of (Mx), (My) and (M2).

Suitable crosslinkers (Mx) encompass all of the compounds which are capable, under the polymerization conditions, of bringing about crosslinking. These include but are not limited di-, tri-, tetra-functional (meth)acrylates, di-, tri- and tetra-functional styrenes and other multi- or poly-functional crosslinkers.

Some examples of the crosslinking agents may include but are not limited to 1,2-divinylbenzene, 1,3-divinylbenzene and 1,4-divinylbenzene, 1,2-ethanediol di(meth)acrylate, 1,3-propanediol di(meth)acrylate, 1,4butanediol di(meth)acrylate, 1,5-hexanediol di(meth)acrylate, divinylbenzene, ethyleneglycol di(meth)acrylate, propyleneglycol di(meth)acrylate, butyleneglycol di(meth)acrylate, triethyleneglycol di(meth)acrylate, polyethyleneglycol di(meth)acrylate, polypropyleneglycol di(meth)acrylate, polybutyleneglycol di(meth)acrylate, and allyl(meth)acrylate, glycerol di(meth)acrylate, trimethylolpropane tri(meth)acrylate, pentaerythritol tetra(meth)acrylate, allyl methacrylate, allyl acrylate.

The terms 'mostly soluble', 'not fully soluble', and 'not soluble' are used to describe the extent which a composition which is capable of being dissolved in a reference liquid of interest.

The term 'mostly soluble' is used to describe a composition which is capable dissolves completely with exception of a slight cloudiness in the reference liquid of interest. The term 'not fully soluble' is used to describe a composition which disperses with a cloudiness in the reference liquid of interest. The term 'not soluble' is used to describe a composition which does not disperse and remains as a solid in the reference liquid of interest. A list of solvents and non-solvent for polymers can be found in "Polymer Handbook, $4^{th}$ Ed." edited by Brandrup J.; Immergut, Edmund H.; Grulke, Eric A.; Abe, Akihiro; Bloch, Daniel R., John Wiley & Sons: 2005.

Multi-arm stars macromolecules are the preferred topology for an embodiment of the present invention as they can adopt a globular shape wherein the inner segment, $(M2)_{p2}$ of each arm covalently attached to the core, can chain extend in a selected solvent to attain a highly swollen stable structure. The dispersant medium can be water, oil or mixture thereof. The degree of polymerization p2 of the segment (M2), should be higher than that of p1 of segment (M1) to attain a highly swollen stable structure. A star macromolecule with $p2>(3 \times p1)$ is more preferred.

In one embodiment, a star macromolecule described with formula (2) and shown in FIG. 1B, comprising a fraction of segmented (co)polymer arms $[F-(M1)_{p1}-(M2)_{p2}]$, the average number of arms, n, should be greater than two per star, preferentially greater than three, and can comprise a mole fraction between 0.5 and 100% of the arms in the average star macromolecule. The ratio of n to m is more preferably between 100 and 0.1.

In one embodiment, in a star macromolecule described with formula (3) and shown in FIG. 1C comprising a fraction of arms $[F-(M1)_{p1}]$ the average number of arms, o, should be greater than two per star, preferentially greater than three, and can comprise a mole fraction between 0.5 and 100% of the arms in the average star macromolecule. The ratio of o to m is more preferably between 100 and 0.1.

An embodiment of the present invention can be exemplified by a multi-arm star macromolecule wherein the average number of arms in the star macromolecule is between 5 and 500, preferentially between 10 and 250.

In one embodiment, the star macromolecule has a core which contains additional functionality and/or expanded free volume. 'Expended free volume' of the core is defined as the core with lower crosslink density. The free volume in the core is generated when during the crosslinking process crosslinker Mx with monomer M2 or My is used. If M2 or My are monomers with functional groups, these groups will be incorporated in the core.

In one embodiment, the star macromolecule may store and release in controlled rate the small molecules. 'Small molecules' are fragrances, UV absorbers, vitamins, minerals, dyes, pigments, solvents, surfactants, metal ions, salts, oils, or drugs. These small molecules can be stored inside the core of the star macromolecule and next released. Each small molecule has some affinity to the core, is soluble in the core environment. Higher affinity of the small molecule to the core will result in the lower rate of release from star macromolecule. The affinity may be increased or decreased through non-covalent forces including H-bonding, electrostatic, hydrophobic, coordination and metal chelating interactions.

In one embodiment, the star macromolecule displays shear thinning behavior. 'Shear thinning' is defined as is an effect where viscosity decreases with increasing rate of shear stress. The extent of shear thinning behavior is characterized using a Brookfield-type viscometer where viscosities are measured under different shear rates.

In one embodiment, the star macromolecule comprises a functional group which exhibits H-bonding, coordination, hydrophobic, metal chelating and/or electrostatic forces. "F" represents an optionally functional group or mixture of functional groups present on the arm chain-end. Functional groups (F) encompass all of the compounds capable of interacting through non-covalent forces including H-bonding, electrostatic, hydrophobic, coordination and metal chelating.

Some examples of F end groups capable of H-bonding include but are not limited to modified bases adenine, thymine, guanine, cytosine, or derivatives thereof, peptides etc. Some examples of endgroups capable of electrostatic interactions include but are not limited to carboxylate, phosphate, sulfonate, secondary-, tertiary- and quaternary-amines. Some examples of endgroups capable of hydrophobic interactions include but are not limited to C1-C30 aliphatic groups, benzyl and aliphatic benzyl groups, saturated and unsaturated hydrophobes. Some examples of endgroups capable of coordination interactions include but are not limited to metal ions and/or metal ion ligands. Some examples of endgroups capable of metal chelating interactions include derivatives of diethylenetriamine-N,N,N',N',N"-pentaacetic acid (DTA), ethylenedinitrilotetraacetic acid (EDTA), or nitrilotriacetic acid (NTA).

In one embodiment, the star macromolecule comprises a functional group F which is designed to interact with small molecule surfactant micelles. 'Interacts with' is defined as any intermolecular force between two molecules. These intermolecular forces include electrostatic, hydrogen bonding, hydrophobic, steric, dipole-dipole, pi-pi, or other intermolecular forces.

Surfactants represent a class of molecules with a hydrophobic tail and a hydrophilic head. Some examples of surfactants include but are not limited to linear alkylbenzenesulfonate salts (LAS), alkyl ether sulfate salts (AEOS), alkylpolyglycosides (APG), alcohol ethoxylates, fatty acid glucoamides, betaines, alpha-olefinsulfonate salts, polysorbates, PEGs, alkylphenol ethoxylates, esterquats, imidizolium salts, diamido quaternary ammonium salts, etc.

In one embodiment, the star macromolecule arms comprise a (co)polymer segment that exhibits an upper, or higher, critical solution temperature (UCST or HCST) whereby the star macromolecule is soluble in a liquid at higher temperature, say above 44° C., then at the lower use temperature the outer shell polymer segments become insoluble and self assemble to form a shear sensitive gel or in another embodiment the invention the outer shell of the star macromolecule arms comprise a (co)polymer segment that exhibits a lower critical solution temperature (LCST), say 5° C., whereby the star macromolecule is soluble in a liquid at lower temperature then at the use temperature the outer shell polymer segments become insoluble and self assemble to form a shear sensitive gel. In the case of a LCST it is envisioned that a copolymer segment with an LCST below 10° C., preferable below 5° C. would be optimal. A non-limiting example would be a copolymerization of BuMA and DMAEMA and preparation of copolymers with designed LCST. A copolymer with 10% BuMA has a LCST close to 0° C. and one would use less BuMA or a less hydrophobic monomer such as MMA to increase the LCST to ~5° C. Indeed the Tg of the segment of the star can be selected to allow dissolution of the star in room temperature aqueous media.

In one embodiment, a star macromolecule further comprise a personal care and cosmetics formulation and/or product. Personal care and cosmetic products include but are not limited to a shampoo, conditioner, hair lotion, tonic, hair spray, hair mousse, hair gel, hair dyes, moisturizer, suntan lotion, color cosmetic, body lotion, hand cream, baby skincare product, facial cream, lipstick, mascara, blush, eyeliner, baby shampoo, baby moisturizer, baby lotion, shower gel, soap, shaving product, deodorant, bath cream, body wash, serum, cream, solid, gel, lubricant, gelly, balm, tooth paste, whitening gel, disposable towel, disposable wipe or ointment.

In one embodiment a star macromolecule further comprise a home care formulation and/or product. Home care products include but are not limited to a surface cleaner, window cleaner, laundry detergent, toilet cleaner, fabric cleaner, fabric softener, dish detergent, cleaning stick, stain stick, spray cleaners, sprayable formulations, lubricant, disposable towel or disposable wipe.

The polymer chains that comprise the arms are preferably provided with a molecular mass of greater than or equal to 500 which can range up to 2,000,000. This numbers correspond to p1, p2, p3 in the range of 5 up to 20,000 preferably in the range of 8 to 2,000.

In one example, the star macromolecules comprising segmented copolymers arms are directed at use in aqueous media. The stars comprise a crosslinked core, and arms comprising of water soluble copolymer $(M2)_{p2}$ and a hydrophobic (co)polymer $(M1)_{p1}$. Therefore in a in a non-limiting example the stars comprise a crosslinked core, and arms comprising an water soluble (co)polymer (e.g. poly(acrylic acid), poly(2-hydroxyethyl acrylate), poly(N-isopropylacrylamide), poly(ethylene glycol) methacrylate, quaternized poly(dimethylaminoethyl methacrylate), etc.) and a hydrophobic (co)polymer (e.g. polystyrene or substituted polystyrenes, poly(alkyl(meth)acrylate), etc.) or a hydrocarbon based segment. Suitable hydrocarbon based segments can comprise low molecular weight α-olefin. Lower molecular weight α-olefins are commercially available and higher molecular weight species can be prepared by telomerization of ethylene or ethylene propylene mixtures. [Kaneyoshi, H.; Inoue, Y.; Matyjaszewski, K. Macromolecules 2005, 38, 5425-5435.]

In an embodiment, the polymer compositions can self assemble in solution to provide a certain level of control over viscosity and consistency factors in many aqueous and oil based systems where control over the rheology is a concern. Applications include; water- and solvent-based coating compositions, paints, inks, antifoaming agents, antifreeze substances, corrosion inhibitors, detergents, oil-well drilling-fluid rheology modifiers, additives to improve water flooding during enhanced oil recovery, dental impression materials, cosmetic and personal care applications including hair styling, hair conditioners, shampoos, bath preparations, cosmetic creams, gels, lotions, ointments, deodorants, powders, skin cleansers, skin conditioners, skin emollients, skin moisturizers, skin wipes, sunscreens, shaving preparations, and fabric softeners, with the rheology modifier providing characteristics of high gel strength, highly shear thinning characteristics, forms versatile low viscosity soluble concentrations, and synergistic interactions with added agents to adjust their rheology profile to optimize properties such as sedimentation, flow and leveling, sagging, spattering, etc.

One non-limiting field of applications that can exemplify the utility of the disclosed star macromolecules is cosmetic and personal care compositions such as hair styling sprays, mousses, gels and shampoos, frequently contain resins, gums and adhesive polymers to provide a variety of benefits, for example, film-forming ability, thickening, sensory properties and hair shaping and setting. Polymers designed for rheological control, as thickening agents, in such compositions generally focus on linear or graft copolymers which contain various monomers in an alternating, random or block configuration.

Suitable hydrophobic monomers that may be used to form an arm or segment of an arm, such as a polymeric segment of an arm, of a star macromolecule may include, but is not limited to methyl acrylate, ethyl acrylate, n-butyl acrylate, iso-butyl acrylate, t-butyl acrylate, 2-ethylhexyl acrylate, decyl acrylate, octyl acrylate; methyl methacrylate; ethyl methacrylate; n-butyl methacrylate; iso-butyl methacrylate; t-butyl methacrylate; 2-ethylhexyl methacrylate; decyl methacrylate; methyl ethacrylate; ethyl ethacrylate; n-butyl ethacrylate; iso-butyl ethacrylate; t-butyl ethacrylate; 2-ethylhexyl ethacrylate; decyl ethacrylate; 2,3-dihydroxypropyl acrylate; 2,3-dihydroxypropyl methacrylate; 2-hydroxypropyl acrylate; hydroxypropyl methacrylate; glycidyl methacrylate; glycidyl acrylate, acrylamides, styrene; styrene optionally substituted with one or more C1-C12 straight or branched chain alkyl groups; or alkylacrylate. For example, the hydrophobic monomer may comprise styrene; alpha-methylstyrene; t-butylstyrene; p-methylstyrene; methyl methacrylate; or t-butyl-acrylate. For example, the hydrophobic monomer may comprise styrene. In certain embodiments, the hydrophobic monomer may comprise a protected functional group.

Suitable hydrophilic monomers that may be used to form an arm or segment of an arm, such as a polymeric segment of an arm, of a star macromolecule may include, but is not limited to, protected and unprotected acrylic acid, such as methacrylic acid, ethacrylic acid, methyl acrylate, ethyl acrylate, á-butyl acrylate, iso-butyl acrylate, t-butyl acrylate, 2-ethylhexyl acrylate, decyl acrylate, octyl acrylate; methyl methacrylate; ethyl methacrylate; n-butyl methacrylate; iso-butyl methacrylate; t-butyl methacrylate; 2-ethylhexyl methacrylate; decyl methacrylate; methyl ethacrylate; ethyl ethacrylate; n-butyl ethacrylate; iso-butyl ethacrylate; t-butyl ethacrylate; 2-ethylhexyl ethacrylate; decyl ethacrylate; 2,3-dihydroxypropyl acrylate; 2,3-dihydroxypropyl methacrylate; 2-hydroxyethyl acrylate; 2-hydroxypropyl acrylate; hydroxypropyl methacrylate; glyceryl monoacrylate; glyceryl monoethacrylate; glycidyl methacrylate; glycidyl acrylate; acrylamide; methacrylamide; ethacrylamide; N-methyl acrylamide; N,N-dimethyl acrylamide; N,N-dimethyl methacrylamide; N-ethyl acrylamide; N-isopropyl acrylamide; N-butyl acrylamide; N-t-butyl acrylamide; N,N-di-n-butyl acrylamide; N,N-diethylacrylamide; N-octyl acrylamide; N-octadecyl acrylamide; N,N-diethylacrylamide; N-phenyl acrylamide; N-methyl methacrylamide; N-ethyl methacrylamide; N-dodecyl methacrylamide; N,N-dimethylaminoethyl acrylamide; quaternised N,N-dimethyl-aminoethyl acrylamide; N,N-dimethylaminoethyl methacrylamide; quaternised N,N-dimethylaminoethyl methacrylamide; N,N-dimethylaminoethyl acrylate; N,N-dimethylaminoethyl methacrylate; quaternised N,N-dimethyl-aminoethyl acrylate; quaternised N,N-dimethylamino-ethyl methacrylate; 2-hydroxyethyl acrylate; 2-hydroxyethyl methacrylate; 2-hydroxyethyl ethacrylate; glyceryl acrylate; 2-methoxyethyl acrylate; 2-methoxyethyl methacrylate; 2-methoxyethyl ethacrylate; 2-ethoxyethyl acrylate; 2-ethoxyethyl methacrylate; 2-ethoxyethyl ethacrylate; maleic acid; maleic anhydride and its half esters; fumaric acid; itaconic acid; itaconic anhydride and its half esters; crotonic acid; angelic acid; diallyldimethyl ammonium chloride; vinyl pyrrolidone vinyl imidazole; methyl vinyl ether; methyl vinyl ketone; maleimide; vinyl pyridine; vinyl pyridine-N-oxide; vinyl furan; styrene sulphonic acid and its salts; allyl alcohol; allyl citrate; allyl tartrate; vinyl acetate; vinyl alcohol; vinyl caprolactam; vinyl acetamide; or vinyl formamide. For example, the hydrophilic monomer may comprise protected and unprotected acrylic acid, such as methacrylic acid, ethacrylic acid, methyl acrylate, ethyl acrylate, á-butyl acrylate, iso-butyl acrylate, t-butyl acrylate, 2-ethylhexyl acrylate, decyl acrylate, octyl acrylate; methyl acrylate; methyl methacrylate; methyl ethacrylate; ethyl acrylate; ethyl methacrylate; ethyl ethacrylate; n-butyl acrylate; n-butyl methacrylate; n-butyl ethacrylate; 2-ethylhexyl acrylate; 2-ethylhexyl methacrylate; 2-ethylhexyl ethacrylate; N-octyl acrylamide; 2-methoxyethyl acrylate; 2-hydroxyethyl acrylate; N,N-dimethylaminoethyl acrylate; N,N-dimethylaminoethyl methacrylate; acrylic acid; methacrylic acid; N-t-butylacrylamide; N-sec-butylacrylamide; N,N-dimethylacrylamide; N,N-dibutylacrylamide; N,N-dihydroxyethyllacrylamide; 2-hydroxyethyl acrylate; 2-hydroxyethyl methacrylate; benzyl acrylate; 4-butoxycarbonylphenyl acrylate; butyl acrylate; 4-cyanobutyl acrylate; cyclohexyl acrylate; dodecyl acrylate; 2-ethylhexyl acrylate; heptyl acrylate; iso-butyl acrylate; 3-methoxybutyl acrylate; 3-methoxypropyl acrylate; methyl acrylate; N-butyl acrylamide; N,N-dibutyl acrylamide; ethyl acrylate; methoxyethyl acrylate; hydroxyethyl acrylate; or diethyleneglycolethyl acrylate. For example, the hydrophilic monomer may comprise protected and unprotected acrylic acid, such as methacrylic acid, ethacrylic acid, methyl acrylate, ethyl acrylate, α-butyl acrylate, iso-butyl acrylate, t-butyl acrylate, 2-ethylhexyl acrylate, decyl acrylate, octyl acrylate; 2-hydroxyethyl acrylate; N-isopropylacrylamide; ethylene glycol methacrylate; (polyethylene glycol) methacrylate; or quaternized dimethylaminoethyl methacrylate. For example, the hydrophilic monomer may comprise acrylic acid, methacrylic acid, 2-hydroxyethyl acrylate, acrylamide, vinyl pyrrolidone, vinyl pyridine, styrene sulphonic acid, PEG-methacrylate, 2-(dimethylamino) ethyl methacrylate, 2-(trimethylamino)ethyl methacrylate, 2-acrylamido-2-methylpropane sulphonic acid. For example, the hydrophilic monomer may comprise acrylic acid.

Suitable monomers that may be used to form a core of a star macromolecule may include, but are not limited to, a multifunctional monomer, for example, a hexafunctional monomer, a pentafunctional monomer, a tetrafunctional monomer, a trifunctional monomer, or a difunctional monomer. For example, a crosslinker may be a hydrophobic monomer or a hydrophilic monomer, such as a hydrophobic multifunctional monomer or a hydrophilic multifunctional monomer, for example, a hydrophobic difunctional monomer or a hydrophilic difunctional monomer. For example, the crosslinker may be a hydrophobic crosslinker, including, but not limited to, 1,2-divinylbenzene; 1,3-divinylbenzene; 1,4-divinylbenzene; 1,2-ethanediol di(meth)acrylate; 1,3-propanediol di(meth)acrylate; 1,4butanediol di(meth)acrylate; 1,5-hexanediol di(meth)acrylate; divinylbenzene; ethyleneglycol di(meth)acrylate; di(ethylene glycol) diacrylate (DEGlyDA); propyleneglycol di(meth)acrylate; butyleneglycol di(meth)acrylate; triethyleneglycol di(meth)acrylate; polyethyleneglycol di(meth)acrylate; polypropyleneglycol di(meth)acrylate; polybutyleneglycol di(meth)acrylate; allyl(meth)acrylate; glycerol di(meth)acrylate; trimethylolpropane tri(meth)acrylate; pentaerythritol tetra (meth)acrylate; allyl methacrylate; or allyl acrylate. For example, the crosslinker may be di(ethylene glycol) diacrylate (DEGlyDA) or divinylbenzene. For example, the crosslinker may be divinylbenzene.

Suitable star macromolecules may include, but are not limited to, a mikto star macromolecule, a water-soluble star macromolecule, a gel-forming star macromolecule, emulsifier/thickening agent star macromolecules or combinations thereof. In certain embodiments, the star macromolecule may have a molecular weight of greater than 100,000 g/mol, for example, between 100,000 g/mol and 2,000,000 g/mol, such as between 125,000 g/mol and 1,750,000 g/mol; between 150,000 g/mol and 1,750,000 g/mol; between 200,000 g/mol and 1,500,000 g/mol; between 225,000 g/mol and 1,250,000 g/mol; between 125,000 g/mol and 1,000,000 g/mol; between 125,000 g/mol and 900,000 g/mol; between 125,000 g/mol and 800,000 g/mol; between 125,000 g/mol and 700,000 g/mol; between 150,000 g/mol and 650,000 g/mol; between 200,000 g/mol and 600,000 g/mol; between 225,000 g/mol and 650,000 g/mol; between 250,000 g/mol and 550,000 g/mol; between 350,000 g/mol and 500,000 g/mol; between 300,000 g/mol and 500,000 g/mol; or between 350,000 g/mol and 750,000 g/mol.

Suitable star macromolecules may have a polydispersity index (PDI) of less than 2.5, for example, a PDI of less than 2.0, such as less than 1.7. For example, a star macromolecule may have a PDI of between 1.0 to 2.5, such as between 1.0 and 2.3; between 1.0 and 2.0; between 1.0 and 1.9; between 1.0 and 1.8; between 1.0 and 1.7; between 1.0 and 1.6; between 1.0 and 1.5; between 1.0 and 1.4; between 1.0 and 1.3; between 1.0 and 1.2; between 1.0 and 1.1; between 1.05 and 1.75; between 1.1 and 1.7; between 1.15 and 1.65; or between 1.15 and 1.55.

Suitable star macromolecules may comprise arms that are of the same type or a different type and are homopolymeric, copolymeric, comprise multiple block segment, random segments, gradient segments and or no particular segments. In certain embodiments, the star macromolecule may comprise, for example, one or more arm-types, such as, two or more, three or more, four or more, or five or more arm-types. Suitable arm types may include, but are not limited to, homopolymeric arms, copolymeric arms, such as random copolymeric arms or block copolymeric arms, or combinations thereof. For example, a star macromolecule may comprise homopolymeric arms and copolymeric arms, such as block copolymeric arms. Suitable arm types may also include, but are not limited to, hydrophilic arms, hydrophobic arms, or amphiphilic arms. In certain embodiments, a star macromolecule arm may comprise hydrophilic polymeric segments comprising hydrophilic monomeric residues, hydrophobic polymeric segments comprising hydrophobic monomeric residues, amphiphilic polymeric segments comprising amphiphilic monomeric residues, or combinations thereof. For example, in certain embodiments, a star macromolecule may comprise homopolymeric arms and copolymeric arms, such as hydrophilic homopolymeric arms and copolymeric arms comprising hydrophilic polymeric segments and hydrophobic polymeric segments.

Suitable star macromolecules may also comprise arms that are covalently linked to the core of the star macromolecule. In certain embodiments, the arms of a star macromolecule may be covalently linked to the core of the star macromolecule via crosslinking, such as crosslinking with a crosslinker, for example, a hydrophobic difunctional crosslinker or a hydrophilic difunctional crosslinker. For example, arms of a star macromolecule, such as homopolymeric arms and block copolymeric arms of a mikto star macromolecule, may be covalently linked together to form a core by crosslinking an end of the arms with a crosslinker, such as with a hydrophobic difunctional crosslinker or a hydrophilic difunctional crosslinker.

Suitable star macromolecules may also comprise arms of varying length and/or degree of polymerization. In certain embodiments, for example, a star macromolecule may comprise homopolymeric arms and block copolymeric arms, wherein the homopolymeric arms of a shorter length and/or a lesser degree of polymerization in relation to the block copolymeric arms. In certain embodiments, for example, a star macromolecule may comprise homopolymeric arms and block copolymeric arms, wherein the block copolymeric arms of a longer length and/or a greater degree of polymerization in relation to the homopolymeric arms. In certain embodiments, a star macromolecule may comprise hydrophilic homopolymeric arms and block copolymeric arms, comprising hydrophobic polymeric segments distal to the star core and hydrophilic polymeric segments that are proximal to the core of the star, wherein a distal portion of the hydrophilic polymeric segments of the copolymeric arm extends beyond a distal portion of the hydrophilic homopolymeric arms. For example, a star macromolecule may comprise hydrophilic homopolymeric arms comprising polymerized hydrophilic monomeric residues and block copolymeric arms comprising hydrophobic polymeric segments distal to the core of the star and hydrophilic polymeric segments that are proximal to the core of the star, wherein the distal hydrophobic polymeric segments extend beyond the most distal portion, in relation to the core, of the hydrophilic homopolymeric arms, and/or wherein a distal portion of the proximal hydrophilic polymeric segments of the copolymeric arm extend beyond the most distal portion, in relation to the core, of the hydrophilic homopolymeric arms. In certain embodiments, a star macromolecule may comprise hydrophilic homopolymeric arms and block copolymeric arms, comprising hydrophobic polymeric segments distal to the star core and hydrophilic polymeric segments that are proximal to the star core, wherein the degree of polymerization of the hydrophilic polymeric segments of the copolymeric arm is greater than, for example, 20% greater than, such as between 30% to 300% greater than, between 40% to 250%, between 50% to 200%, or between 75% to 250% greater than, the degree of polymerization of the hydrophilic homopolymeric arms, such that a distal portion of the hydrophilic polymeric segments of the copolymeric arm extends beyond the a distal portion of the hydrophilic homopolymeric arms.

In certain embodiments, a star macromolecule may comprise hydrophilic homopolymeric arms comprising polymerized hydrophilic monomeric residues and block copolymeric arms comprising hydrophobic polymeric segments distal to the core of the star and hydrophilic polymeric segments proximal to the core of the star, wherein the polymerized hydrophilic monomeric residues of the homopolymeric arm and the hydrophilic polymeric segments of the copolymeric arm may be derived from the same hydrophilic monomers, and may have the same or different degree of polymerization, for example, a degree of polymerization of between 50 to 500 monomeric residues, such as, between 50 to 400 monomeric residues; between 50 to 300 monomeric residues; between 50 to 200 monomeric residues; between 100 to 250 monomeric residues; between 125 to 175 monomeric residues; or between 150 to 300 monomeric residues. For example, a star macromolecule may comprise hydrophilic homopolymeric arms comprising polymerized hydrophilic monomeric residues and block copolymeric arms comprising hydrophobic polymeric segments distal to the core of the star and hydrophilic polymeric segments proximal to the core of the star, wherein the polymerized hydrophilic monomeric residues of the homopolymeric arm and the hydrophilic polymeric segments of the copolymeric arm may be derived from the same hydrophilic monomers, and may have the same degree of polymerization, and wherein the hydrophilic polymeric segments of the copolymeric arm may have a degree of polymerization of between 1 to 60 monomeric residues, such as between 1 to 50 monomeric residues; between 1 to 45 monomeric residues; between 5 to 40 monomeric residues; between 8 to 35 monomeric residues; between 10 to 30 monomeric residues; between 12 to 25 monomeric residues; between 14 to 20 monomeric residues; between 15 to 30 monomeric residues; or between 5 to 20 monomeric residues.

Suitable star macromolecules may have a wide range of total number of arms, for example, a star macromolecule may comprise greater than 15 arms. For example, a suitable star macromolecule may comprise between 15 and 100 arms, such as between 15 and 90 arms; between 15 and 80 arms; between 15 and 70 arms; between 15 and 60 arms; between 15 and 50 arms; between 20 and 50 arms; between 25 and 45 arms; between 25 and 35 arms; between 30 and 45 arms; or between 30 and 50 arms.

Suitable star macromolecules may have more than one arm type, such as two or more different arm types, where in a molar ratio of the different arm types may be between 20:1 and 1:1. For example, a star macromolecule comprising two different arm types, such as a homopolymeric arm, for example, a hydrophilic homopolymeric arm, and a copolymeric arm, for example, a copolymeric arm comprising hydrophilic polymeric segments and hydrophobic polymeric segments, may have a molar ratio of the two different arm types between 20:1 to 2:1, such as between 15:1 to 2:1; between 10:1 to 2:1; between 9:1 to 2:1; between 8:1 to 2:1; between 7:1 to 2:1; between 6:1 to 2:1; between 5:1 to 2:1; between 4:1 to 2:1; between 3:1 to 2:1; between 2:1 to 1:1; between 8:1 to 3:1; between 7:1 to 2:1; or between 5:1 to 3:1.

Suitable star macromolecules may include, but is not limited to, comprising arms having a molecular weight of greater than 10,000 g/mol. For example, a star macromolecule may comprise arms having a molecular weight of between 10,000 g/mol and 200,000 g/mol, such as between 10,000 g/mol and 175,000 g/mol; between 10,000 g/mol and 150,000 g/mol; between 10,000 g/mol and 125,000 g/mol; between 10,000 g/mol and 100,000 g/mol; between 10,000 g/mol and 90,000 g/mol; between 10,000 g/mol and 80,000 g/mol; between 10,000 g/mol and 70,000 g/mol; between 60,000 g/mol and 50,000 g/mol; between 10,000 g/mol and 40,000 g/mol; between 10,000 g/mol and 30,000 g/mol; between 10,000 g/mol and 20,000 g/mol; between 20,000 g/mol and 175,000 g/mol; between 20,000 g/mol and 100,000 g/mol; between 20,000 g/mol and 75,000 g/mol; between 20,000 g/mol and 50,000 g/mol; between 15,000 g/mol and 45,000 g/mol; or between 15,000 g/mol and 30,000 g/mol.

Suitable arms of a star macromolecule may include, but is not limited to, arms having an HLB value of at least 17 (wherein the HLB is calculated per the formula set forth in the test procedures). For example, suitable arms of a star macromolecule may have an HLB value of greater than 17.25, such as greater than 18.5; at least 19; between 17.5 to 20; between 17.5 to 19.5; between 18 to 20; between 18.5 to 20; between 19 to 20; between 19.5 to 20; between 18 to 19.5; between 18.5 to 19.75; between 18.2 to 19.2; or between 18.75 to 19.5.

Suitable hydrophobic polymeric segments of a copolymeric arm of a star macromolecule may include, but is not limited to, hydrophobic polymeric segments having an HLB value of less than 8. For example, suitable hydrophobic polymeric segments may have an HLB value of less than 7, such as less than 6; less than 5; less than 4; less than 3; less than 2; or about 1.

Suitable arms of a star macromolecule may include, but is not limited to, arms having a polydispersity index (PDI) value of less than 2.5. For example, suitable arms of a star macromolecule may have PDI value of less than 2.25, such as less that 2.0; less than 1.7; between 1.0 to 2.5, such as between 1.0 and 2.3; between 1.0 and 2.0; between 1.0 and 1.9; between 1.0 and 1.8; between 1.0 and 1.7; between 1.0 and 1.6; between 1.0 and 1.5; between 1.0 and 1.4; between 1.0 and 1.3; between 1.0 and 1.2; between 1.0 and 1.1; between 1.05 and 1.75; between 1.1 and 1.7; between 1.15 and 1.65; or between 1.15 and 1.55.

Suitable cores of a star macromolecule may be formed by or derived from, but is not limited to, crosslinking of a plurality of arms and a crosslinker. For example, a core may be formed by or derived from crosslinking of a plurality of homopolymeric arms and a plurality of copolymeric arms with a crosslinker, such as a multifunctional monomer crosslinker, for example, a hydrophobic difunctional monomer crosslinker. In certain embodiments, the core may be formed or derived from crosslinking a plurality of hydrophilic homopolymeric arms and a plurality of copolymeric arms, comprising block hydrophilic polymeric segments and block hydrophobic polymeric segments, with a crosslinker, such as a hydrophobic difunctional monomer crosslinker, for example divinylbenzene, wherein the molar ratio of the homopolymeric arms to the copolymeric arms may be between 20:1 to 2:1.

Suitable star macromolecules may include, but is not limited to, comprising a core having a molecular weight of greater than 3,000 g/mol. For example, a star macromolecule may comprise a core having a molecular weight of between 3,000 g/mol and 50,000 g/mol, such as between 3,000 g/mol and 45,000 g/mol; between 3,000 g/mol and 40,000 g/mol; between 3,000 g/mol and 30,000 g/mol; between 3,000 g/mol and 20,000 g/mol; between 3,000 g/mol and 15,000 g/mol; between 5,000 g/mol and 40,000 g/mol; between 6,000 g/mol and 30,000 g/mol; between 7,000 g/mol and 25,000 g/mol; between 8,000 g/mol and 20,000 g/mol; between 5,000 g/mol and 15,000 g/mol; between 7,000 g/mol and 12,000 g/mol; between 5,000 g/mol and 9,000 g/mol; between 8,000 g/mol and 10,000 g/mol; or between 9,000 g/mol and 15,000 g/mol.

Suitable star macromolecules may be used to form a clear, homogeneous gel when dissolved in water at a concentration of at least 0.05 wt. % at a pH of about 7.5 at STP. For example, a star macromolecule may form a clear, homogeneous gel when dissolved in water at a concentration of between 0.05 wt. % to 3 wt. %, such as between 0.1 wt. % to 2.5 wt. %; between 0.1 wt. % to 2 wt. %; between 0.2 wt. % to 2.0 wt. %; between 0.2 wt. % to 1.5 wt. %; between 0.2 wt. % to 1.0 wt. %; between 0.2 wt. % to 2.5 wt. %; between 0.3 wt. % to 2.5 wt. %; between 0.4 wt. % to 2.0 wt. %; between 0.5 wt. % to 2.0 wt. %; between 0.6 wt. % to 2.0 wt. %; between 0.7 wt. % to 1.5 wt. %; between 0.8 wt. % to 1.2 wt. %; between 0.9 wt. % to 1.1 wt. %; between 0.5 wt. % to 2.5 wt. %; between 0.75 wt. % to 1.5 wt. %; or between 0.8 wt. % to 1.6 wt. %.

Suitable star macromolecules, in accordance with the pH Efficiency Range Test Procedure described below herein, may be used to form a clear, homogeneous gel, wherein the star macromolecule at a concentration of 0.4 wt. %, may have a viscosity of at least 20,000 cP, at a pH of between about 4 to about 12, for example, at a pH of between about 5 to about 11.5 such as at a pH of between about 5 to about 11; between about 5 to about 10.5; between about 5 to about 10; between about 5 to about 9.5; between about 5 to about 9; between about 5 to about 8.5; between about 5 to about 8; between about 6 to about 11; between about 5.5 to about 10; between about 6 to about 9; between about 6.5 to about 8.5; between about 7 to about 8; between about 7.5 to about 8.5; or between about 6.5 to about 7.5.

In certain embodiments, for example, suitable star macromolecules, in accordance with the pH Efficiency Range Test Procedure described below herein, may be used to form a clear, homogeneous gel, wherein the star macromolecule at a concentration of 0.4 wt. %, may have a viscosity of at least 20,000 cP at a pH between about 5.5 to about 11. For example, at a pH between about 5.5 to about 11 may have a viscosity of at least 30,000 cP, such as, at least 40,000 cP; between 20,000 cP to 250,000 cP; between 20,000 cP to 250,000 cP; between 20,000 cP to 225,000 cP; between 20,000 cP to 200,000 cP; between 20,000 cP to 175,000 cP; between 20,000 cP to 150,000 cP; between 20,000 cP to 125,000 cP; between 30,000 cP to 250,000 cP; between 30,000 cP to 200,000 cP; between 40,000 cP to 175,000 cP; or between 40,000 cP to 150,000 cP. For example, a gel at a pH between about 6 to about 11 may have a viscosity of at least 20,000 cP, such as, at least 30,000 cP; at least 40,000 cP; between 20,000 cP to 250,000 cP; between 20,000 cP to 250,000 cP; between 20,000 cP to 225,000 cP; between 20,000 cP to 200,000 cP; between 20,000 cP to 175,000 cP; between 20,000 cP to 150,000 cP; between 20,000 cP to 125,000 cP; between 30,000 cP to 250,000 cP; between 30,000 cP to 200,000 cP; between 40,000 cP to 175,000 cP; or between 40,000 cP to 150,000 cP. For example, at a pH between about 7 to about 10.5 may have a viscosity of at least 60,000 cP, such as at least 70,000 cP; between 60,000 cP to 250,000 cP; between 60,000 cP to 225,000 cP; between 60,000 cP to 200,000 cP; between 60,000 cP to 175,000 cP; between 60,000 cP to 150,000 cP; between 60,000 cP to 125,000 cP; between 60,000 cP to 115,000 cP; between 60,000 cP to 105,000 cP; or between 60,000 cP to 100,000 cP. For example, at a pH between about 7.5 to about 9.0 may have a viscosity of at least 95,000 cP, such as at least 100,000 cP; between 95,000 cP to 250,000 cP; between 95,000 cP to 225,000 cP; between 95,000 cP to 200,000 cP; between 95,000 cP to 175,000 cP; between 95,000 cP to 150,000 cP; between 95,000 cP to 125,000 cP; between 95,000 cP to 115,000 cP; or between 95,000 cP to 105,000 cP.

Suitable star macromolecules, in accordance with the Dynamic Viscosity & Shear-Thinning Test Procedure described below herein, may be used to form a clear, homogeneous gel, wherein the star macromolecule at a concentration of 0.4 wt. %, may have a viscosity of less than 5,000 cP at a shear rate of 4 sec$^{-1}$, such as a viscosity of less than 4,000 cP. For example, the star macromolecule at a concentration of 0.4 wt. %, may have a viscosity have a viscosity of less than 5,000 cP at a shear rate of 6 sec$^{-1}$, such as a viscosity of less than 4,000 cP or less than 3,000 cP. For example, a gel may have a viscosity of less than 15,000 cP at a shear rate of 0.7 sec$^{-1}$, such as a viscosity of less than 14,000 cP or less than 13,000 cP. Suitable gels may include, but is not limited to, gels having shear-thinning value of at least 5, such as a shear-thinning value of at least 6, or between 5 to 15, such as between 5 to 15; between 7 to 12; between 8 to 10; or between 6 to 13.

Suitable star macromolecules, in accordance with the Dynamic Viscosity & Shear-Thinning Test Procedure described below herein, include those that have a shear-thinning value of at least 15, such as a shear-thinning value of between 15 to 100, such as between 15 to 90; between 20 to 80; between 25 to 70; between 25 to 50; or between 30 to 40.

Suitable star macromolecules, in accordance with the Salt-Induced Break Test Procedure described below herein, include those that have a salt-induced break value of at least 50%, such as a salt-induced break value of between 65% to 100%, such as between 75% to 100%; between 80% to 95%; between 75% to 90%; between 50% to 85%; between 70% to 95%; or between 60% to 100%.

Suitable star macromolecules, in accordance with the pH Efficiency Range Test Procedure described below herein, include those that have a pH-induced break value of at least 15%, such as a pH-induced break value of between 15% to 100%, such as between 25% to 100%; between 30% to 95%; between 40% to 90%; between 50% to 85%; between 70% to 95%; between 80% to 97%; between 90% to 99%; between 95% to 100%; or between 60% to 100%.

Suitable star macromolecules, in accordance with the Dynamic Viscosity & Shear-Thinning Test Procedure described below herein, include those that have a dynamic viscosity value, of greater than 20,000 cP at 1 rpm, and at a concentration of 0.2 wt. %, such as a dynamic viscosity value of greater than 24,000 cP; greater than 28,000 cP; or greater than 30,000 cP at a concentration of 0.2 wt. %.

Suitable emulsions may include, but is not limited to, emulsions that are emulsifier-free and wherein the emulsion is thickened by a star macromolecule. For example, the star macromolecule that may be included in the emulsifier-free emulsion may be a water-soluble star macromolecule, wherein the water-soluble star macromolecule emulsifies the emulsifier-free emulsion.

Suitable star macromolecules, include star macromolecules that have an emulsion value of greater than 60 minutes, for example, greater than 3 hours, such as greater than 6 hours; greater than 10 hours; greater than 20 hours; greater than 40 hours; or greater than 100 hours.

Suitable star macromolecules, according to Formula X, may include star macromolecules wherein P1, P2, and/or P3 comprise hydrophobic monomers, hydrophilic monomers, amphiphilic monomers, or combinations thereof. For example, P1 comprises hydrophobic monomers, P2 comprises hydrophilic monomers, and P3 comprises hydrophilic monomers. For example, star macromolecules, according to Formula X, may include star macromolecules wherein q1 may have a value of between 1 to 100, for example, between 1 to 60, such as, between 1 to 45; between 5 to 40; between 8 to 35; between 10 to 30; between 12 to 25; between 14 to 20; between 15 to 30; or between 5 to 20; and q2 and/or q3 have a value of between 50 to 500, for example, between 50 to 400, such as, between 50 to 300; between 50 to 200; between 100 to 250; between 125 to 175; or between 150 to 300. For example, star macromolecules, according to Formula X, may include star macromolecules wherein r or t, or the sum of r and t, may be greater than 15, such as between 15 and 100; between 15 and 90; between 15 and 80; between 15 and 70; between 15 and 60; between 15 and 50; between 20 and 50; between 25 and 45; between 25 and 35; between 30 and 45; or between 30 and 50. For example, star macromolecules, according to Formula X, may include star macromolecules wherein the molar ratio of r to t is in the range of between 20:1 to 2:1, such as between 15:1 to 2:1; between 10:1 to 2:1; between 9:1 to 2:1; between 8:1 to 2:1; between 7:1 to 2:1; between 6:1 to 2:1; between 5:1 to 2:1; between 4:1 to 2:1; between 3:1 to 2:1; between 2:1 to 1:1; between 8:1 to 3:1; between 7:1 to 2:1; or between 5:1 to 3:1. For example, star macromolecules, according to Formula X, may include star macromolecules wherein the core may be derived from crosslinker monomers, such as hydrophobic crosslinker monomers. For example, star macromolecules, according to Formula X, may include star macromolecules wherein the core may comprise crosslinker monomeric residues, such as hydrophobic crosslinker monomeric residues. For example, star macromolecules, according to Formula X, may include star macromolecules wherein the arm $[(P1)_{q1}\text{-}(P2)_{q}2]_t$ may be homopolymeric or copolymeric, such as block copolymeric.

Suitable star macromolecules, may include, but is not limited to, star macromolecules formed by crosslinking the arms with a crosslinker, such as crosslinking homopolymeric arms and block copolymeric arms with a hydrophobic crosslinker. For example, the homopolymeric arms and the copolymeric arms of a star macromolecule may be covalently attached to the core via crosslinkage with a crosslinker. For example, a core of a prepared star macromolecule may be prepared by crosslinking an end of a homopolymeric arm with an end of a copolymeric arm, such as an end of a hydrophilic homopolymeric arm with a hydrophilic end of a copolymeric arm. For example, the core of a prepared star macromolecules may be formed by crosslinking an ATRP-functional terminal group end of a homopolymeric arm with an ATRP-functional terminal group end of a copolymeric arm.

Suitable initiators that may be used to form the star macromolecules disclosed herein, may include, but is not limited to, nitroxide initiators, such as stable nitroxide initiators, for example, 2,2,6,6-Tetramethylpiperidine-1-oxyl, sometimes called TEMPO; transition metal complexes, such cobalt containing complexes; ATRP initiators, comprising halides, such as, bromide, chloride, or iodide, and transition metal sources, such as, copper, iron, ruthenium transition metal sources; iodide with RCTP catalysts, such as germanium or tin catalysts; RAFT initiators, such as dithioesters, dithiocarbamates, or xanthates; ITP catalysts, comprising iodides; tellurium compounds (e.g., TERP); stibine compounds (e.g., SBRP); or bismuth compounds (e.g., BIRP). For example, in certain embodiments, an initiator may further comprise a monomeric residue, a polymeric segment comprising monomeric residues, or a small-molecule. For example, in certain embodiments, an initiator may comprise an ATRP initiator, wherein the ATRP initiator serves as a terminal functional group. For example, in certain embodiments, an initiator may comprise an ATRP-functional terminal group, comprising an ATRP initiator, such as halides and transition metal sources.

Suitable materials comprising the star macromolecules disclosed herein, include, but is not limited to, lotions, such as cosmetic lotions, personal care lotions, body lotions, emulsifier-free body lotions; serums, such as anti-aging serums; sunscreens, such as SPF 30 sunscreens, SPF 35 sunscreens, SPF 40 sunscreens, SPF 50 sunscreens; creams, such as face-creams, cosmetic creams; hair products, such as shampoos, hair styling products, hair sprays, mousses, hair gels, hair conditioners, bath preparations; gels, such as cosmetic gels or personal care gels; skin application products, such as ointments, deodorants, personal care powders, skin cleansers, skin conditioners, skin emollients, skin moisturizers, skin wipes, shaving preparations; fabric softeners; dental impression materials; or variations thereof.

Suitable materials comprising an emulsifier-free emulsion, wherein the emulsion is thickened by a star macromolecule disclosed herein, may include, but is not limited to, lotions, such as cosmetic lotions, personal care lotions, body lotions, emulsifier-free body lotions; serums, such as anti-aging serums; sunscreens, such as SPF 30 sunscreens, SPF 35 sunscreens, SPF 40 sunscreens, SPF 50 sunscreens; creams, such as face-creams, cosmetic creams; hair products, such as shampoos, hair styling products, hair sprays, mousses, hair gels, hair conditioners, bath preparations; gels, such as cosmetic gels or personal care gels; skin application products, such as ointments, deodorants, personal care powders, skin cleansers, skin conditioners, skin emollients, skin moisturizers, skin wipes, shaving preparations; fabric softeners; dental impression materials; or variations thereof.

In an embodiment, examples of suitable lotion formulations include body lotion formulations, comprising an emulsifier-free emulsion, wherein the emulsion is thickened by a star macromolecule disclosed herein, may include, but is not limited to, formulations comprising one or more of the following: Deionized Water; Disodium EDTA; 1,3-Butylene Glycol; Glycerin; Allantoin; Urea; TEA 99%; Edible Olive Oil (N.F.); Shea Butter; Wickenol 171; Squalane; Crodamol CAP; Crodamol STS; Crodacol C; Tween 20; Lipo GMS 470; PEG 100 Stearate; Cetyl Palmitate; Crodamol PTIS; Crodafos CES; DC 1401; Evening Primrose Oil; Vitamin E Acetate; D-Panthenol; Distinctive HA2; Diocide; or derivatives or combinations thereof.

In an embodiment, examples of suitable lotion formulations include emulsifier-free personal care lotion formulations, comprising an emulsifier-free emulsion, wherein the emulsion is thickened by a star macromolecule disclosed herein, may include, but is not limited to, formulations comprising one or more of the following: Deionized Water; Disodium EDTA; 1,3-Butylene Glycol; Glycerin; Allantoin; Urea; TEA 99%; Edible Olive Oil (N.F.); Wickenol 171; Myritol 318; Squalane; Crodamol PTIS; Isododecane; Evening Primrose Oil; Vitamin E Acetate; D-Panthenol; Distinctive HA2; Diocide; or derivatives or combinations thereof.

In an embodiment, examples of suitable formulations include serum formulations, such as anti-aging serum formulations, comprising an emulsifier-free emulsion, wherein the emulsion is thickened by a star macromolecule disclosed herein, may include, but is not limited to, formulations comprising one or more of the following: Deionized Water; Disodium EDTA; Glycerin; 1,3-Butylene Glycol; Caffeine; Allantoin; Triethanolamine 99%; Crodamol STS; Myritol 318; Wickenol 171; Tween 20; Crodaphos CES; BVOSC; Vitamin E Acetate; Vitamin A Palmitate; Vitamin D3; Gransil IDS; D-Panthenol; DC Upregulex; DC Skin Bright MG; Actiphyte of Japanese Green Tea G; Actiphyte of Grape Seed G; DC Hydroglide; Diocide; or derivatives or combinations thereof.

In an embodiment, suitable formulations include sunscreen formulations, comprising an emulsifier-free emulsion, wherein the emulsion is thickened by a star macromolecule disclosed herein, may include, but is not limited to, formulations comprising one or more of the following: Deionized Water; Disodium EDTA; Glycerin; Triethanolamine 99%; Homomethyl Salicylate; Ethylhexyl Salicylate; Avobenzone; Benzophenone 3; Myritol 318; Lexfeel 7; Octocrylene; Cetyl Alcohol; PEG-15 Cocamine; Lipo GMS 470; Crodafos CS-20; Vitamin E Acetate; Aloe Vera Leaf Juice; Diocide; or derivatives or combinations thereof.

In an embodiment, examples of suitable formulations include face cream formulations, comprising an emulsifier-free emulsion, wherein the emulsion is thickened by a star macromolecule disclosed herein, may include, but is not limited to, formulations comprising one or more of the following: Deionized Water; Disodium EDTA; 1,3 Butylene Glycol; Glycerin; Caffeine; Allantoin; Triethanolamine 99%; Myritol 318; Octyl Palmitate; Wickenol 171; Crodaphos CES; Cetyl Alcohol; Pationic SSL; Cetyl Palmitate; Vitamin E Acetate; BVOSC; Lexfeel 7; Lipo GMS 470; Vitamin A/D3 in Corn Oil; DC 1401; Actiphyte of Japanese Green Tea G; Actiphyte of Grape Seed G; DC Hydroglide; Diocide; or derivatives or combinations thereof.

Synthesis of the Rheology Modifier

Although any conventional method can be used for the synthesis of the multi-arm star macromolecules of the invention, free radical polymerization is the preferred and living/controlled radical polymerization (CRP) is the most preferred process.

CRP has emerged during the past decade as one of the most robust and powerful techniques for polymer synthesis, as it combines some of the desirable attributes of conventional free radical polymerization (e.g., the ability to polymerize a wide range of monomers, tolerance of various functionality in monomer and solvent, compatibility with simple industrially viable reaction conditions) with the advantages of living ionic polymerization techniques (e.g., preparation of low polydispersity index (PDI=$M_w/M_n$) polymer and chain-end functionalized homo- and block (co) polymers). The basic concept behind the various CRP procedures is the reversible activation of a dormant species to form the propagating radical. A dynamic and rapid equilibrium between the dormant and the active species minimizes the probability of bimolecular radical termination reactions and provides an equal opportunity for propagation to all polymer (or dormant) chains.

CRP procedures can be classified into three main groups based on the mechanism of reversible activation: (a) stable free radical polymerization (SFRP, Scheme 1a), (b) degenerative chain transfer polymerization (DT, Scheme 1b), and (c) atom transfer radical polymerization (ATRP, Scheme 1c).

Scheme 1. Three main groups of controlled radical polymerization based on the mechanism of reversible activation: (a) stable free radical polymerization (SFRP), (b) degenerative chain transfer polymerization (DT), and (c) atom transfer radical polymerzation (ATRP).

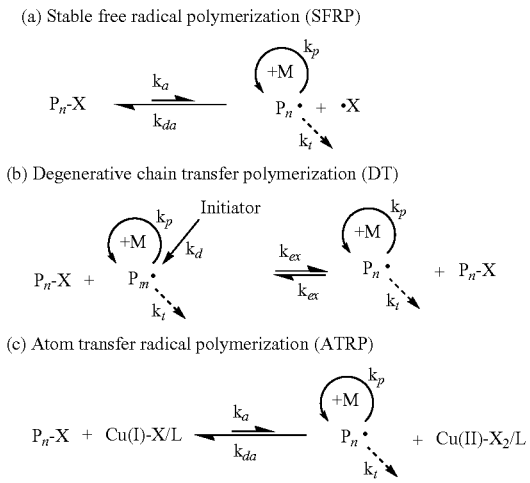

As shown in Scheme 1 various capping agents, X, are used for the different CRP procedures and they are summarized in Scheme 2. They include stable nitroxides (Scheme 2a), transition metal complexes (Scheme 2b), halides with transition metal catalysts (Scheme 2c), iodine with catalysts (Scheme 2d), sulfur compounds (Scheme 2e), iodine (Scheme 2f), and organometal compounds (Scheme 2g).

Scheme 2. Examples of capping agent X.

(a) Nitroxides (NMP)

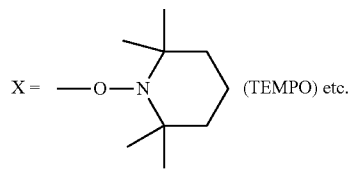

(b) Transition metal complexes

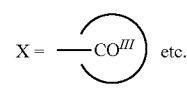 etc.

(c) Halides with transition metals (ATRP)

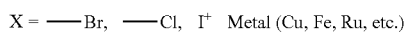

(d) Iodid with catalysts (RCTP)

(e) Dithioester, dithiocarbamate, and xanthate (RAFT)

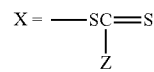

($Z$ = Ph, $CH_3$, $NEt_2$, OEt, etc.)

(f) Iodine (ITP)

(g) Tellurium, stibine, and bismuth compounds (TERP, SBRP, and BIRP)

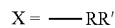

($R$ = Te, Sb, or Bi, $R'$ = $CH_3$, etc.)

Star polymers are nano-scale materials with a globular shape. As illustrated in FIG. 1, stars formed by the "arm first" procedure, discussed in detail below, can have a crosslinked core and can optionally possess multiple segmented arms of similar composition. Stars can be designed as homo-arm stars or mikto-arm stars. FIG. 1A represents a homo-arm star with block copolymer arms. Mikto-arm stars have arms with different composition or different molecular weight; FIGS. 1B and 1C. Both homo-arm stars and mikto-arm stars can optionally possess a high-density of peripheral functionality.

Synthesis of star polymers of the invention can be accomplished by "living" polymerization techniques via one of three strategies: 1) core-first" which is accomplished by growing arms from a multifunctional initiator; 2) "coupling-onto" involving attaching preformed arms onto a multifunctional core and the 3) arm-first" method which involves cross-linking preformed linear arm precursors using a divinyl compound While all above controlled polymerization procedures are suitable for preparation of an embodiment of the disclosed self assembling star macromolecules. Other embodiments are also exemplified, for example, the preparation of the self assembling multi-arm stars with narrow MWD, in contrast to prior art using ATRP. The reason for the use of the Controlled Radical Polymerization process (CRP) known as ATRP; disclosed in U.S. Pat. Nos. 5,763,546; 5,807,937; 5,789,487; 5,945,491; 6,111,022; 6,121,371; 6,124,411; 6,162,882: and U.S. patent application Ser. No. 09/034,187; Ser. No. 09/018,554; Ser. No. 09/359,359; Ser. No. 09/359, 591; Ser. No. 09/369,157; Ser. No. 09/126,768 and Ser. No.

09/534,827, and discussed in numerous publications listed elsewhere with Matyjaszewski as co-author, which are hereby incorporated into this application, is that convenient procedures were described for the preparation of polymers displaying control over the polymer molecular weight, molecular weight distribution, composition, architecture, functionality and the preparation of molecular composites and tethered polymeric structures comprising radically (co) polymerizable monomers, and the preparation of controllable macromolecular structures under mild reaction conditions.

An aspect of the present invention relates to the preparation and use of multi-arm star macromolecules by an "arm first" approach, discussed by Gao, H.; Matyjaszewski, K. *JACS*, 2007, 129, 11828. The paper and cited references therein are hereby incorporated by reference to describe the fundamentals of the synthetic procedure. The supplemental information available within the cited reference provides a procedure for calculation of the number of arms in the formed star macromolecule.

It is expected that biphasic systems such as a miniemulsion or an ab initio emulsion system would also be suitable for this procedure since miniemulsion systems have been shown to function as dispersed bulk reactors [Min, K.; Gao, H.; Matyjaszewski, K. *Journal of the American Chemical Society* 2005, 127, 3825-3830] with the added advantage of minimizing core-core coupling reactions based on compartmentalization considerations.

In one embodiment star macromolecules are prepared with composition and molecular weight of each segment predetermined to perform as rheology modifiers in aqueous based solutions. The first formed segmented linear (co) polymer chains are chain extended with a crosslinker forming a crosslinked core.

In another embodiment, a simple industrially scalable process for the preparation of star macromolecules is provided wherein the arms comprise segments selected to induce self assembly and wherein the self assemblable star macromolecules are suitable for use as rheology control agents in waterborne and solvent-borne coatings, adhesives, cosmetics and personal care compositions.

The invention is not limited to the specific compositions, components or process steps disclosed herein as such may vary.

It is also to be understood that the terminology used herein is only for the purpose of describing the particular embodiments and is not intended to be limiting.

The procedure for the preparation of star macromolecules may be exemplified by (co)polymerization of linear macromolecules, including macroinitiators (MI) and macromonomers (MMs), with a multi-vinyl cross-linker, a divinyl crosslinker is employed in the exemplary examples disclosed herein, to form a core of the star. The formation of the core of the star can also be formed through a copolymerization reaction wherein a monovinyl monomer is added to expand the free volume of the core to allow incorporation of additional arms into the congested core forming environment or to provide sufficient free volume within the core of the star to encapsulate functional small molecules. A molecule that functions as an initiator and a monomer, an inimer, can also be employed in the preparation of the core of the star macromolecule. When added to the reaction it functions to form a three arm branch in the core of the molecule and hence acts in a manner similar to the added monomer to increase the free volume within the star core.

The volume fraction of the core of the star can be controlled by appropriate selection of the crosslinker molecule or by conducting a copolymerization between the crosslinker and a vinyl monomer or an inimer. The composition of the core can be selected to provide an environment to encapsulate small molecules, such as fragrances, and control the rate of diffusion of the fragrance from the self assembled thickening agent after deposition on a part of the human body.

The core of the star polymers may contain additional functionality. This additional functionality can be of direct utility in certain applications or can be employed to tether or encapsulate further functional materials such as fragrances, stimuli responsive molecules or bio-responsive molecules to the core of the star by chemical or physical interactions.

The star macromolecules can be prepared in dilute solution when reaction conditions and crosslinker are chosen to avoid or reduce star-star coupling reactions.

The synthesis of multi-arm star polymers where the periphery of the star polymers contains additional functionality is possible. This functionality can be introduced by use of an initiator comprising the desired $\alpha$-functionality in the residue of the low molecular weight initiator remaining at the $\alpha$-chain end of each arm.

An embodiment of the present invention can be exemplified by the preparation of a multi-arm star macromolecule wherein the number of arms in the star macromolecule is between 5 and 500, preferentially between 10 and 250, with segments selected to induce self assembly when the star macromolecule is dispersed in a liquid wherein the self assemblable star macromolecules are suitable for use as thickening agents or rheology modifiers in cosmetic and personal care compositions at low concentrations of the solid in the thickened solution, preferably less than 5 wt %, and optimally less than 1 wt %. The dispersion medium can comprise aqueous based systems or oil based systems.

Figure 25:
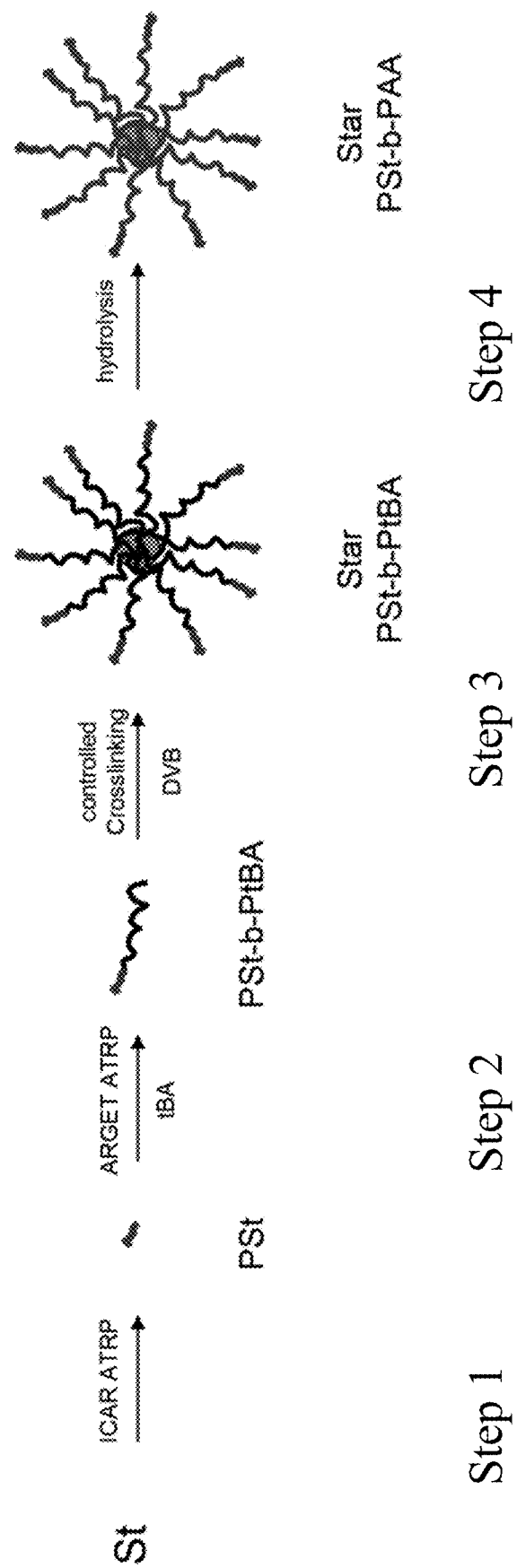
FIG. 25: depicts a multistep synthesis of PSt-b-PAA block copolymer stars.

The structure of an exemplary new thickening agent, or rheology modifier, of one embodiment, is a multiarm segmented star macromolecule wherein the core is prepared by controlled radical polymerization using an arm-first method. Scheme 3, as depicted in FIG. 25, provides a simple four step procedure that can be employed for preparation of an initial non-limiting exemplifying case the procedure is an atom transfer radical polymerization arm first macroinitiator method. In this approach the precursor of the arm(s) comprise a linear copolymer chain with a single terminal activatable group, as will be understood by one skilled in the art, having this disclosure as a guide, the activatable arm precursor will have a $\omega$-terminal functionality that under the conditions of the polymerization procedure can reversibly generate a radical. Scheme 3 illustrates the concept by sequential polymerization of styrene and tBA. These monomers are purely exemplary monomers and should not limit the applicability of the procedure in any manner since other monomers of similar phylicity can be employed. In Scheme 3 the polystyrene segment can be considered the outer shell of the star and the final poly(acrylic acid) segments the inner water soluble shell and the segment formed by chain extending the linear copolymer macroinitiators by reaction with the divinylbenzene crosslinker the core of the star.

Similar structures can also be prepared using the macromonomer method or a combination of the macromonomer and macroinitiator method in a controlled polymerization process, or even through free radical copolymerization conducted on macromonomers, as known to those skilled in the art. [Gao, H.; Matyjaszewski, K. *Chem.-Eur. J* 2009, 15, 6107-6111.]

Both the macromonomer and macroinitiator procedures allow incorporation of polymer segments prepared by procedures other than CRP [WO 98/01480] into the final star macromolecule. Polymer segments can comprise segments that are bio-degradable of are formed from monomers prepared from biological sources.

As noted above the first formed ATRP macroinitiator can be prepared by conducting a sequential ATRP (co)polymerization of hydrophobic and hydrophilic monomers or precursors thereof or can be prepared by other polymerization procedures that provide a functional terminal atom or group that can be converted into an ATRP initiator with a bifunctional molecule wherein one functionality comprises a transferable atom or group and the other functionality an atom or group that can react with the functionality first present on the (co)polymer prepared by a non-ATRP procedure. [WO 98/01480]

In aqueous solutions, the composition and molecular weight of the outer shell of hydrophobes, or agents that participate in molecular recognition, can be selected to induce self-assembly into aggregates and act as physical crosslinkers. Above a certain concentration, corresponding to the formation of a reversible three dimensional network, the solutions will behave as physical gels thereby modifying the rheology of the solution.

In one embodiment, the polymer compositions of the invention have significantly lower critical concentration for network (gel) formation compared to networks formed with block copolymers, graft and stars with a low specific number of attached arms due to:
  multi-arm structure (many transient junctions possible between hydrophobic parts of the stars)
  very high molecular weight of each star (5 thousand to 5 million or higher) allows high swelling ratio of the molecules in solution
  molecular organization on larger scales (>1 μm)

Whereas the examples above and below describe the preparation and use of block copolymers as arms with a well defined transition from one segment to the adjoining segment a segmented copolymer with a gradient in composition can also be utilized. The presence of a gradient can be created by addition of a second monomer prior to consumption of the first monomer and will affect the volume fraction of monomer units present in the transition from one domain to another. This would affect the shear responsiveness of the formed star macromolecule.

Star macromolecules with narrow polydispersity comprising arms with block copolymer segments can be formed with as few as 5 arms by selecting appropriate concentration of reagents, crosslinker and reaction temperature.

Star macromolecules can be prepared in a miniemulsion or reverse miniemulsion polymerization system. The first formed block copolymers are used as reactive surfactants for star synthesis by reaction with a selected crosslinker in miniemulsion.

EXAMPLES

| Abbreviation | Name | Form | Purity | Commercial Source |
|---|---|---|---|---|
| St | styrene | liquid | 99% | Sigma Aldrich |
| tBA | tertiary-butyl acrylate | liquid | 98% | Sigma Aldrich |
| AA | acrylic acid (formed by deprotection) | NA | NA | NA |
| HEA | hydroxyethyl acrylate | liquid | 96% | Sigma Aldrich |
| DEBMM | diethyl 2-bromo-2-methylmalonate | liquid | 98% | Sigma Aldrich |
| TPMA | tris(2-pyridylmethyl)amine | solid | 95% | ATRP Solutions |
| AIBN | 2,2'-Azobis(2-methylpropionitrile) | solid | 98% | Sigma Aldrich |
| $Sn(EH)_2$ | tin(II) 2-ethylhexanoate | liquid | 95% | Sigma Aldrich |
| DVB | divinylbenzene | liquid | 80% | Sigma Aldrich |
| TFA | trifluoroacetic acid | liquid | 99% | Sigma Aldrich |
| THF | tetrahydrofuran | liquid | 99.9% | Sigma Aldrich |
| NaOH | sodium hydroxide | solid | 98% | Sigma Aldrich |
| EBiB | Ethyl α-bromoisobutyrate | liquid | 98% | Sigma Aldrich |
|  | Methylene chloride | liquid | 99.6% | Sigma Aldrich |
|  | Acetonitrile | liquid | 99.8% | Sigma Aldrich |
| NaCl | Sodium chloride | solid | 99.7% | Fisher Chemical |
| DMAEMA | 2-(dimethylamino)ethyl methacrylate |  |  |  |
| PEGMA | (polyethylene glycol) methacrylate |  |  |  |
| NIPAM | N-isopropylacrylamide |  |  |  |

Synthesis, Purification and Properties of Star Thickening Agent

The initial examples of a star thickening agents with the structure shown below in FIG. 1 as structure A, are star macromolecules with PSt-b-PAA arms or PSt-b-P(HEA) arms.

Example 1: Preparation of a $(PSt-b-PAA)_X$ Star Macromolecule

The simple four step procedure was developed for the preparation of a poly(acrylic acid) based star macromolecule is described in Scheme 3. 1 kg of the star macromolecule with PSt-b-PtBA arms was prepared as follows.

STEP 1: Synthesis of a polystyrene macroinitiator using ICAR ATRP. The reaction conditions are St/DEBMM/ $CuBr_2$/TPMA/AIBN=50/1/0.002/0.003/0.05 in bulk at T=60° C., t=10.2 h. The reaction was run to ~30% conversion resulting in the molecular weight of the hydrophobic, polystyrene segment=1600 which is equivalent to an average degree of polymerization (DP) of 16.

Figure 2:
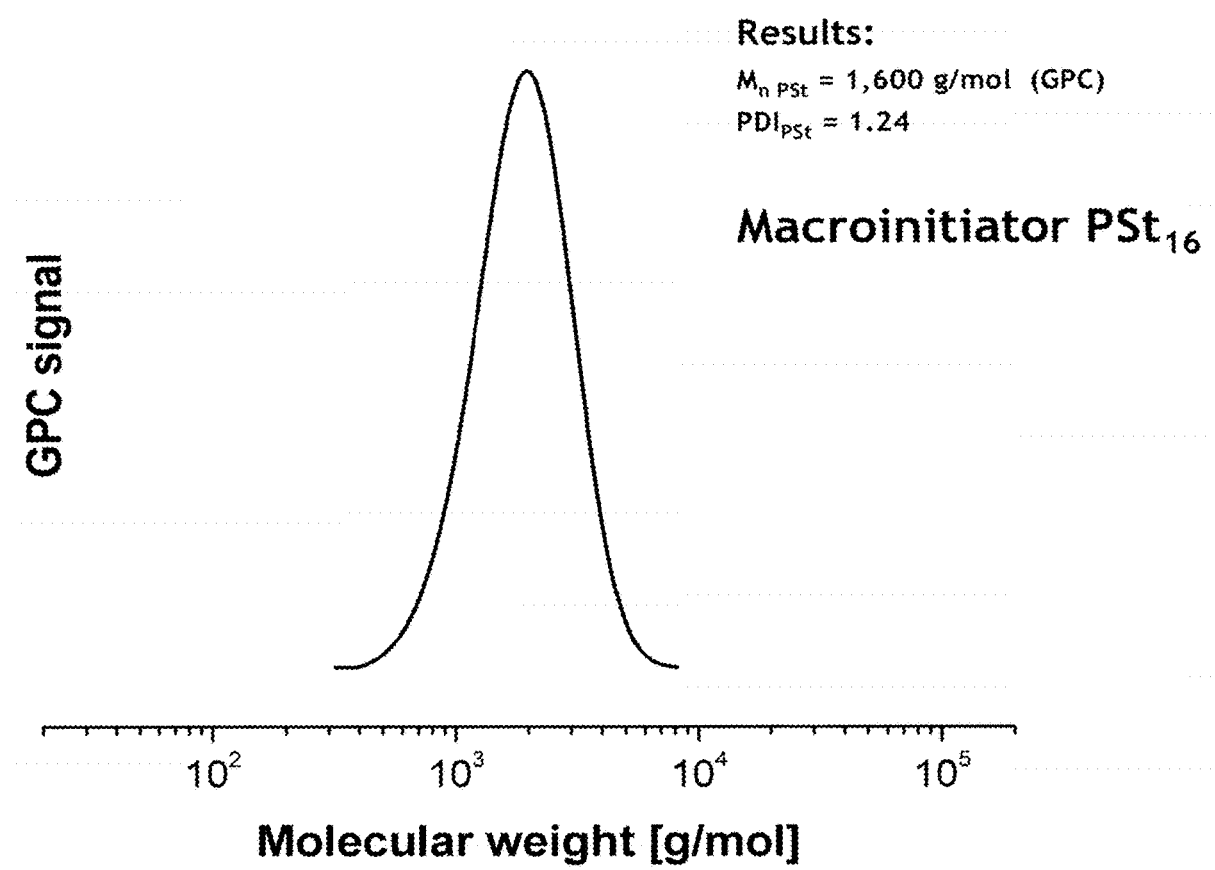
FIG. 2: GPC curve for the polystyrene macroinitiator formed in step 1 of the synthesis of an exemplary (PSt-b-PAA) star macromolecule.

The GPC trace obtained for the macroinitiator is shown in FIG. 2.

Figure 3:
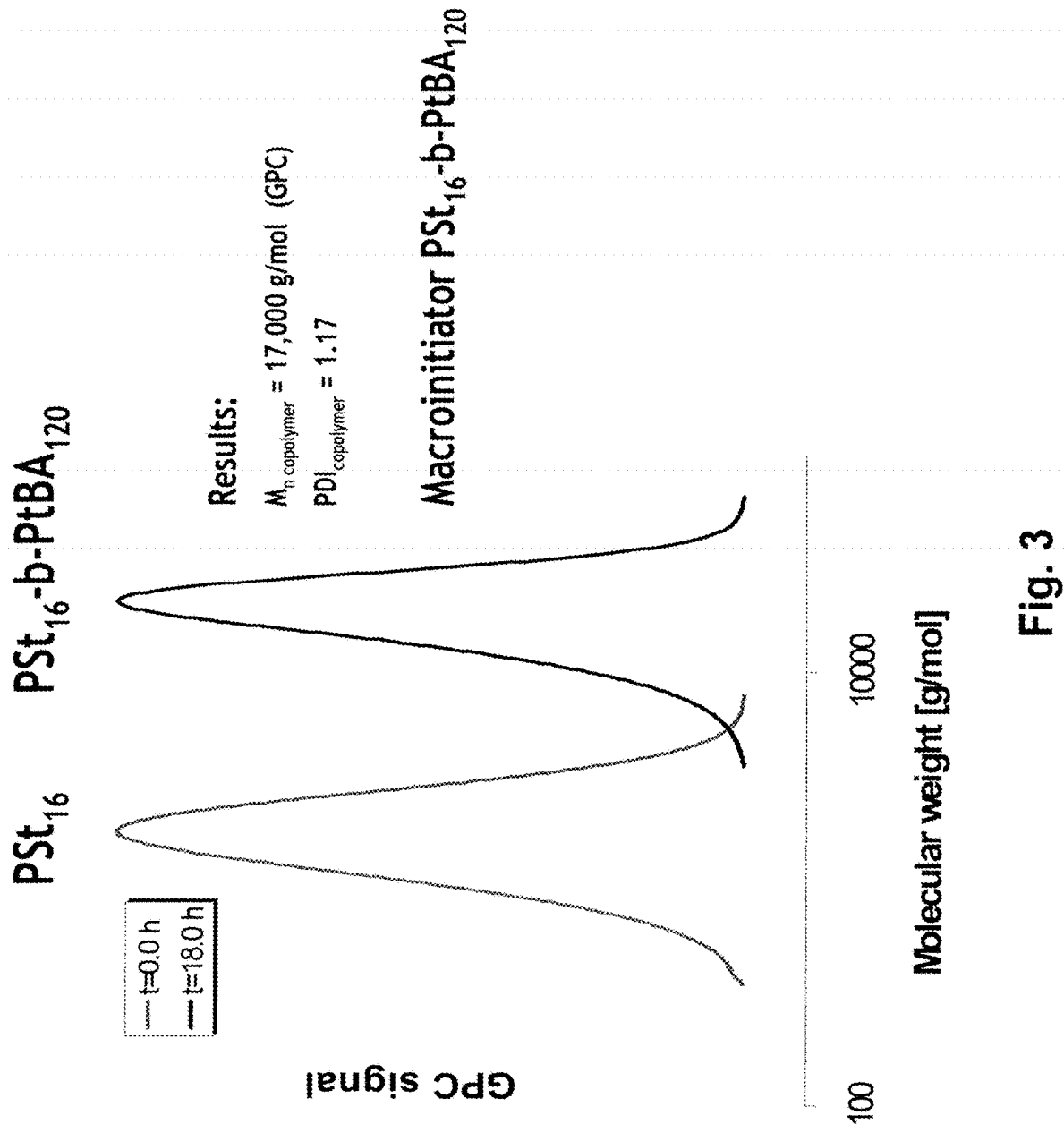
FIG. 3: GPC curves for the polystyrene macroinitiator formed in step 1 of the synthesis of an exemplary (PSt-b-PAA) star macromolecule and GPC curve for block copolymer formed after chain extension with tBA in step 2 of the synthesis.

STEP 2: Synthesis of polystyrene-b-poly(t-butyl acrylate) segmented block copolymer macroinitiator. The reaction conditions for the synthesis of PSt-b-PtBA macroinitiator arm are: tBA/PSt/$CuBr_2$/TPMA/$Sn(EH)_2$=200/1/0.01/0.06/0.008 in anisole (0.5 volume eq. vs. tBA), T=55° C., t=18.0 h. A higher molecular weight precursor of the water soluble segment was targeted to allow significant degree of swelling of the inner shell of the final functional star macromolecule. The final molecular weight of the poly(t-butyl acrylate) segment in the block copolymer was 15,400 which is equivalent to a DP=120. The GPC curves of the polystyrene macroinitiator and the formed block copolymer macroinitiator is shown in FIG. 3 and clearly indicates that a clean chain extension had occurred.

STEP 3: Synthesis of the (PSt-b-PtBA)x Star Macromolecule

Figure 4:
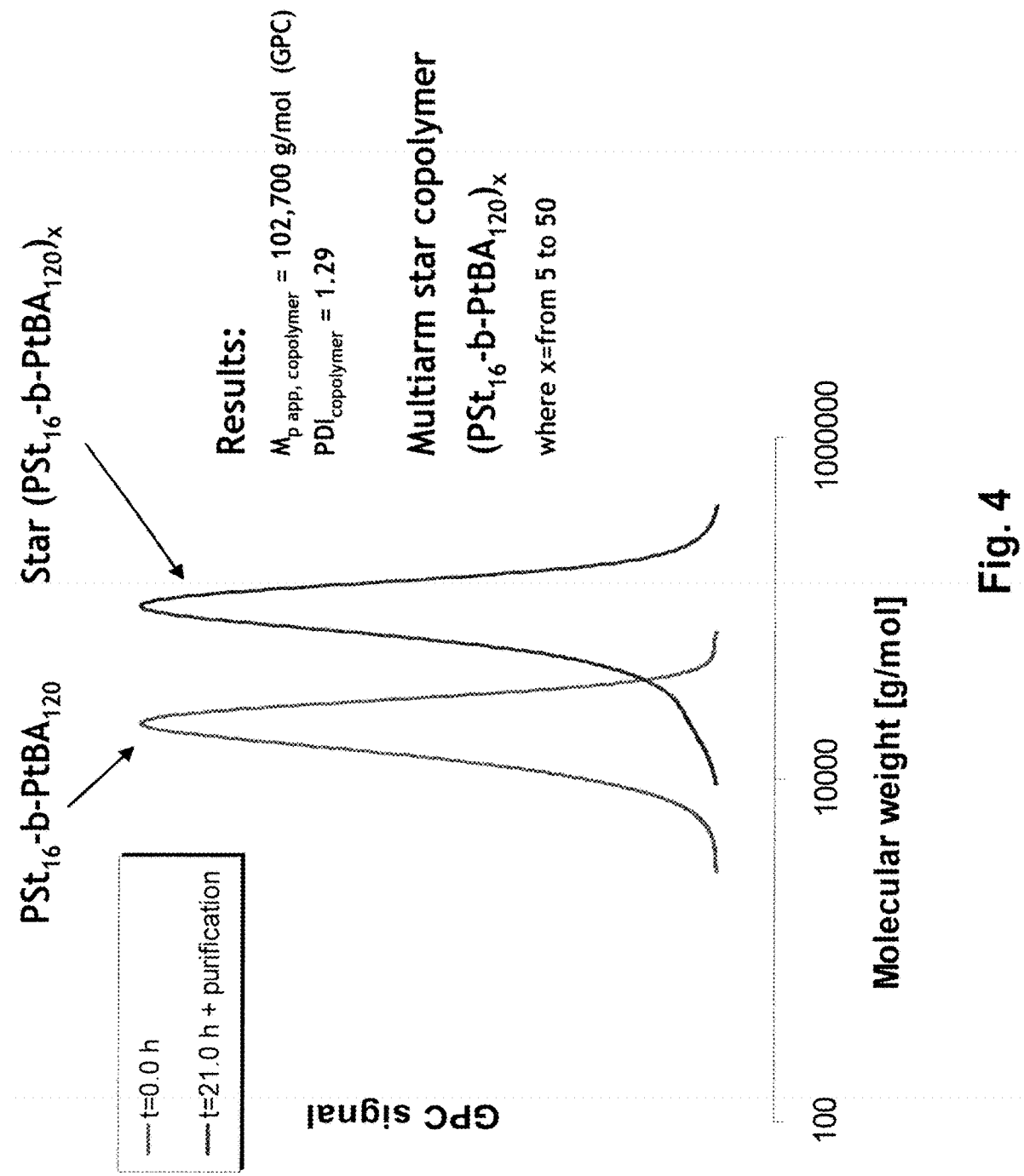
FIG. 4: GPC curves of the PSt-b-tBA block copolymer and the star macromolecule formed after core formation reaction is step 3 of the formation of an exemplary (PSt-b-PAA) star macromolecule.

A multi-arm star macromolecule was prepared by conducting a further chain extension reaction with the block copolymer macroinitiator formed in step 2. The reaction was conducted with a mole ratio of block copolymer to divinylbenzene of 1:12 in anisole. The reaction conditions are: $DVB/PSt-b-PtBA/CuBr_2/TPMA/Sn(EH)_2=12/1/0.02/0.06/0.1$ in anisole (38 volume eq. vs. DVB), T=80° C., t=21.0 h). The GPC curves and results of the star forming reaction are provided in FIG. 4. It can be seen that a multi-arm star macromolecule with a crosslinked core was formed. The GPC molecular weight of the star was 102,700 with a PDI 1.29, which would indicate an average of six arms but this is an underestimate of the actual number of arms since the star molecule is a compact molecule. Indeed in this situation the number of arms in the star molecule is close to 30.

The number of arms can be modified by conducting the core forming reaction with a different ratio of crosslinking agent to arm precursor or by running the reaction with a different concentration of reagents.

STEP 4: Deprotection of the (PSt-b-PtBA)x star macromolecule to (PSt-b-PAA)x star block copolymer to provide water soluble poly(acrylic acid) segments in the multi-arm star macromolecule. The PSt-b-PtBA arms of the star macromolecule were transformed to PSt-b-PAA arms using a new procedure. Polymer was dissolved in methylene chloride and trifluoroacetic acid to deprotect tBu groups, the reaction was performed at room temperature for 60.0 h. Then polymer was decanted and washed 3 times with acetonitrile. Polymer was then solubilized in THF and precipitated into acetonitrile. The star macromolecule was dried in vacuum oven for 3 days at 50° C. The amount of polymer obtained after purification was 550 g, which would correspond to full conversion of PtBA to PAA.

Example 2: Properties of (PSt-b-PAA) Star Macromolecule as a Thickening Agent

Figure 5:
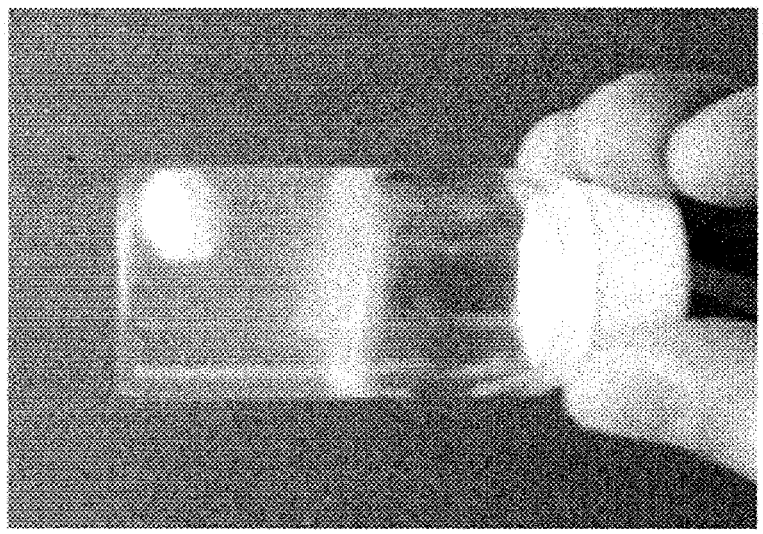
FIG. 5: Image showing the thickening properties of (PSt-b-PAA) star macromolecule.

The thickening properties of the final star macromolecule were investigated in aqueous solution. 100 mg of (PSt-b-PAA) star macromolecule was dissolved in 0.5 ml of THF and transferred to 10 ml of water. Solution was then neutralized with 2 ml of basic water (with NaOH). After few minutes of stirring gel was formed, see image in FIG. 5.

Figure 6:
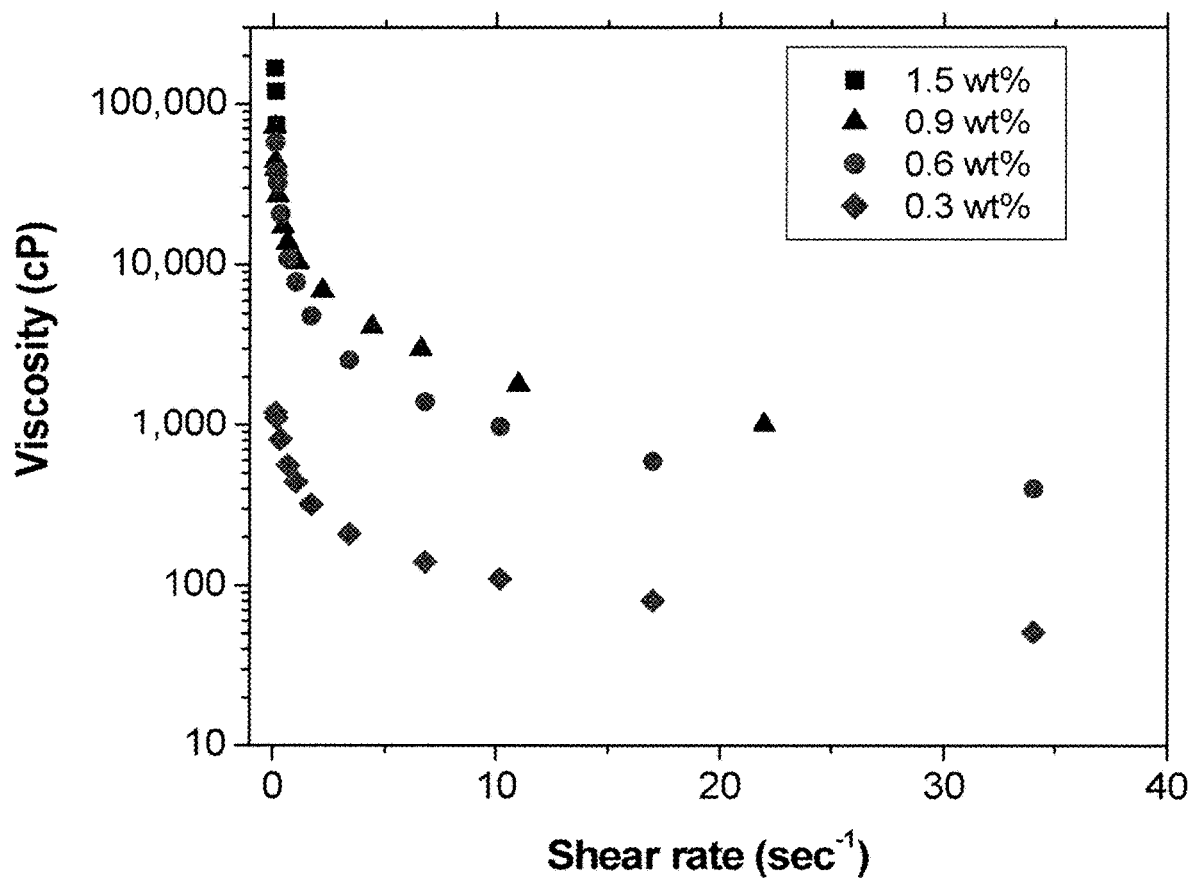
FIG. 6: Viscosity of aqueous solution of (PSt-b-PAA) star macromolecule vs. shear rate.

The rheological properties of the multi-arm star built with a longer poly(acrylic acid (PAA) hydrophilic internal core segment and a short hydrophobic polystyrene (PSt) peripheral segment were then investigated. The viscosity of aqueous solutions containing different concentrations of the star macromolecule vs. shear rate were measured; using a Brookfield LVDV-E, Spindle #31(or #34, #25) at a T=25° C., and the results are presented in FIG. 6. It is clear that even very low concentrations of the star macromolecule in water (<0.6 weight %) the apparent viscosity of the sample is very high (in the range of 50,000 to 100,000 centipoise (cP)).

In comparison, leading thickening agents on the market for personal care products (e.g. natural nonionic vegetable derived liquid thickener Crothix Liquid by CRODA or synthetic acrylate based copolymer DOW CORNING RM 2051) are used at the level of 2-5 weight % and only increase the viscosity of a water based solution up to 5,000-20,000 cP.

Figure 7:
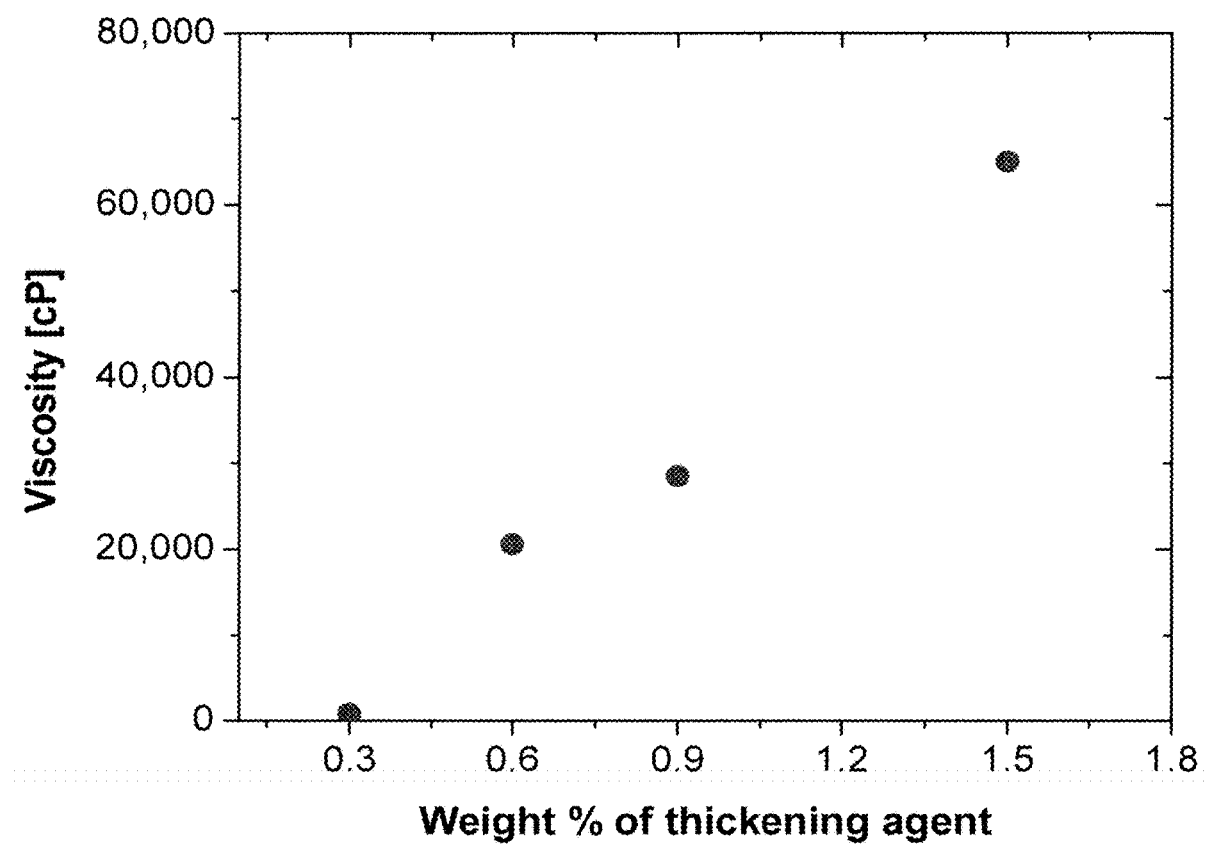
FIG. 7: Viscosity of aqueous solution of (PSt-b-PAA) star macromolecule vs. concentration.

FIG. 7 presences the viscosity of aqueous solution of a (PSt-b-PAA) star macromolecule vs. concentration. The measurement was conducted on a Brookfield LVDV-E with spindle #31(or #34, #25) at a temperature=25° C. and rate=1 RPM. It can be seen that for this particular star macromolecule 0.3 weight % concentration of star macromolecule in water is a minimum amount for gel formation and that higher concentrations significantly increase the viscosity of the resulting solution.

Tests indicated that the thickening agent provided formulations that exhibited a lack of tackiness, a very pleasant feel on the skin.

Figure 8:
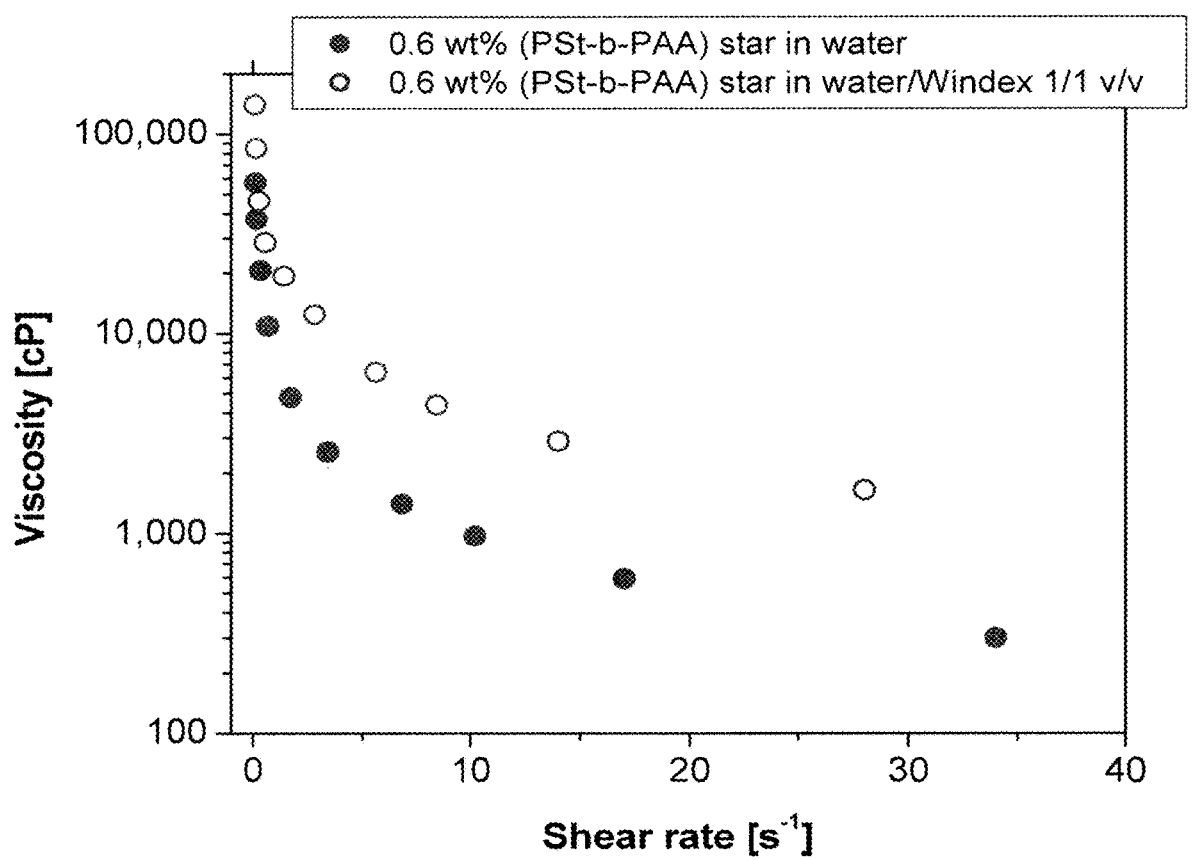
FIG. 8: Viscosity of an aqueous solution and a water/windex (1/1 v/v) solution of (PSt-b-PAA) star macromolecule vs. shear rate.
Figure 9:
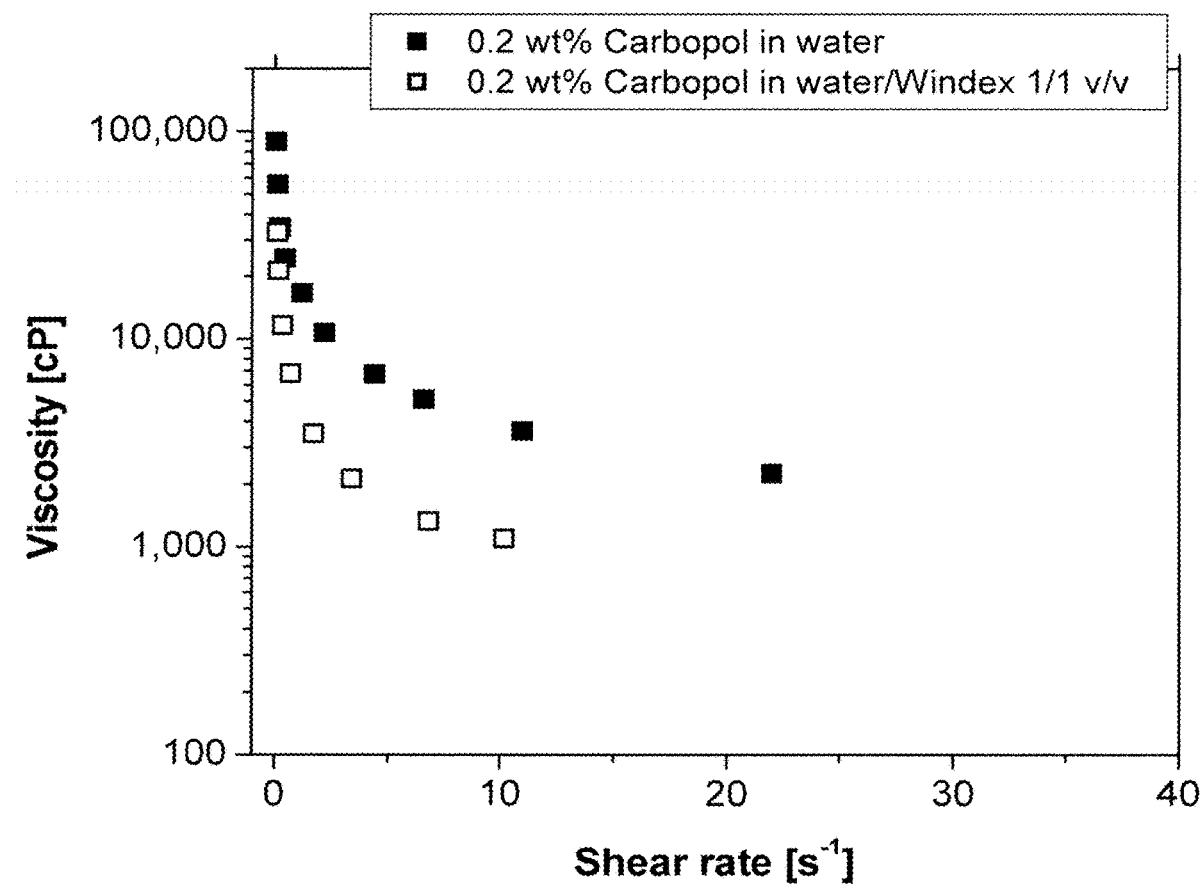
FIG. 9: Viscosity of an aqueous solution and a water/windex (1/1 v/v) solution of Carbopol EDT 2020 vs. shear rate.

Example 3: Properties of (PSt-b-PAA) Star Macromolecule as Thickening Agents in Harsh Environments The thickening properties of the final star macromolecule were investigated in aqueous solution in the presence of an oxidizing agent and at high pH. FIG. 8 presents the viscosity of an aqueous solution of (PSt-b-PAA) star macromolecule and the viscosity of water/windex (1/1 v/v) solution of (PSt-b-PAA) star macromolecule and FIG. 9 presents the results obtained with Carbopol EDT 2020 in the same media. The pH of the aqueous solution was 6-7 while for the water/Windex solution pH=9-10. (Measurement of viscosity was conducted using a Brookfield LVDV-E, Spindle #31 (or #34, #25), T=25° C.) It can be seen that viscosity of water/windex solution is higher than that of water solution. The performance of (PSt-b-PAA) star macromolecule as thickening agent is not diminished in this harsh environment presented by the windex/water solution with a pH=9-10 resulting from the presence of high amount of ammonia-D. In comparison, the thickening properties of the leading thickener on the market, Carbopol EDT 2020, were decreased in similar conditions and FIG. 9 shows that the viscosity of water/windex solution is lower than that of pure aqueous solution.

It is envisioned that the poor performance of Carbopol vs. (PSt-b-PAA) star macromolecule as thickening agent in water/Windex solution is a consequence of the high amount of ester bonds in its structure which can interact with the ionic species present in such harsh environment or can be even degraded. On the other side (PSt-b-PAA) star macromolecule has only C-C bonds, which make this thickening agent stable in water/Windex solution and overall thickening performance is not decreased.

Example 4: Properties of (PSt-b-PAA) Star Macromolecule vs. (PAA) Star Macromolecule as Thickening Agents A (PAA) star macromolecule was synthesized in order to compare its properties to those determined for the (PSt-b-PAA) star macromolecule. Synthesis of (PAA) star was performed in similar way as for synthesis of (PSt-b-PAA) star macromolecule but starting with pure PtBA arms.

Figure 10:
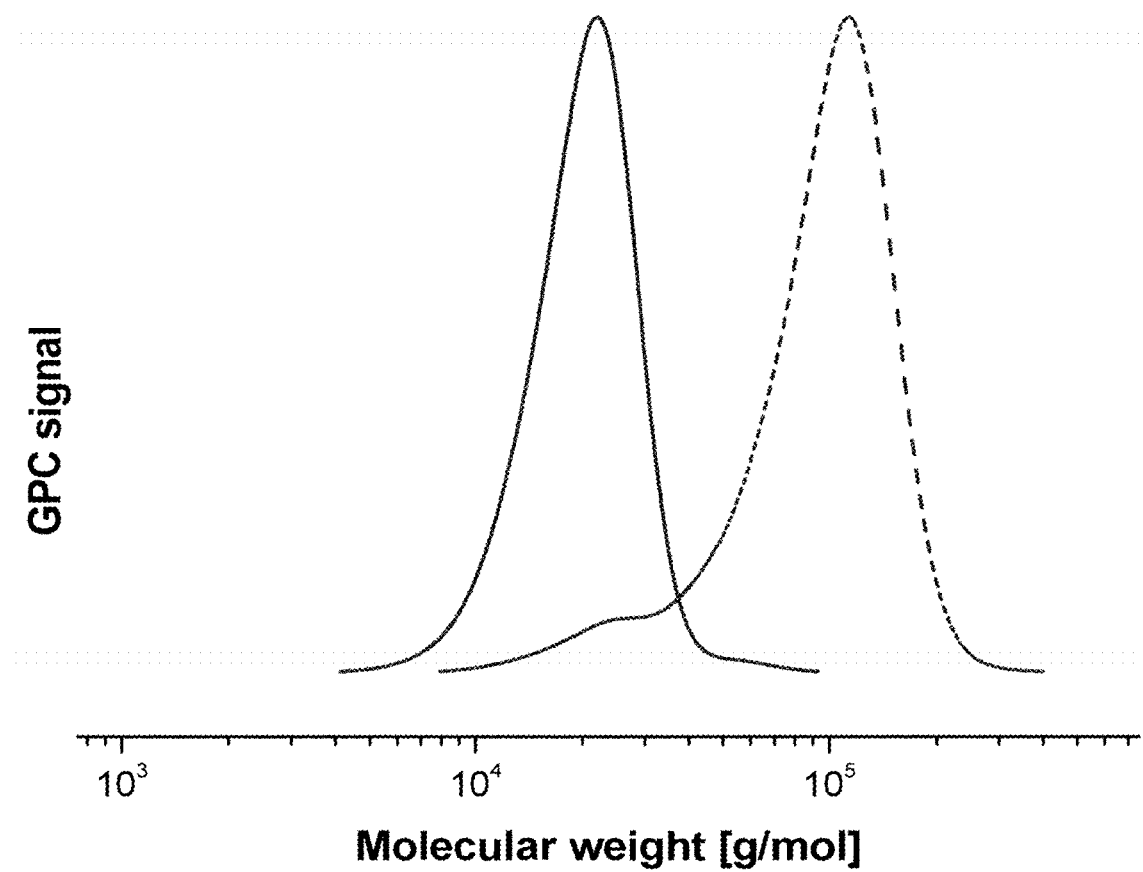
FIG. 10: GPC Curves for preparation of the precursor to a PAA star. Solid line PtBA $M_n$=18,900 PDI=1.14; Dashed line (PtBA)$_X$ star with $M_{n,app}$ 112,600 PDI=1.36
Figure 11:
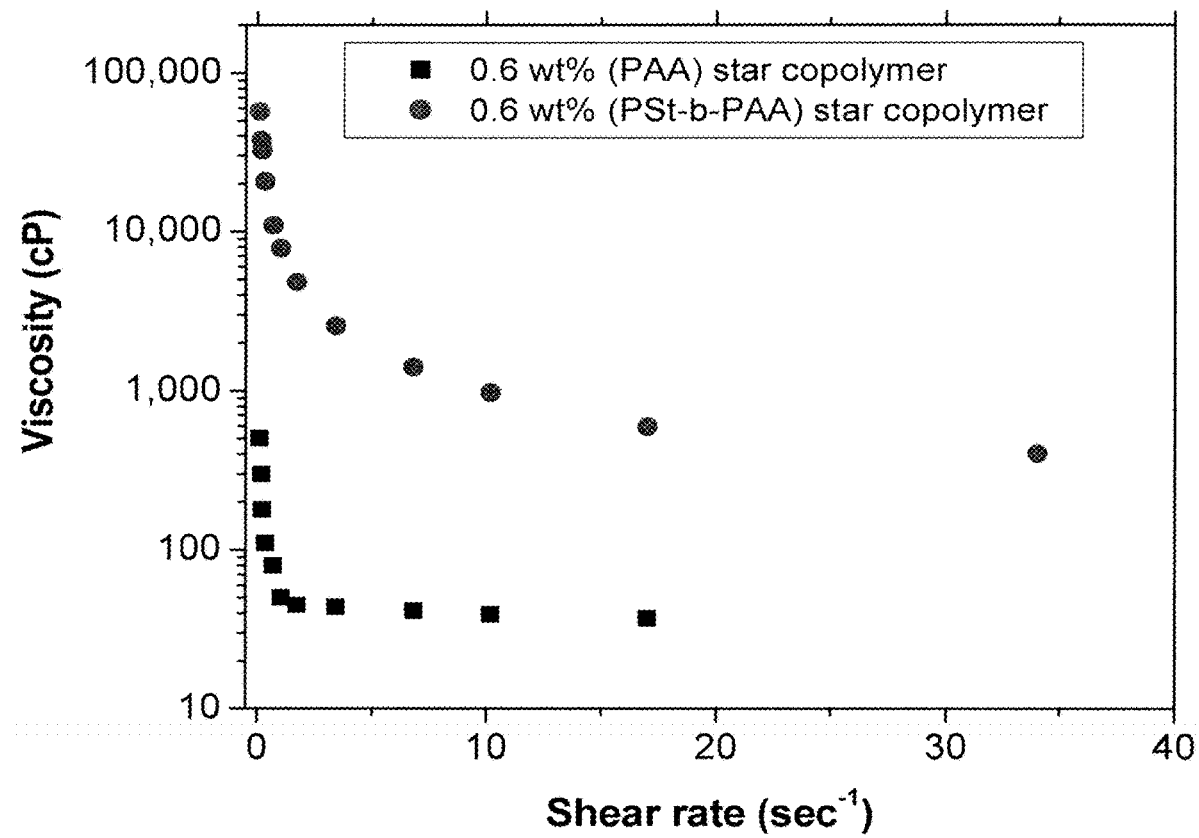
FIG. 11: Viscosity of aqueous solution of (PSt-b-PAA) star macromolecule and (PAA) star macromolecule vs. shear rate.

The final (PAA) star had similar molecular weight, number of arms and molecular weight distribution to the (PSt-b-PAA) star macromolecule, FIG. 10. The only one difference between two star macromolecules is the outer shell which comprises of PSt with degree of polymerization 16 in (PSt-b-PAA) star macromolecule whereas this star macromolecule possess pure PAA homo-polymeric arms. FIG. 11 presents the viscosity of aqueous solutions of (PSt-b-PAA) star and (PAA) star macromolecules. The measurement was conducted using a Brookfield LVDV-E fitted with a #31 spindle at a temperature=25° C. and pH=7. It can be seen that viscosity of star macromolecule with a hydrophobic outer shell has very strong thickening properties, where the pure (PAA) star has low thickening effect on water.

Therefore one can conclude that in order to thicken aqueous based media the proposed multi-arm star macromolecules have to have a blocky structure, with a hydrophilic inner shell and a hydrophobic outer shell. Without wishing to be limited by a proposed mechanism we believe these results in aqueous media can be explained by the induced self-assembly of the hydrophobic segments into aggregates, the hydrophobes act as "junctions" between aggregates, and above a certain concentration, a three-dimensional reversible physical network is formed with a behavior similar to conventional gels.

Example 5: (PSt-b-PAA) Star Macromolecule as Thickening and Emulsifying Agent

Figure 12:
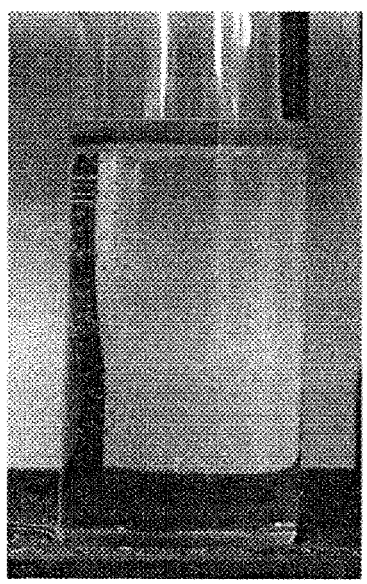
FIG. 12: Images demonstrating the emulsifying properties of (PSt-b-PAA) star macromolecule.
Figure 12:

Due to its very well-defined structure, (PSt-b-PAA) multi-arm star macromolecule may act not only as a thickening agent but also as efficient emulsifying agent. FIG. 12 presents images demonstrating the emulsifying properties of (PSt-b-PAA) star macromolecule. First photograph shows mixture of water with 2 volume % of pure lemon oil. After vigorous mixing, water and oil quickly separated into two phases. The second photograph presents water with 2 volume % of lemon oil and 0.6 weight % of thickening agent. After vigorous mixing, the phase separation did not occur and thicken properties did not decrease. Solutions were shaken for 1 min and photographs were taken 2 h after mixing.

Its hydrophobic core (as well as hydrophobic outer shell) may act as a storage place for small organic molecules (e.g. vitamins, fragrances, sunblock agents, etc.). This provides for the possibility for delivery of functional organic molecules, e.g. fragrance for slow release or UV absorbing molecules in sunscreens to any part of the body in a pleasant feeling emulsion.

In order to provide an equivalent response for non-polar media the phylicity of the inner and outer shells would have to be reversed.

Example 6: Mikto-Arm Star Macromolecules

A multi-arm star macromolecule was synthesized. The procedures for forming the arms PSt-b-PtBA and PtBA were similar to that described in Example 1. Next, two different arms were crosslinked together to form a star macromolecule. Reaction conditions for core forming crosslinking reaction: DVB/[PSt-b-PtBA/PtBA]/CuBr2/TPMA/Sn(EH)2=17/1/0.02/0.06/0.2 in anisole (38 volume eq. vs. DVB), (1667 ppm of Cu) T=95° C., t=53.0 h, PSt-b-PtBA/PtBA=1/4. Next, PtBA was transformed to PAA by deprotection with acid as described in Step 4 in Example 1.

Figure 13:
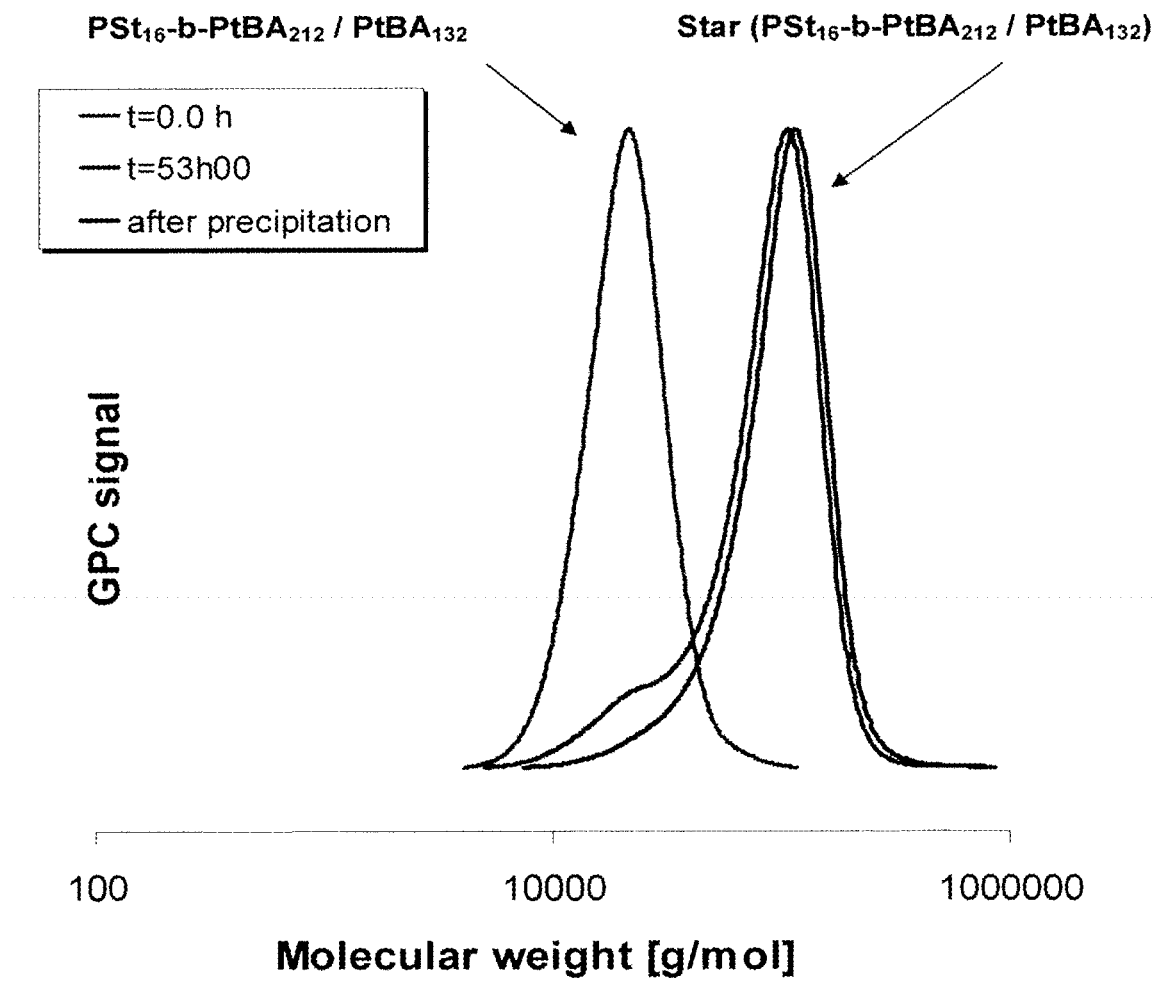
FIG. 13: Synthesis of [(PSt-b-PtBA)/(PtBA)] star macromolecule using arm-first method.
Figure 13:
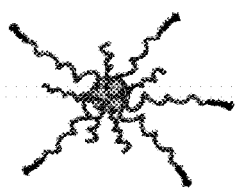
Figure 14:
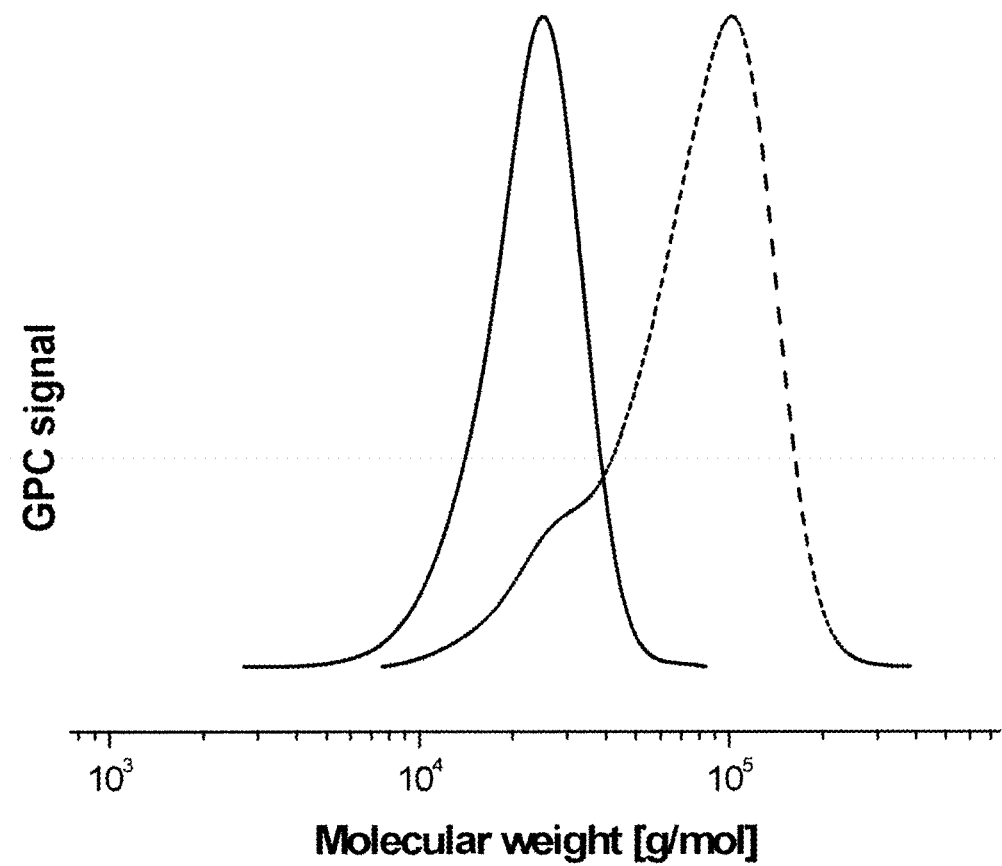
FIG. 14: GPC curves for $C_{18}$-PtBA arm star macromolecule, Solid line $C_{18}$-PtBA arm with $M_n$=19,200 PDI=1.16; dashed line ($C_{18}$-PtBA)$_X$ star macromolecule $M_{n,app}$=95,600 PDI=1.48.
Figure 15:
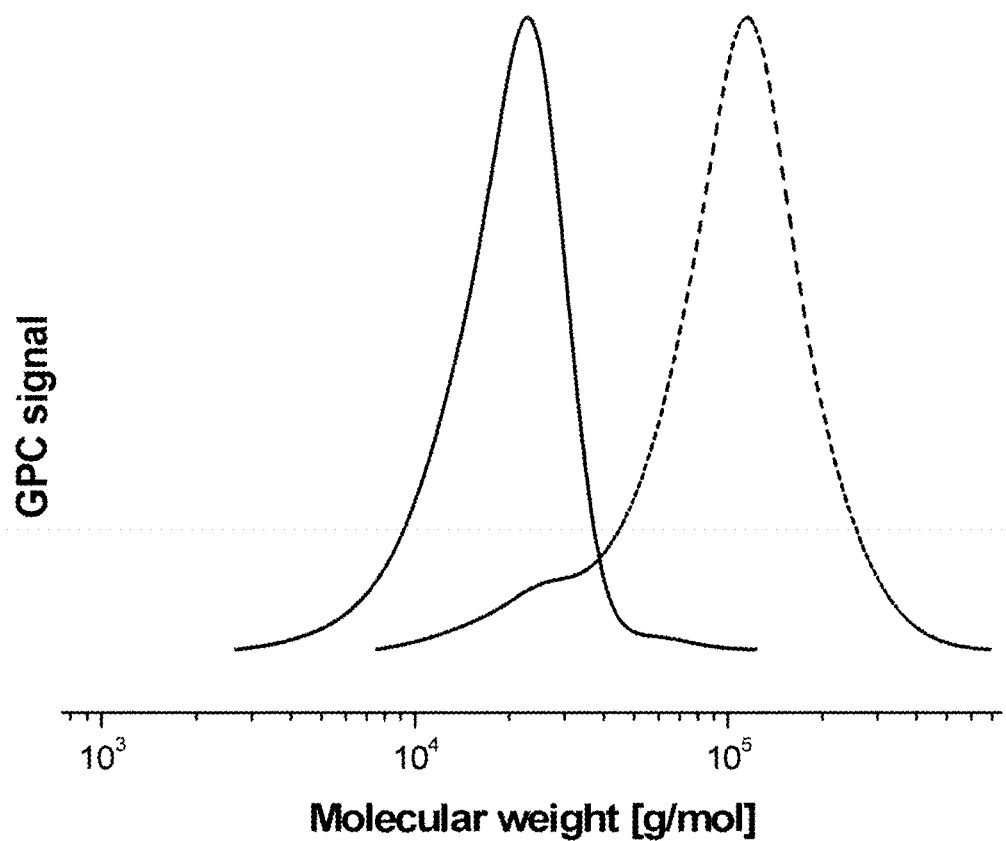
FIG. 15. GPC curves for $C_{12}$-PtBA arm star macromolecule, Solid Line $C_{12}$-PtBA $M_n$=17,500 PDI=1.22; Dashed line ($C_{12}$-PtBA)$_X$$M_{n,app}$ 113,900 PDI=1.53.
Figure 16:
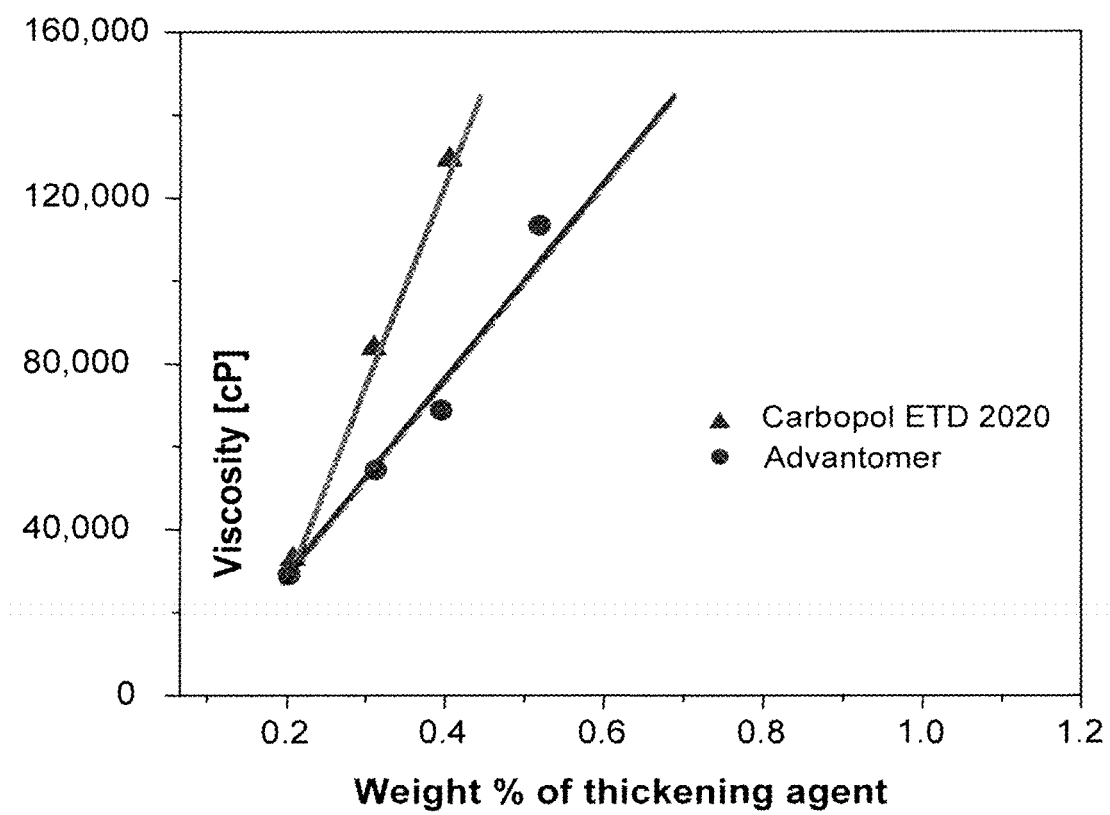
FIG. 16: is a graph comparing viscosity of Advantomer and Carbopol ETD 2020 at varying thickening agent weight %.
Figure 17:
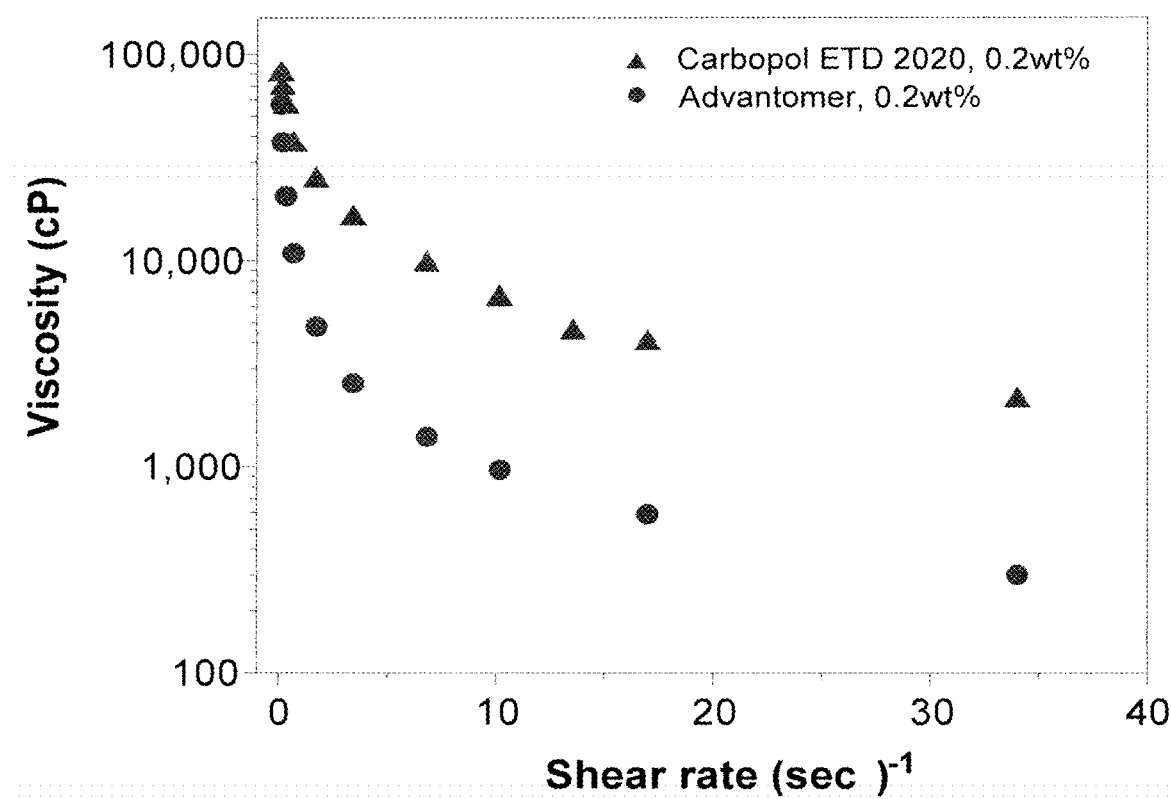
FIG. 17: is a graph comparing viscosity of Advantomer and Carbopol ETD 2020 at varying shear rates.

FIG. 13 shows the GPC curves of the arms and the formed mikto-arm star macromolecule before and after purification by precipitation. Schematic 13B shows a representation of such a mikto-arm star macromolecule.

Synthesis of stars with lower amounts of the outer PSt block was successfully performed. Two stars were synthesized, one with 50% and one with 20% of PSt-b-PAA arms and 50% and 80% pure PAA arms (WJ-08-006-234 and WJ-06-235) by the procedures detailed above. Studies show that these star macromolecules can be dispersed directly in warm water. Thickening properties of these two new stars were as good as first exemplary star with 100% of PSt-b-PAA arms.

Stars with different outer hydrophobic shells can be prepared. One example that provides an outer shell which exhibits a Tg below use temperature is a star prepared with a PnBA outer shell.

Another approach which can reduce the cost of the preparing an outer hydrophobic shell is conversion of commercially available α-olefins to an ATRP initiator by reaction with a halo-alky(meth)acrylylhalide.

Example 7: Stars With Different Hydrophobic Segments

One parameter which may significantly change viscosity of thickening agent as well as its interaction with surfactant in shampoo formulations is the type of hydrophobic unit capped at the peripheral end of a fraction of the arms of the star macromolecule. Two additional stars were synthesized in order to compare to $(PSt_{16}\text{-}PAA_{120})_X$ (before deprotection: $M_{n,app}$=102,700 g/mol, PDI=1.29) star macromolecule.

These stars include:
A) $C_{18}\text{-}PAA_{146})_X$: $M_{n,app}$=95,600 g/mol, PDI=1.48,
B) $C_{12}\text{-}PAA_{134})_X$: $M_{n,app}$=113,900 g/mol, PDI=1.53,
Each star was prepared in three steps:
i) preparation of PtBA arm,
ii) crosslinking arms into star macromolecule,
iii) deprotection of tBu groups. All of the stars had relatively low PDI with low amount of unreacted arms (<15 wt %).

A new PtBA macroinitiator was prepared from an initiator containing a linear $C_{18}$ alkyl chain for preparation of the $(C_{18}\text{-}PAA_{146})_X$ star. The synthesis of this arm precursor $C_{18}\text{-}PtBA\text{-}Br$ was accomplished using ARGET ATRP of tBA using $C_{18}$ alkyl chain functionalized EBiB. The conditions and properties of synthesized polymer are shown in Table 1.

TABLE 1

Experimental conditions and properties of PtBA prepared by ARGET ATRP.[a]

| Entry | Molar ratios | | | | | Cu [ppm] | Time (min) | Conv. (%) | $M_{n, theo}$[b] | $M_{n, GPC}$ | $M_w/M_n$ |
| --- | --- | --- | --- | --- | --- | --- | --- | --- | --- | --- | --- |
| | tBA | I | CuBr$_2$ | L | RA | | | | | | |
| 08-006-160 | 300 | 1 | 0.015 | 0.06 TPMA | 0.1 | 50 | 1380 | 47 | 18200 | 19700 | 1.19 |

[a] I = $C_{18}$-EBiB, L = Ligand, RA = reducing agent = Sn(EH)$_2$; [tBA]$_0$ = 4.67M; T = 60° C., in anisole (0.5 volume equivalent vs. monomer);
[b] $M_{n, theo}$ = ([M]$_0$/[C$_{18}$-EBiB]$_0$) × conversion This macroinitiator was than crosslinked using DVB into a star macromolecule. After deprotection of tBu groups by stirring the reaction for 3 days in the presence of TFA resulting in transformation to PAA units star was precipitated from $CH_2Cl_2$. The viscosity of resulting $(C_{18}\text{-PAA})x$ star and the $(C_{12}\text{-PAA})x$ star can be compared to (PSt-b-PAA)x in water and shampoo formulations.

Example 8: Stars With an Inner P(HEA) Shell

P(HEA) star macromolecules that comprise water soluble non-ionizable hydrophilic segments selected to make the star macromolecules compatible with solutions further comprising dissolved/dispersed salts that are additionally stable over a broad range of pH.

The PSt-b-PHEA arm precursor was prepared using ICAR ATRP. Conditions for the polymerizations and characterization of the resulting polymer are shown in Table 2. Polymerization was well controlled and well-defined block copolymer was prepared with relatively low (PDI=1.26 and 1.20). This is the first example of successful ICAR ATRP for acrylate type monomer. PSt-b-PHEA arm precursor was purified by precipitation into ethyl ether and dried under vacuum over two days at 50° C.

T=60° C., t=10.2 h. The reaction was run to ~30% conversion. The resulting reaction product was purified to obtain the PSt in powder form. A portion of the PSt powder was dissolved in THF and passed through the GPC column. The GPC trace obtained for the macroinitiator is shown in FIG. 2. The measured molecular weight of the hydrophobic, polystyrene segment=1600 which is equivalent to an average degree of polymerization (DP) of about 15-16 and the PDI was measured to be 1.24.

STEP 2: One-Pot Synthesis of Polystyrene-b-Poly(t-Butyl Acrylate) and Poly(t-Butyl Acrylate) Macroinitiator The following components were introduced into the reaction vessel in the following molar ratio: tBA/PSt (from step1)/$CuBr_2$/TPMA/Sn(EH)$_2$=200/0.2/0.01/0.06/0.1, in anisole (0.5 volume eq. vs. tBA), T=55° C. About 2.0 hours after the reaction was initiated, the conversion of the tBA reached about 6% and a portion of the PSt-b-PtBA was recovered and measured by GPC with the following results $M_n$=19,800 g/mol; PDI=1.16. It was determined that the following $PSt_{15}$-b-$PtBA_{140}$ copolymeric block was obtained. Then, 0.8 molar ratio amount, relative to the

TABLE 2

Experimental conditions and properties of PSt-b-PHEA prepared by ICAR ATRP.[a]

| Entry | Molar ratios | | | | | Cu [ppm] | Time (min) | Conv. (%) | $M_{n,\ theo}$[b] | $M_{n,\ GPC}$ | $M_w/M_n$ |
|---|---|---|---|---|---|---|---|---|---|---|---|
| | HEA | I | $CuBr_2$ | L | RA | | | | | | |
| 08-006-155 | 200 | 1 | 0.04 | 0.04 TPMA | 0.1 | 200 | 1200 | 63 | 16100 | 30400 | 1.26 |
| 08-006-158 | 300 | 1 | 0.05 | 0.05 TPMA | 0.05 | 167 | 1230 | 54 | 20300 | 42300 | 1.20 |

[a] I = PSt (08-006-29, $M_n$ = 1600 g/mol, PDI = 1.20), L = Ligand, RA = reducing agent = AIBN; $[HEA]_0$ = 5.44M; T = 65° C., in DMF (0.7 volume equivalent vs. monomer);
[b] $M_{n,\ theo}$ = $([M]_0/[PSt]_0)$ × conversion.

Different crosslinking agents were investigated, including DVB and in run 08-006-159 di(ethylene glycol) diacrylate (DEGlyDA) and in run 08-006-161 DEGlyDA with small amount of HEA monomer. The reaction was not fully controlled when conversion of the added divinyl crosslinker was driven to high conversion as a consequence of star-star core coupling reactions resulted in gel formation. However at lower conversion of the crosslinker and under more dilute conditions star macromolecules were formed.

Example 9: Preparation of a $(PSt_{15}$-b-$PAA_{290}/PAA_{150})_{\sim30}$ Miktoarm Star Macromolecule (Referenced Herein as Advantomer)

Figure 26:
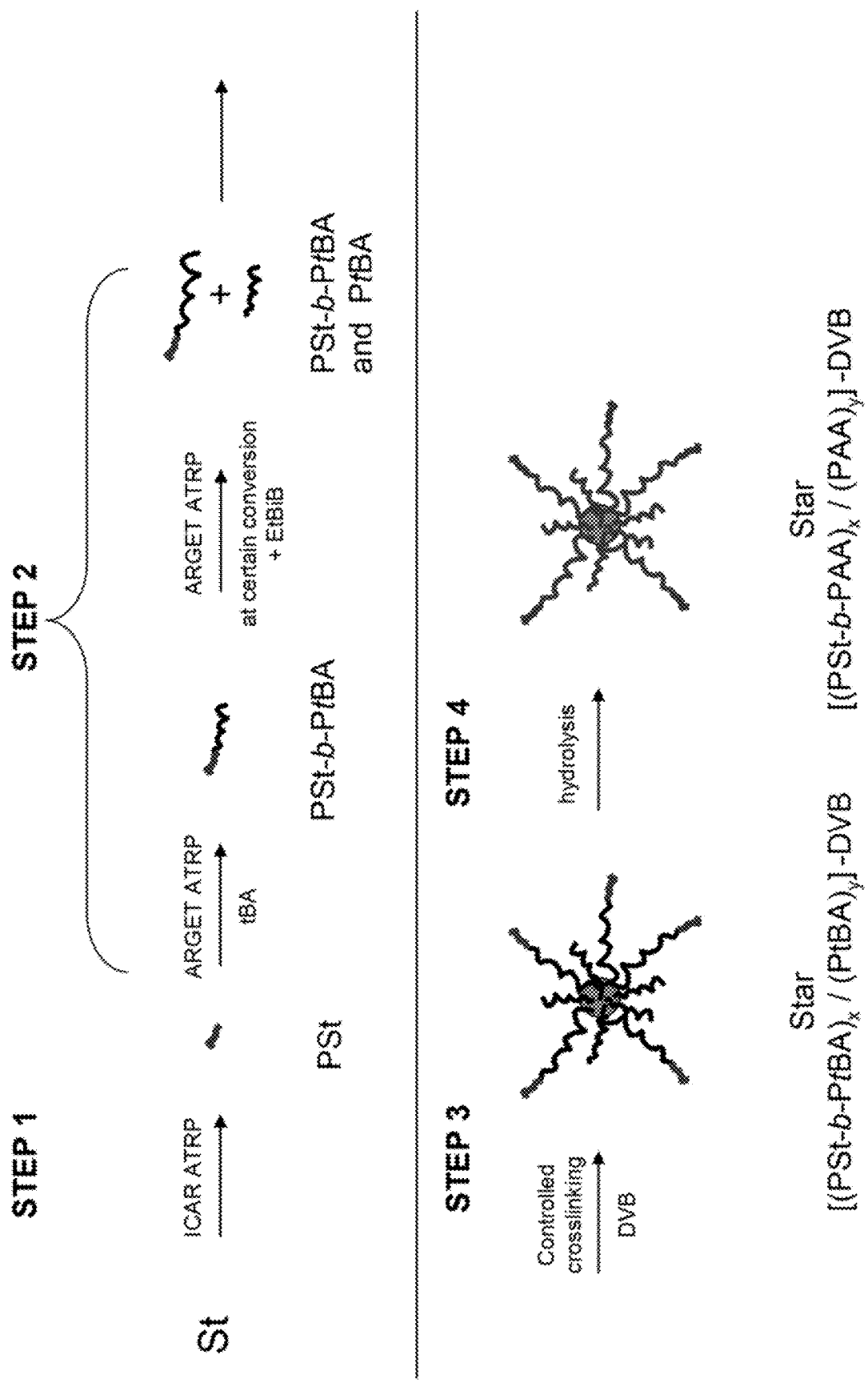
FIG. 26: depicts a multistep synthesis of [PSt-b-PAA/PAA] miktoarm stars copolymers.

The simple four step procedure was developed for the preparation of a poly(acrylic acid) based miktoarm star macromolecule and is described in Scheme 4, as depicted in FIG. 26. 1 kg of the miktoarm star macromolecule with PSt-b-PAA and PAA arms (molar ratio of arms 4/1) was prepared as in Scheme 4.

STEP 1: Synthesis of a Polystyrene Macroinitiator (PSt) Having 15 DP

Figure 23:
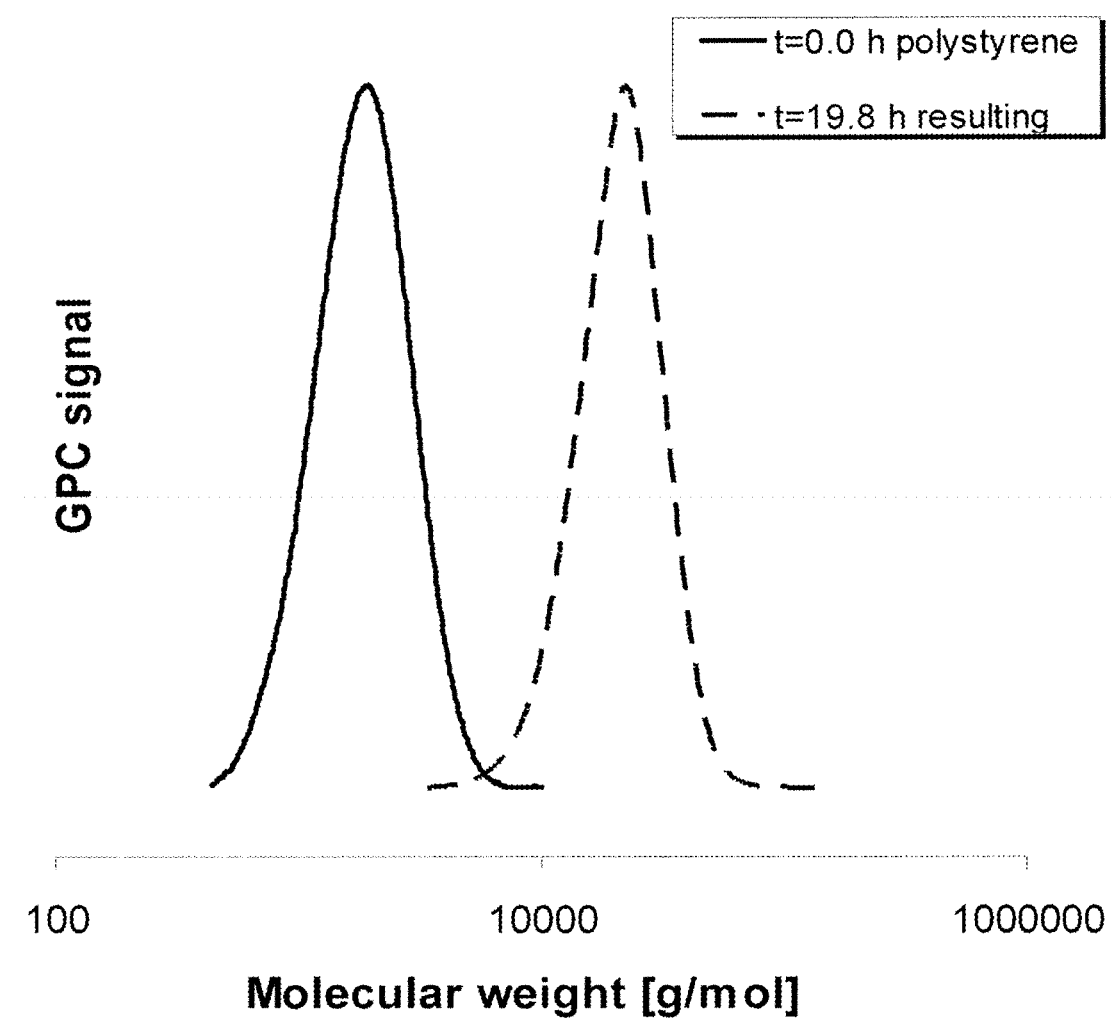
FIG. 23: GPC curves for the reaction product resulting from step 2 of Example 9.

A polystyrene macroinitiator was formed using ICAR ATRP by introducing the following components into the reaction vessel at the following molar ratio: St/DEBMM/$CuBr_2$/TPMA/AIBN=50/1/0.002/0.003/0.05 in bulk at initially introduced components, of Ethyl 2-bromoisobutyrate (EBiB) was injected into the polymerization mixture. The reaction was continued and stopped after about 19.8 h. The reaction product was purified and the product was analyzed by GPC. Based on the GPC measured values the final molecular weight of the product was determined to be poly(t-butyl acrylate) segment in the block copolymer was 37,200 g/mol ($PSt_{15}$-b-$PtBA_{290}$) and the molecular weight of poly(t-butyl acrylate) initiated from EBiB was 19,200 g/mol which is equivalent to a DP=150. The overall molecular weight of mixture of arms resulted in $M_n$=20,800 g/mol and PDI=1.27. The GPC curves of the polystyrene macroinitiator and the mixture of formed block copolymer arms $PSt_{15}$-b-$PtBA_{290}$ and poly(t-butyl acrylate) arms $PtBA_{150}$ are shown in FIG. 23. The signal from block copolymer is overlapping with signal from homopolymer but this result clearly indicates that a clean chain extension from PSt had occurred.

Figure 24:
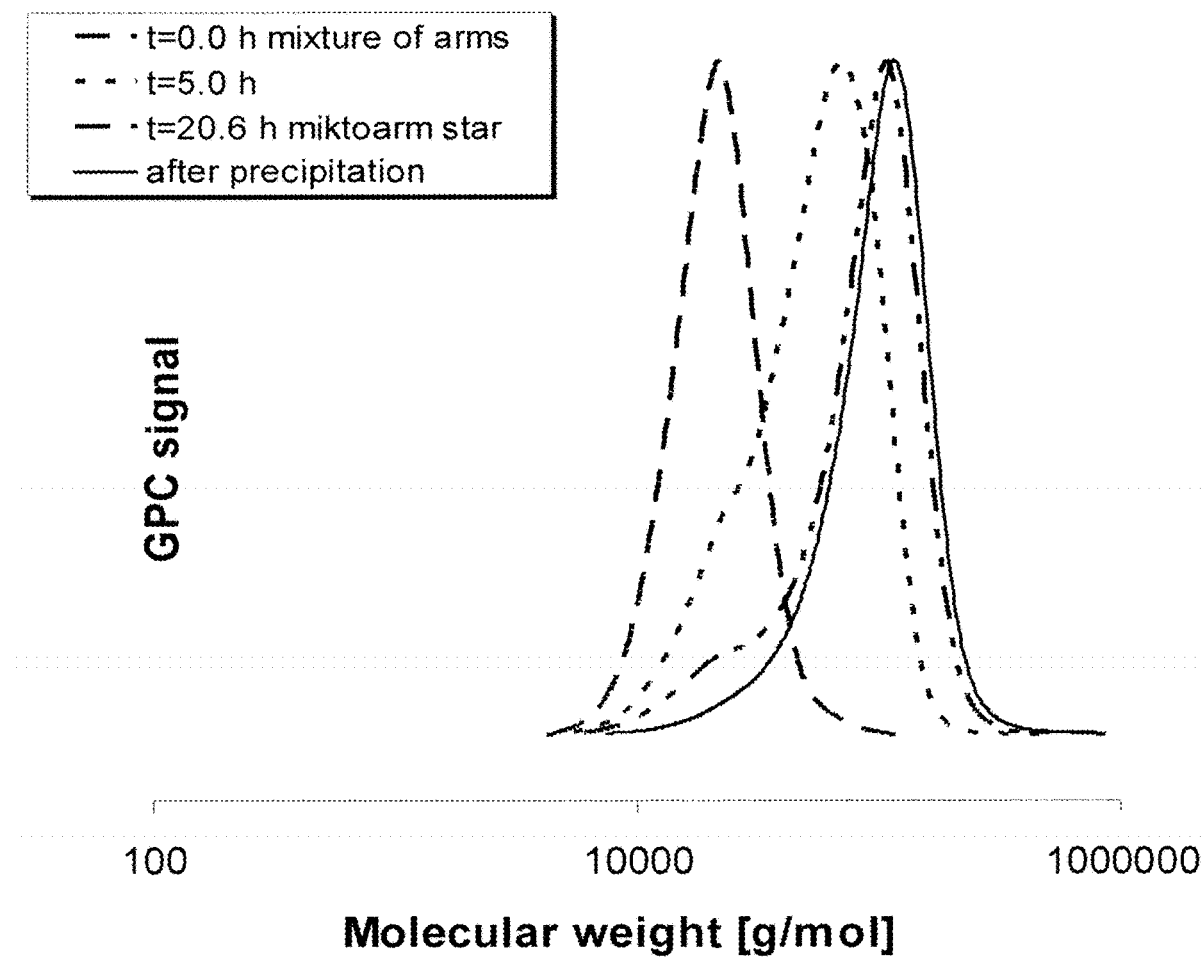
FIG. 24: GPC curves for the reaction product resulting from step 3 of example 9.

STEP 3: Synthesis of the $(PSt$-b-$PtBA/PtBA)_{\sim30}$ Miktoarm Star Macromolecule A mikto multi-arm star macromolecule was prepared by conducting a further chain extension reaction with the block copolymer and homopolymer macroinitiators formed in step 2. The reaction was conducted with a mole ratio of macroinitiators to divinylbenzene of 1:16 in anisole. The following components were introduced into the reaction vessel in the following molar ratio: DVB/[PSt-b-PtBA/PtBA](from step 2)/CuBr$_2$/TPMA/Sn(EH)$_2$=16/1/0.02/0.07/0.15 in anisole (38 volume eq. vs. DVB), T=95° C., t=20.6 h. The reaction product was purified and the product was analyzed by GPC. The GPC curves and results of the star forming reaction are provided in FIG. 24. It can be seen that a multi-arm star macromolecule with a crosslinked core was formed. The GPC apparent molecular weight of the star was 109,400 with a PDI 1.52, which would indicate an average of six arms but this is an underestimate of the actual number of arms since the star molecule is a compact molecule. Indeed in this situation, the number of arms in the star molecule is close to 30.

The number of arms can be modified by conducting the core forming reaction with a different ratio of crosslinking agent to arm precursor or by running the reaction with a different concentration of reagents.

STEP 4: Deprotection of the (PSt-b-PtBA/PtBA) to (PSt-b-PAA/PAA)

Deprotection of the (PSt-b-PtBA/PtBA)$_{\sim 30}$ star macromolecule to (PSt-b-PAA/PAA)$_{\sim 30}$ star block copolymer to provide water soluble poly(acrylic acid) segments in the mikto multi-arm star macromolecule. The PSt-b-PtBA/PtBA arms of the miktoarm star macromolecule were transformed to PSt-b-PAA/PAA arms with the following procedure. Polymer was dissolved in methylene chloride and trifluoroacetic acid to deprotect tBu groups, the reaction was performed at room temperature for 60.0 h. Then polymer was decanted and washed 3 times with acetonitrile. Polymer was then solubilized in THF and precipitated into acetonitrile. The star macromolecule was dried in vacuum oven for 3 days at 50° C. The amount of polymer obtained after purification was 550 g, which would correspond to full conversion of PtBA to PAA.

Test Results Table - comparing the star macromolecule formed in Example 9 (Advantomer) against commercially available thickening agent, Carbopol ETD 2020.

| Properties | Advantomer (as formed in Example 9) | Carbopol ETD 2020 |
|---|---|---|
| Dynamic Viscosity (@1 rpm) | 25,830 cP @ 0.2 wt % | 48,000 cP @ 0.2 wt % |
| Salt-Induced Break Value | 87.8% @ 0.7 wt % | 52.4% @ 0.4 wt % |
| pH-Induced Break Value | 99.3% @ 0.4 wt % | 12.6% @ 0.2 wt % |
| Sheer-Thinning Value | 32.7 @ 0.2 wt % | 12.9 @ 0.2 wt % |
| Strong Gel | Yes | Yes |
| Emulsion Value | >12 hours | <5 min. |
| HLM | >0.96 | N/A |

Test Procedures

Sample Preparation

Aqueous gel compositions were prepared at various concentrations (e.g., 0.2 wt. %, 0.25 wt %, 0.4 wt. % 0.6 wt. %, 0.7 wt. % and 1.0 wt. %) by heating and stirring, as necessary (e.g., vigorously mixing at a temperature of about 60° C.) the sample material (e.g., a star macromolecular powder or Carbopol ETD 2020) into water pH adjusted, as necessary, (e.g., a pH of about 7.5 with addition of sodium hydroxide) to obtain a homogenous mixture.

Dynamic Viscosity & Shear-Thinning Test Procedure

A portion of the sample preparation was introduced into a Brookfield LVDV-E Digital Viscometer, using spindle #31 for mixing, at STP, over a wide range of rates (e.g., 0.3-100 rpm) and the shear rate and viscosity was recorded. Viscosity measurements were taken in the following sequence without stopping the instrument, 0.3, 0.5, 1, 2, 5, 10, 20, 30, 50, and 100 rpm. The dynamic viscosity was determined as the viscosity in centipoise (cP) at 0.3 rpm. A shear-thinning value was determined by dividing the dynamic viscosity value at 0.3 rpm by the dynamic viscosity value at 20 rpm.

| Shear Rate | | Viscosity [cP] | |
|---|---|---|---|
| [s$^{-1}$] | rpm | Advantomer 0.2 wt % | Carbopol 0.2 wt % |
| 0.102 | 0.3 | 67100 | 85000 |
| 0.17 | 0.5 | 46980 | 65600 |
| 0.34 | 1 | 25830 | 48000 |
| 0.68 | 2 | 13880 | 23300 |
| 1.7 | 5 | 6580 | 15800 |
| 3.4 | 10 | 3620 | 10400 |
| 6.8 | 20 | 2050 | 6600 |
| 10.2 | 30 | 1480 | 4800 |
| 17 | 50 | 1000 | 3300 |
| 34 | 100 | 690 | 2250 |

Salt-Induced Break Test Procedure

Figure 18:
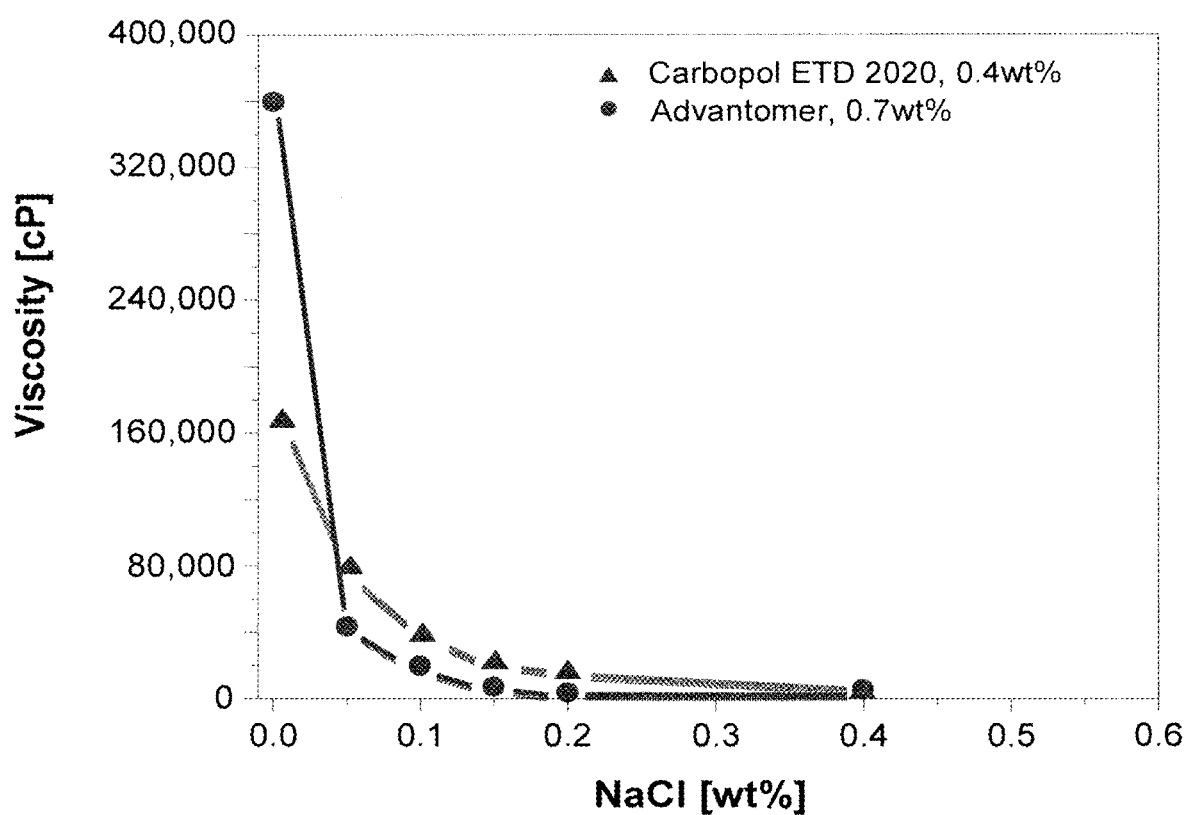
FIG. 18: is a graph comparing viscosity of Advantomer and Carbopol ETD 2020 at varying NaCl weight %.
Figure 22:
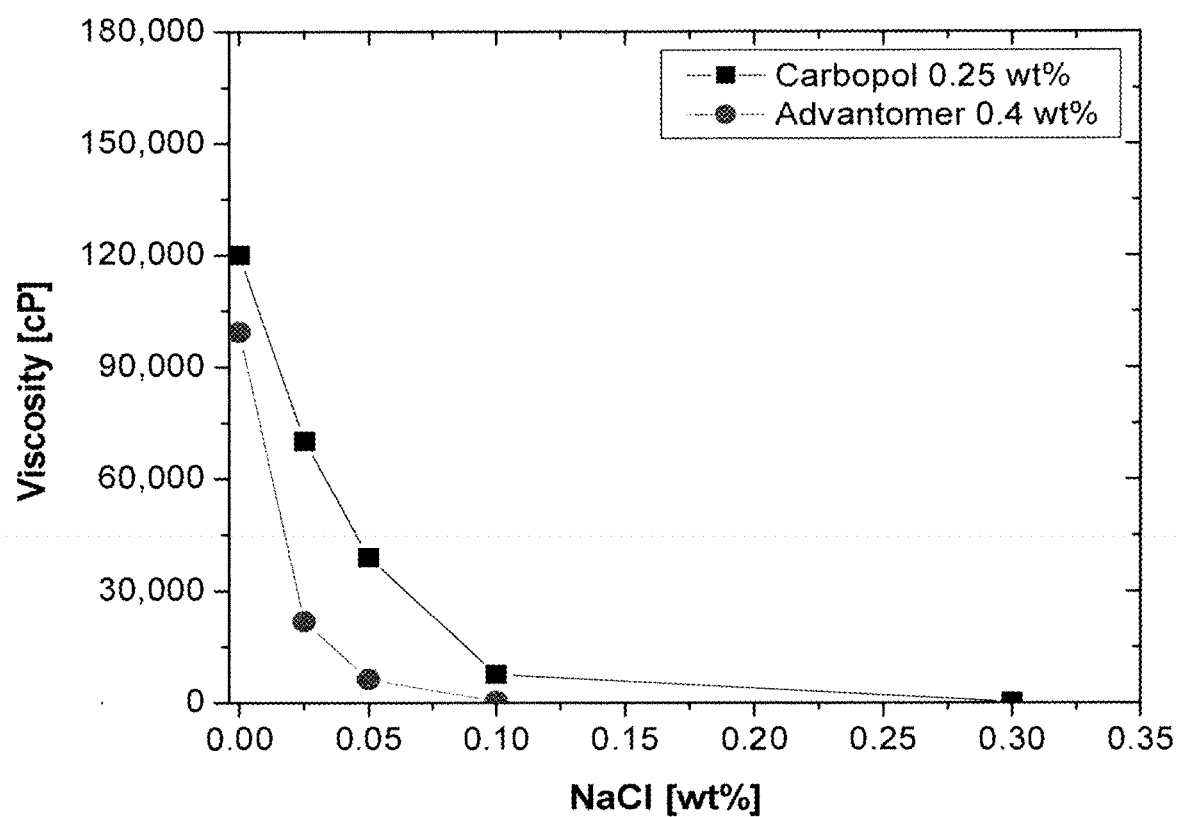
FIG. 22: is a graph comparing viscosity of Advantomer and Carbopol ETD 2020 at varying NaCl weight %.

A portion of the sample preparation was introduced into 20 ml glass scintillation vial. A measured portion of NaCl was added into the vial (e.g., 0.05 wt. % relative to the total weight of the sample in the vial. After the NaCl addition was complete, the vial was closed and shaken for 10 min. Then, the viscosity of the sample was measured in accordance with the Dynamic Viscosity & Shear-Thinning Test Procedure, above, and the dynamic viscosity at 1 rpm was recorded. This procedure was repeated for differing concentrations of NaCl. The results are presented in FIGS. 18 & 22. The salt-induced break value, in percent, is determined by the following equation:

$$\text{Initial Dynamic Viscosity (0\% NaCl)} - \text{Dynamic Viscosity (0.05 wt. \% NaCl)} / \text{Initial Dynamic Viscosity (0\% NaCl)} \times 100\%.$$

pH Efficiency Range Test Procedure

Figure 19:
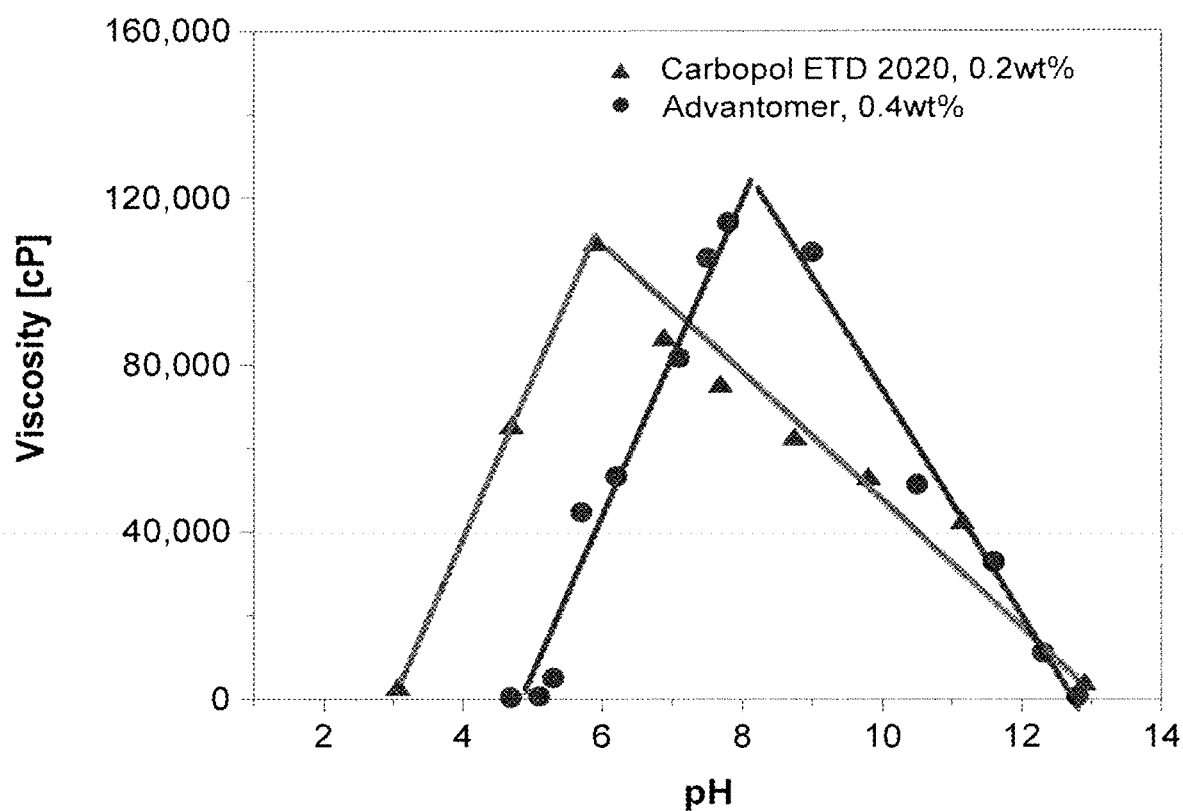
FIG. 19: is a graph comparing viscosity of Advantomer and Carbopol ETD 2020 at varying pH.
Figure 20:
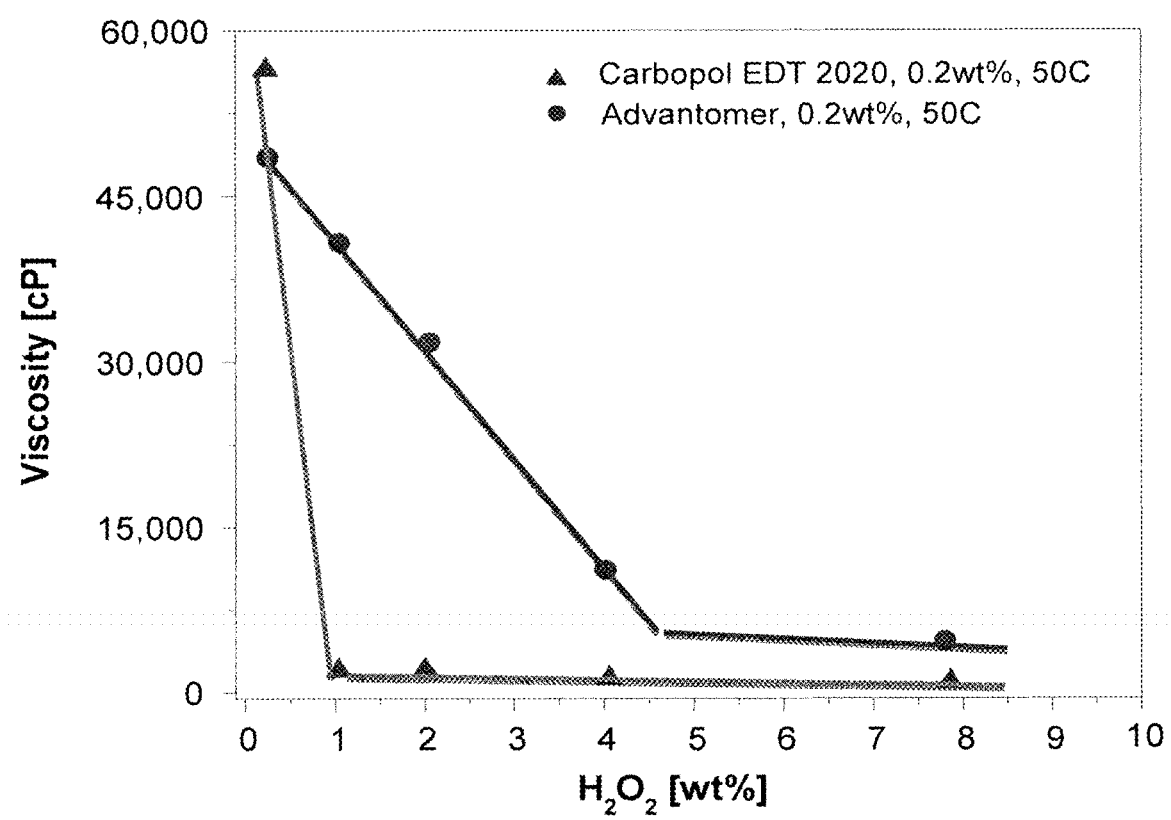
FIG. 20: is a graph comparing viscosity of Advantomer and Carbopol ETD 2020 at varying $H_2O_2$ weight %.
Figure 21:
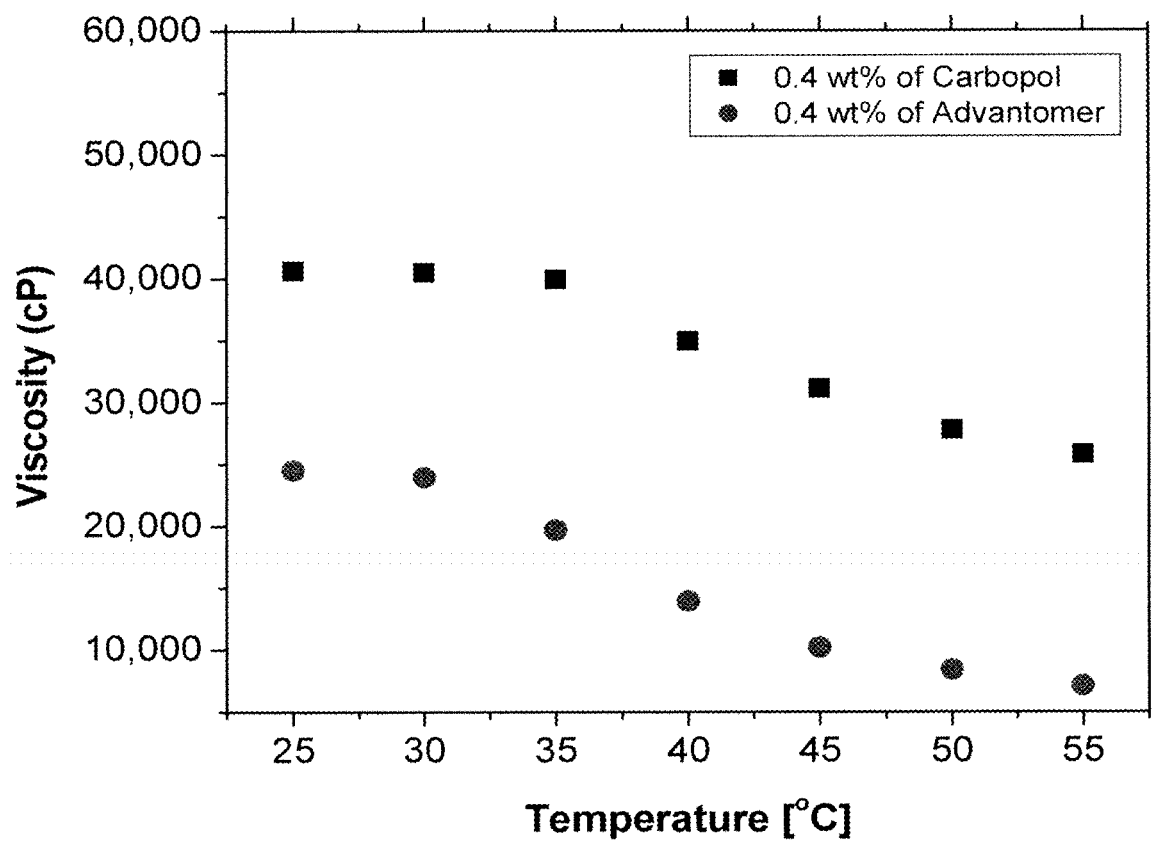
FIG. 21: is a graph comparing viscosity of Advantomer and Carbopol ETD 2020 at varying temperatures.

An aqueous gel composition at 0.4 wt. % was prepared for the star macromolecule of Example 9, at a starting pH of around 5 and a separate aqueous gel composition at 0.2 wt. % aqueous gel composition of Carbopol ETD 2020, at a starting pH of around 3, was prepared by mixing and heating, as necessary (e.g., vigorous mixing at a temperature of about 60° C.). Then, the viscosity of the sample was measured in accordance with the Dynamic Viscosity & Shear-Thinning Test Procedure, above, and the dynamic viscosity at 1 rpm was recorded. This procedure was repeated for differing pH values, adjusted by addition of sodium hydroxide. The results are presented in FIG. 19. The ph-induced break value, in percent, is determined by the following equation:

$$\text{Dynamic Viscosity (at 1 rpm) at pH 7.5} - \text{Dynamic Viscosity (at 1 rpm) at pH 5} / \text{Dynamic Viscosity (at 1 rpm) at pH 7.5} \times 100\%.$$

Emulsion Test Procedure 340 mL of water was added to a 500 ml beaker and stirred vigorously with an overhead stirrer. 1.6 g of the material to be tested for emulsifying effect was added and heated to 80 C. The solution was pH adjusted with 400 mg of NaOH and stirring continued until a homogeneous gel was obtained. 60 ml sunflower oil was added while vigorous stirring was continued with an overhead stirrer at 80 C for 10 min or until homogenous emulsion is obtained. The mixture was allowed to cool to room temperature. Once the system cools to room temperature start timer. The emulsion value is the time, in minutes, it takes for the system to form two visible layers (phase separation).

Strong Gel Test Procedure 10 ml portion of the sample preparation material was introduced into a 20 ml glass scintillation vial. After the transfer was complete, the vial was placed on a surface and remained undisturbed for about 20 minutes at STP. The vial was then gently inverted (turned-upside down) and placed on the surface and a timer started. If after 5 minutes, there is no visible flow then the sample is said to be a strong gel.

Hydrophilic-Lipophilic (HLB) Arm/Segment Calculation $$HLB = 20 * Mh/M$$

where Mh is the molecular mass of the hydrophilic portion of the polymeric arm or segment, and M is the molecular mass of the whole polymeric arm or segment.

Hydrophilic-Lipophilic Macromolecule Calculation $$HLM = \sum_{n=1}^{n-m} MW_n \times HLB_n / 20 \text{ divided by } 0.3 MW_{core} + \sum_{n=1}^{n-m} MW_n$$

where $MW_n$ is the molecular weight for the respective arm, $HLB_n$ is the HLB, as calculated from the HLB arm calculation, for the respective arm, and $MW_{core}$ is the molecular weight for the core, and M is the total number of arms.

The disclosed star macromolecules can find utility in a spectrum of applications including, but not limited to; personal care: including shampoos/conditioners, lotions, serums, creams, solids, gelly, cosmetics: including mascara, blush, lip stick, powders, perfumes and home care: including cleaners for windows, household and work surfaces, toilet areas, laundry, and in dish and dishwasher applications.

What is claimed is:

1. A star macromolecule represented by the Formula:

[(P1)q1-(P2)2]t-Core-[(P3)3]r    Formula wherein:
Core represents a crosslinked polymeric segment;
P1 represents a hydrophobic polymeric segment comprised of repeat units of monomeric residues of polymerized monomers;
P2 represents a polymeric segment comprised of repeat units of monomeric residues of polymerized monomers;
P3 represents a hydrophobic polymeric segment comprised of repeat units of monomeric residues of polymerized monomers;
q1 represents the number of repeat units in P1;
q2 represents the number of repeat units in P2;
q3 represents the number of repeat units in P3;
t represents the number of copolymeric arms covalently attached to the Core;
r represents the number of polymeric arms covalently attached to the Core; and
wherein
one or more of the repeat units of monomeric residues of polymerized monomers within P1 and P3 comprise one or more of (meth)acrylic acid and 2-acrylamido-2-methyl-1-propanesulfonic acid; and
P1 and P2 are different.

2. The star macromolecule of claim 1 is an oil-soluble rheology-modifying star macromolecule.

3. The star macromolecule of claim 1 is a thickener for an oil-based system.

4. The star macromolecule of claim 1 controls rheology in an oil based system.

5. The star macromolecule of claim 1 wherein:
q1 has a value of between 10 and 1000;
q2 has as a value between 50 and 1000; and
q3 has a value between 20 and 500.

6. The star macromolecule of claim 1 wherein the molar ratio of r to t is in the range of between 40:1 and 1:40.

7. The star macromolecule of claim 1, wherein the arms represented by $[(P1)_{q1}-(P2)_{q2}]_t$ extend beyond the arms represented by $[(P3)_{q3}]_r$.

8. The star macromolecule of claim 1, wherein the number of polymeric arms (r+t) is between 5 and 500.

9. The star macromolecule of claim 1, wherein (r+t) is greater than 15.

10. The star macromolecule of claim 1, wherein q2 is greater than q3.

11. The star macromolecule of claim 1, wherein P2 represents a hydrophobic polymeric segment comprised of repeat units of monomeric residues of polymerized monomers.

12. The star macromolecule of claim 1, wherein the repeat units of monomeric residues of polymerized monomers within P1, P2, or P3 further comprise a monomeric residue of a polymerized alkyl (meth)acrylate.

13. The star macromolecule of claim 1, wherein the repeat units of monomeric residues of polymerized monomers within P1, P2, or P3 further comprise a monomeric residue of a polymerized methyl methacrylate.

14. The star macromolecule of claim 1, wherein the repeat units of monomeric residues of polymerized monomers within P1, P2, or P3 further comprise a monomeric residue of a polymerized styrene optionally substituted with one or more C1-C12 straight or branched chain alkyl groups.

15. The star macromolecule of claim 1, wherein the repeat units of monomeric residues of polymerized monomers within P1, P2, or P3 further comprise a monomeric residue of a polymerized: dodecyl acrylate, N-dodecyl methacrylamide, styrene or 2-ethylhexyl methacrylate.

16. The star macromolecule of claim 1, wherein the repeat units of monomeric residues of polymerized monomers within P1, P2, or P3 further comprise a monomeric residue of a polymerized acrylamide.

17. The star macromolecule of claim 1, wherein the Core comprises monomeric residues of polymerized monomers comprising: 1,2-divinylbenzene; 1,3-divinylbenzene; 1,4-divinylbenzene; 1,2-ethanediol di(meth)acrylate; 1,3-propanediol di(meth)acrylate; 1,4-butanediol di(meth)acrylate; 1,5-hexanediol di(meth)acrylate; divinylbenzene; ethyleneglycol di(meth)acrylate; di(ethylene glycol) diacrylate (DEGlyDA); propyleneglycol di(meth)acrylate; butyleneglycol di(meth)acrylate; triethyleneglycol di(meth)acrylate; polyethyleneglycol di(meth)acrylate; polypropyleneglycol di(meth)acrylate; polybutyleneglycol di(meth)acrylate; allyl(meth)acrylate; glycerol di(meth)acrylate; trimethylolpropane ti(meth)acrylate; pentaerythritol tetra(meth)acrylate; ally' methacrylate; allyl acrylate, di(ethylene glycol) diacrylate (DEGlyDA), or divinylbenzene.

18. The star macromolecule of claim 1, wherein the polymeric segments P1, P2, and/or P3 are random polymeric segments.

19. The star macromolecule of claim 1, wherein the Core comprises, by weight:

about 0.5%, or more, monomeric residues of polymerized monomers from P2 and P3, and about 0.5%, or more, monomeric residues of polymerized monomers different from the monomeric residues of polymerized monomers from P1, P2, or P3.

20. The star macromolecule of claim 1, wherein the Core is crosslinked by a crosslinker comprising ethyleneglycol di(meth)acrylate; trimethylolpropane tri(meth)acrylate; propyleneglycol di(meth)acrylate; di(ethylene glycol) diacrylate (DEGlyDA); triethyleneglycol di(meth)acrylate; polyethyleneglycol di(meth)acrylate; polypropyleneglycol di(meth)acrylate; 1,4-divinylbenzene; 1,2-divinylbenzene; 1,3-divinylbenzene; 1,2-ethanediol di(meth)acrylate; 1,3-propanediol di(meth)acrylate; 1,4-butanediol di(meth)acrylate; 1,5-hexanediol di(meth)acrylate; divinylbenzene; butyleneglycol di(meth)acrylate; polybutyleneglycol di(meth)acrylate; allyl(meth)acrylate; glycerol di(meth)acrylate; pentaerythritol tetra(meth)acrylate; allyl methacrylate; allyl acrylate; or divinylbenzene.

* * * * *

UNITED STATES PATENT AND TRADEMARK OFFICE
CERTIFICATE OF CORRECTION

PATENT NO. : 11,168,182 B2  
APPLICATION NO. : 16/914056  
DATED : November 9, 2021  
INVENTOR(S) : Wojciech Jakubowski et al.

Page 1 of 1

It is certified that error appears in the above-identified patent and that said Letters Patent is hereby corrected as shown below:

In the Specification

Column 3, Line 19, change "$[(P1)_{q1}\text{-}(P2)_{q2}]_t\text{-Core-}[(P3)_{q3}]_r$" to --$[(P1)_{q1}\text{-}(P2)_{q2}]_t\text{-Core-}[(P3)_{q3}]_r$--;

In the Claims

Column 39, Claim 1, Line 62, change "$[(P1)q1\text{-}(P2)2]t\text{-Core-}[(P3)3]r$" to --$[(P1)_{q1}\text{-}(P2)_{q2}]_t\text{-Core-}[(P3)_{q3}]_r$--;

Column 40, Claim 7, Line 34, change "$[(P1)_{q1}\text{-}(P2)_{q2}]_t$" to --$[(P1)_{q1}\text{-}(P2)_{q2}]_t$--; and Column 40, Claim 7, Line 35, change "$[(P3)_{q3}]_r$" to --$[(P3)_{q3}]_r$--.

Signed and Sealed this  
Fourth Day of January, 2022

Drew Hirshfeld  
*Performing the Functions and Duties of the*  
*Under Secretary of Commerce for Intellectual Property and*  
*Director of the United States Patent and Trademark Office*